United States Patent
Zheng et al.

(10) Patent No.: US 12,404,300 B2
(45) Date of Patent: Sep. 2, 2025

(54) MITOCHONDRIA-TARGETING PEPTIDES

(71) Applicant: Stealth BioTherapeutics Inc., Needham, MA (US)

(72) Inventors: Guozhu Zheng, Lexington, MA (US); Mark J. Bamberger, South Glastonbury, CT (US); Inese Smukste, Weston, MA (US)

(73) Assignee: Stealth BioTherapeutics Inc., Needham, MA (US)

( * ) Notice: Subject to any disclaimer, the term of this patent is extended or adjusted under 35 U.S.C. 154(b) by 371 days.

(21) Appl. No.: 17/414,103

(22) PCT Filed: Nov. 19, 2019

(86) PCT No.: PCT/US2019/062283
§ 371 (c)(1),
(2) Date: Jun. 15, 2021

(87) PCT Pub. No.: WO2020/131282
PCT Pub. Date: Jun. 25, 2020

(65) Prior Publication Data
US 2022/0041653 A1 Feb. 10, 2022

Related U.S. Application Data

(60) Provisional application No. 62/892,939, filed on Aug. 28, 2019, provisional application No. 62/781,153, filed on Dec. 18, 2018.

(51) Int. Cl.
*C07K 5/107* (2006.01)
*A61P 9/10* (2006.01)
*C07K 7/06* (2006.01)
*A61K 38/00* (2006.01)

(52) U.S. Cl.
CPC .............. *C07K 5/1016* (2013.01); *A61P 9/10* (2018.01); *C07K 7/06* (2013.01); *A61K 38/00* (2013.01)

(58) Field of Classification Search
None
See application file for complete search history.

(56) References Cited

U.S. PATENT DOCUMENTS

| | | |
|---|---|---|
| 2011/0118441 A1 | 5/2011 | Gao |
| 2014/0294796 A1 | 10/2014 | Wilson et al. |
| 2015/0010588 A1 | 1/2015 | Szeto |
| 2022/0041654 A1 | 2/2022 | Zheng et al. |

FOREIGN PATENT DOCUMENTS

| | | |
|---|---|---|
| WO | WO-2004/070054 A2 | 8/2004 |
| WO | WO-2011/116007 A1 | 9/2011 |
| WO | WO-2012/006569 A1 | 1/2012 |
| WO | WO-2012/022467 A2 | 2/2012 |
| WO | WO-2012/174117 A2 | 12/2012 |
| WO | WO-2017/093897 A1 | 6/2017 |
| WO | WO-2017/180535 A1 | 10/2017 |
| WO | WO-2020/131282 A1 | 6/2020 |

OTHER PUBLICATIONS

Ericson et al. ('Discovery of a beta-hairpin octapeptide, c[Pro-Arg-Phe-Phe-Dap-Ala-Phe-DPro], mimetic of agouti-related protein(87-132) [AGRP(87-132)] with equipotent mouse melanocortin-4 receptor (mMC4R) antagonist pharmacology' J Med Chem v58 2015 pp. 4638-4647) (Year: 2015).*
International Search Report and Written Opinion for International Application No. PCT/US2019/062283 mailed Mar. 13, 2020.
Bai et al., "[Dmt1] DALDA anlogues with enhanced [mu] opioid agonist potency and with a mixed [mu]/[kappa] opioid acti" BioOrganic, 22(7), 2333-2338 (2014).
Dai et al., "Cardioprotective Effects of Mitochondria-Targeted Peptide SBT-20 in two Different Models of Rat Ischemia/Reperfusion," Cardiovascular Drugs and Therapy, 30(6): 559-566 (2016).
Extended European Search Report for EP Application No. 19898721.6 dated Jul. 21, 2022.
Koster et al., "A spontaneous gold(i)—azide alkyne cycloaddition reaction yields gold-peptide bioconjugates which overcome cisplatin resistance in a p53 mutant cancer cell line" Chemical Science, 3(6): 2062 (2012).

* cited by examiner

*Primary Examiner* — Ronald T Niebauer
(74) *Attorney, Agent, or Firm* — Foley Hoag LLP; Dana M. Gordon; Hilary D. Lang

(57) ABSTRACT

Disclosed are analogs of SBT-20. The compounds are useful for the treatment and prevention of ischemia-reperfusion injury (e.g., cardiac ischemia-reperfusion injury) or myocardial infarction.

22 Claims, 4 Drawing Sheets

Figure 1

| CAS No. | Vendor (Catalog No.) or Literature Citation | Structure |
|---|---|---|
| 96539-87-6 | Aldrich (38473) | 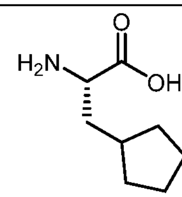 |
| 155760-02-4 | QM Bio (8253011) | 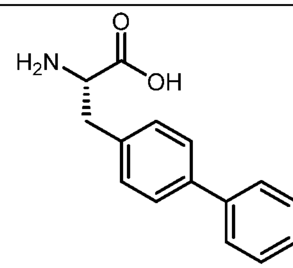 |
| 2935-35-5 | Alfa Aesar (30314) | 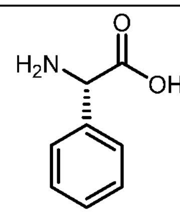 |
| 95975-81-8 | Do, et al. Helvetica, 1979, V. 62, No. 4, 956-964. | 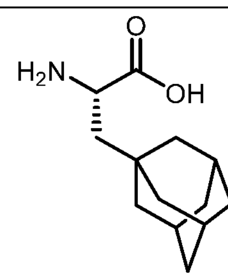 |

Rat permeabilized cardiac fiber A/R

MITOCHONDRIA-TARGETING PEPTIDES

RELATED APPLICATIONS

This application is a U.S. National Stage Application of International Application No. PCT/US19/62283, filed Nov. 19, 2019; which claims the benefit of priority to U.S. Provisional Patent Application Nos. 62/781,153, filed Dec. 18, 2018; and 62/892,939, filed Aug. 28, 2019.

BACKGROUND OF THE INVENTION

SBT-20 is a mitochondria-targeting peptide compound with therapeutic potential for treating diseases associated with mitochondrial dysfunction. Because of the potential therapeutic applications of SBT-20, there exists a need to develop analogs of the compound with an improved therapeutic profile.

SUMMARY OF THE INVENTION

An aspect of the invention is an analog of SBT-20.

More specifically, the invention provides a compound of formula (I), or a pharmaceutically acceptable salt thereof:

Aaa$^1$—Aaa$^2$—Aaa$^3$—Aaa$^4$—N(R$^a$)(R$^b$)      (I)

wherein:

Aaa$^1$ is an amino acid residue selected from the group consisting of:

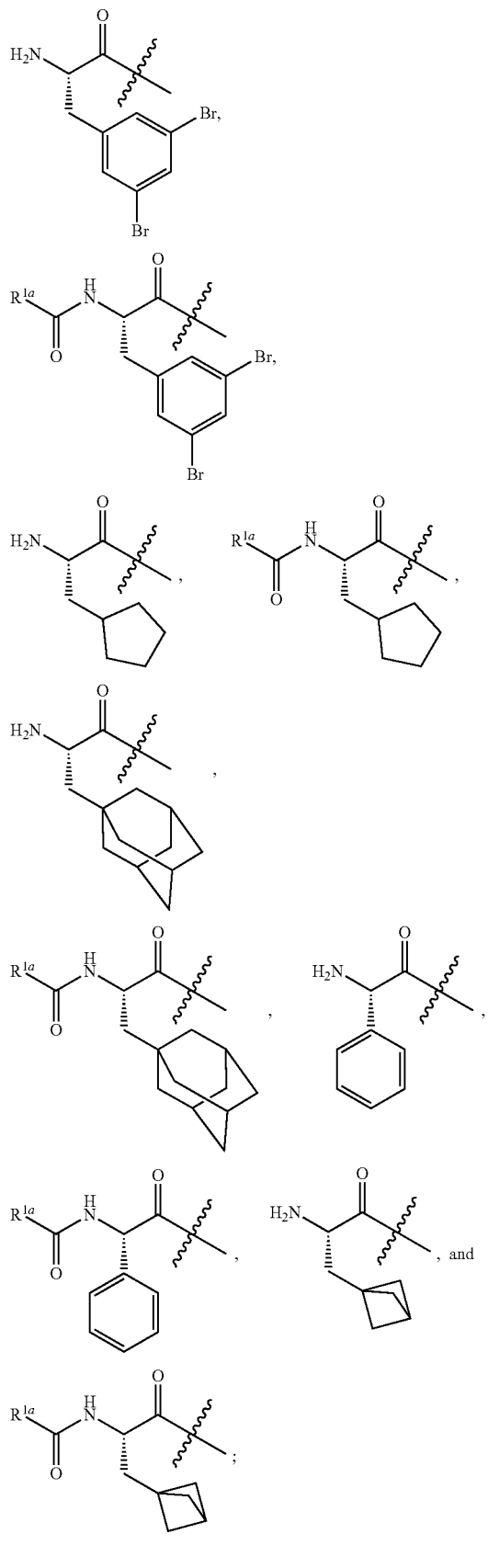

Aaa¹ is

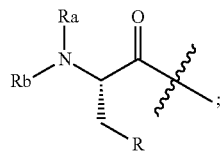

wherein R is an optionally substituted alkyl, cycloalkyl, heterocyclyl, aryl, heteroaryl, aralkyl, or heteroaralkyl; and Ra and Rb are each independently selected from H, methyl, ethyl, propyl, cyclopropyl, cyclobutyl; or Ra and Rb taken together with the nitrogen atom to which they are attached form a four-, five- or six-membered heterocyclic ring;

Aaa² is an amino acid residue selected from the group consisting of:

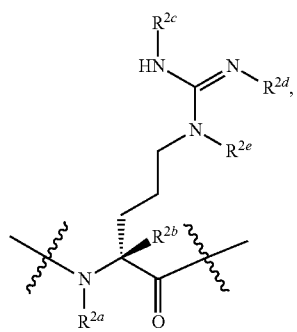

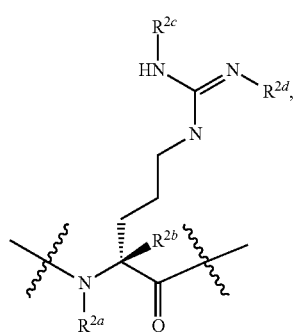

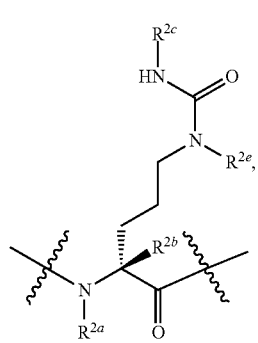

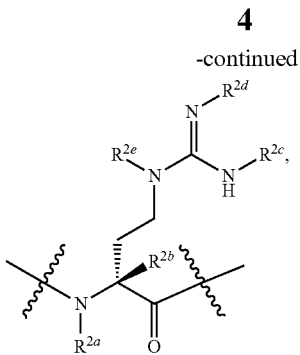

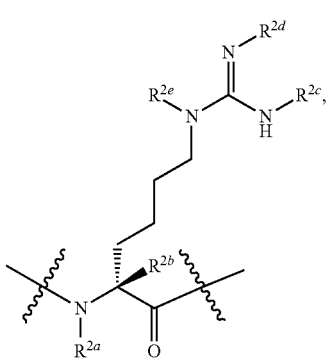

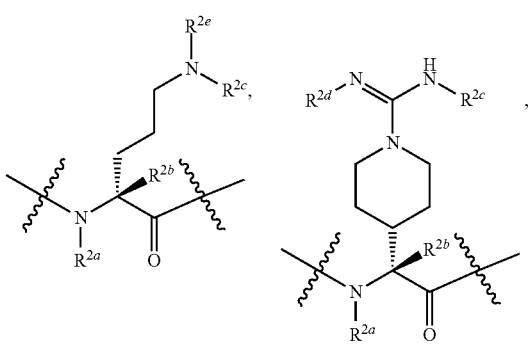

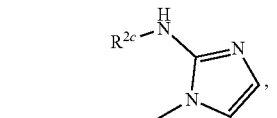

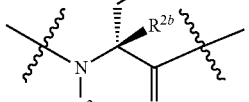

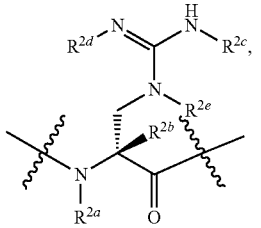

-continued
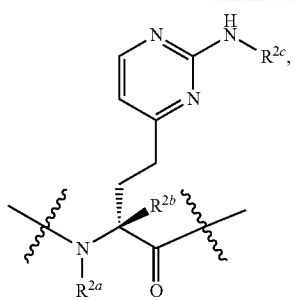
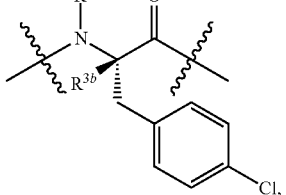
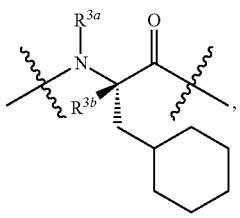
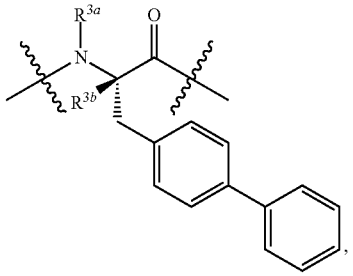, and
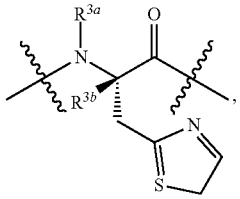;
Aaa³ is an amino acid residue selected from the group consisting of:
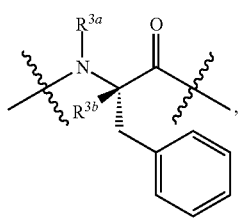,
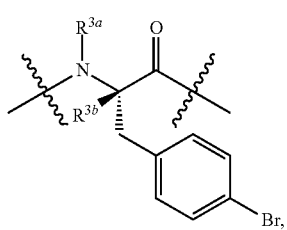,
-continued
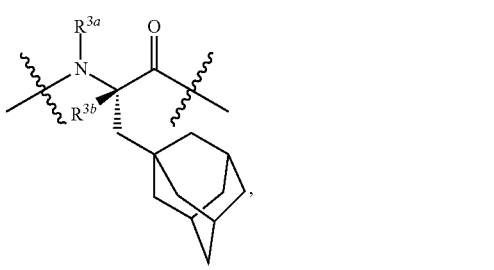
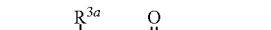
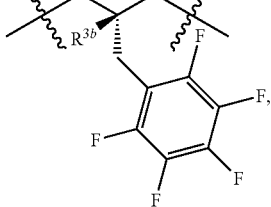
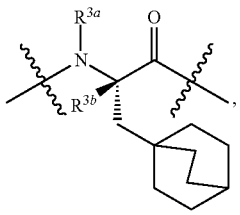 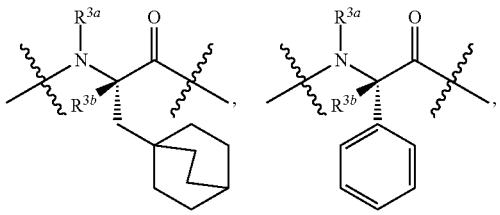

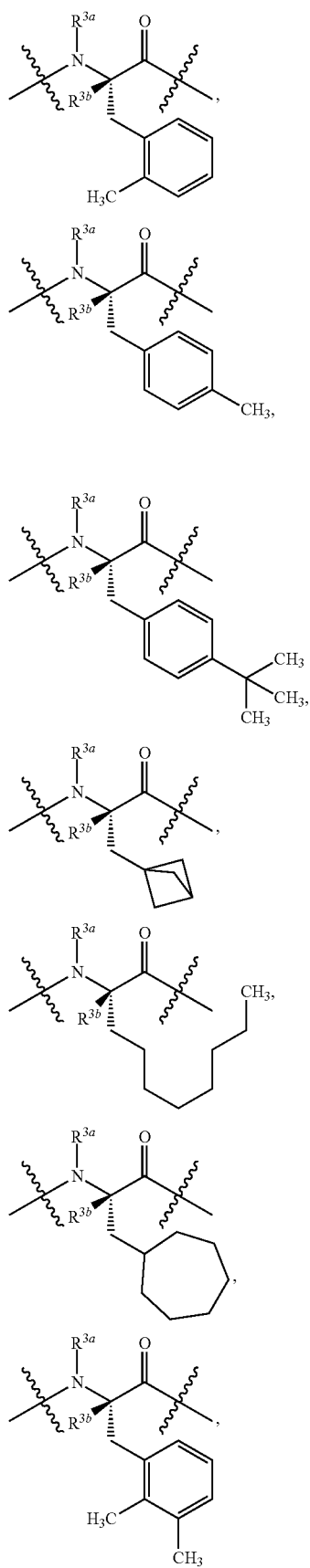
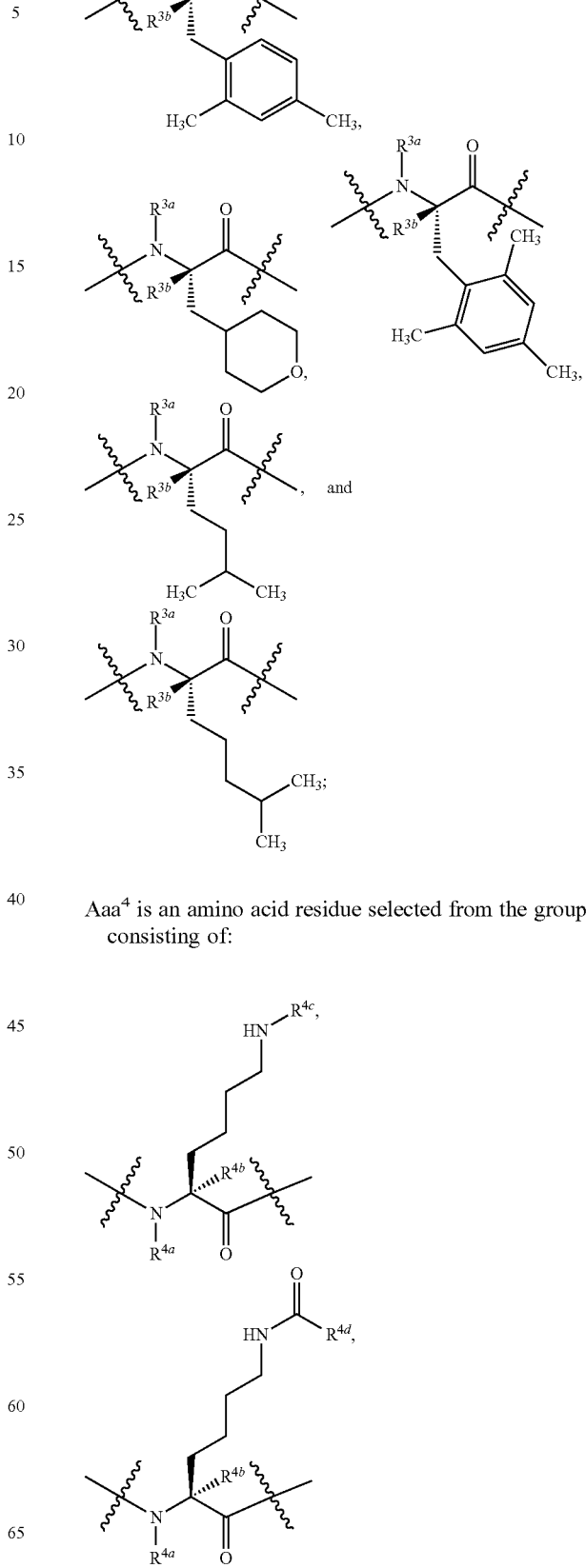
Aaa⁴ is an amino acid residue selected from the group consisting of:

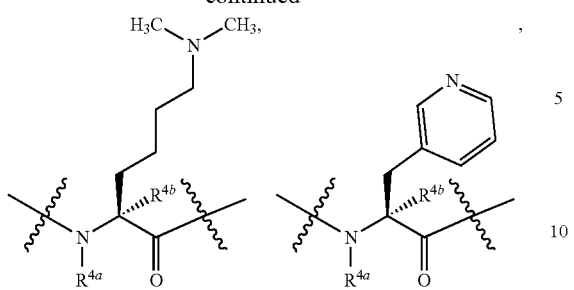
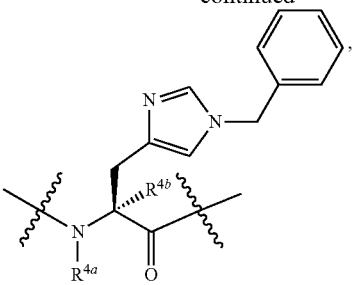
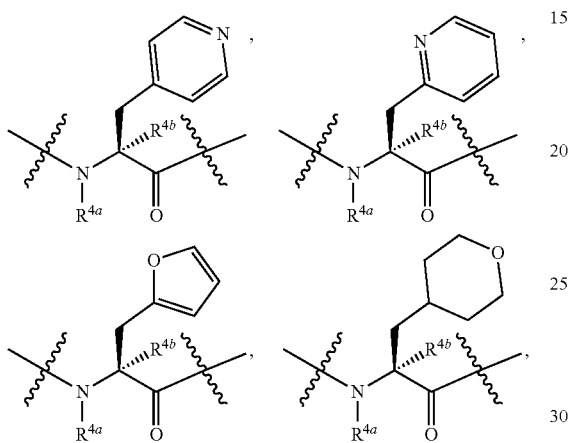
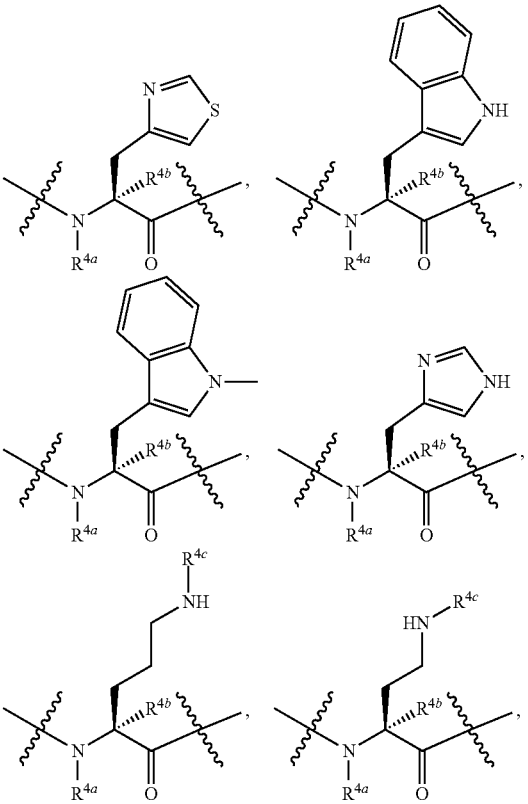
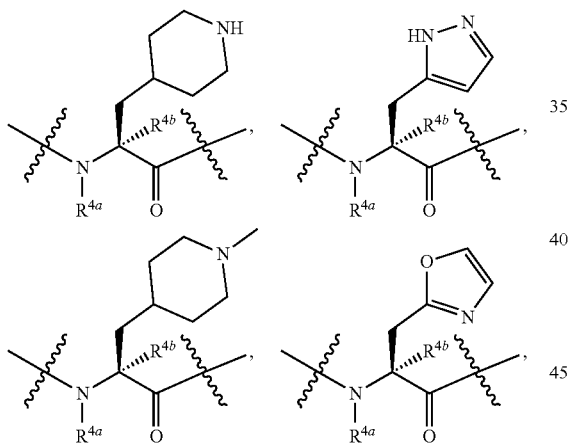
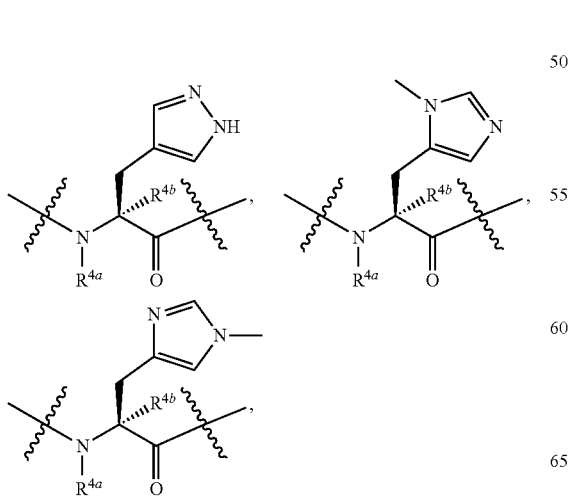
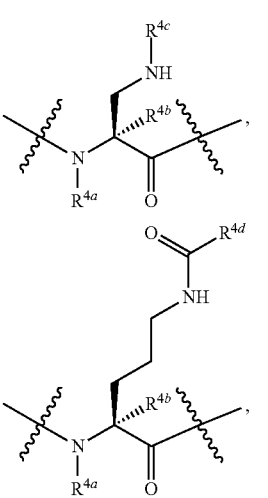

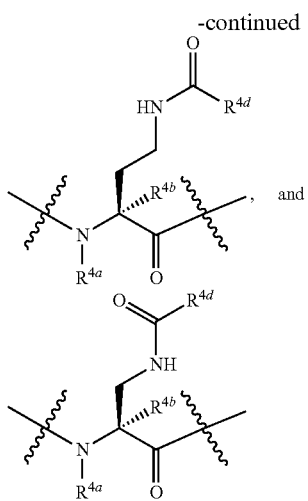

$R^{1a}$ and $R^{4d}$ are each independently $(C_1-C_6)$alkyl;
$R^{2a}$, $R^{2b}$, $R^{2c}$, $R^{3a}$, $R^{3b}$, $R^{4a}$, $R^{4b}$, $R^{4c}$ are each independently selected from the group consisting of H and $(C_1-C_6)$alkyl; and
$R^a$, $R^b$, $R^{2c}$, and $R^{2d}$ are each independently selected from the group consisting of H, $(C_1-C_6)$alkyl, $C(O)((C_1-C_6)$alkyl), $C(O)((C_1-C_6)$haloalkyl), $C(O)O((C_1-C_6)$alkyl), and $C(O)O(aryl(C_1-C_6)$alkyl);
provided that the compound of formula (I) is not

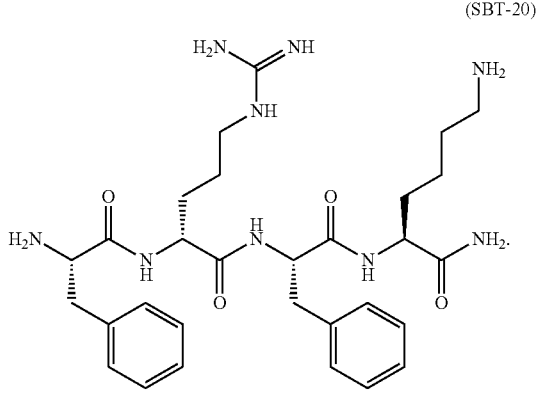

(SBT-20)

Another aspect of the invention is a pharmaceutical composition, comprising a compound of the invention; and a pharmaceutically acceptable carrier.

The invention also provides methods of treating or preventing ischemia-reperfusion injury, comprising administering to a subject in need thereof a therapeutically effective amount of a compound of the invention.

The invention also provides methods of treating or preventing myocardial infarction, comprising administering to a subject in need thereof a therapeutically effective amount of a compound of the invention.

BRIEF DESCRIPTION OF THE DRAWINGS

FIG. 1 depicts various amino acid residues useful in the present invention.

DETAILED DESCRIPTION OF THE INVENTION

Figure 2:
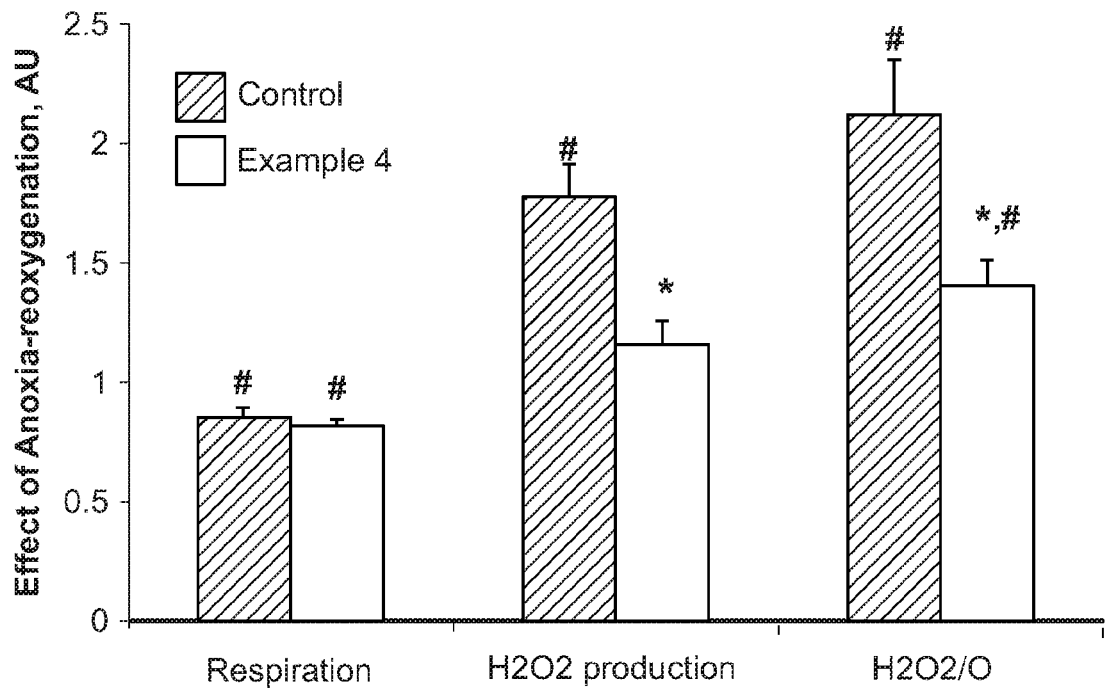
FIG. 2 depicts rat permeabilized cardiac fiber A/R. See Example 30.

SBT-20 (Phe-D-Arg-Phe-Lys-NH$_2$) is a mitochondria-targeting compound with therapeutic potential for treating ischemia-reperfusion injury (e.g., cardiac ischemia-reperfusion injury), and myocardial infarction. Analogs of this compound may have improved therapeutic profiles, including improved metabolic properties, selectivity, or potency.

Accordingly, in certain embodiments, the invention provides a compound of formula (I), or a pharmaceutically acceptable salt thereof:

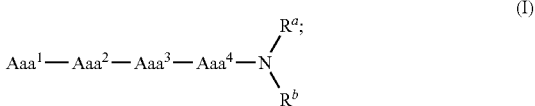

wherein:
Aaa$^1$ is an amino acid residue selected from the group consisting of:

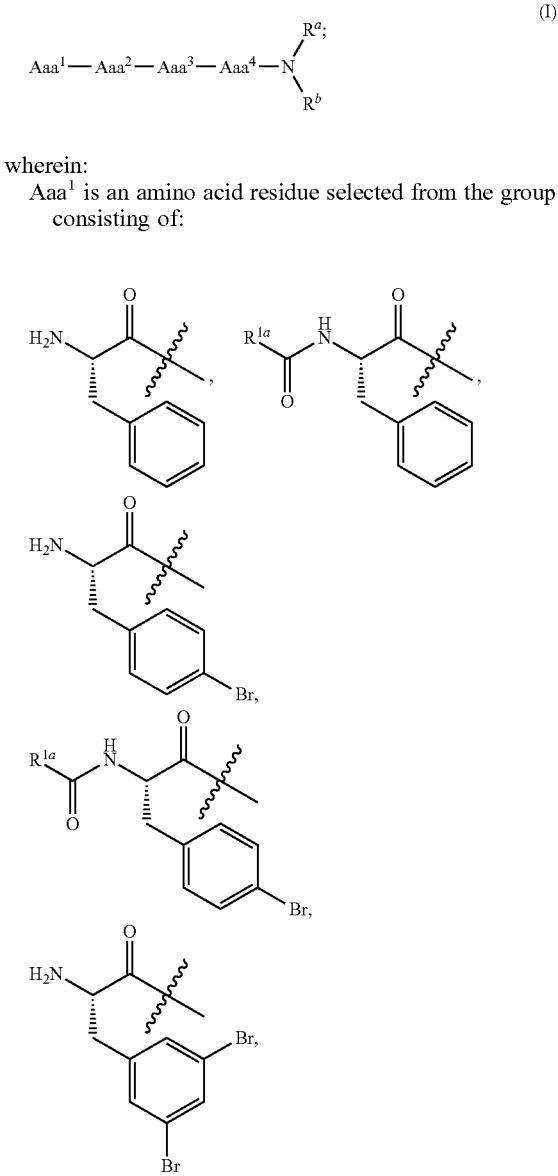

-continued

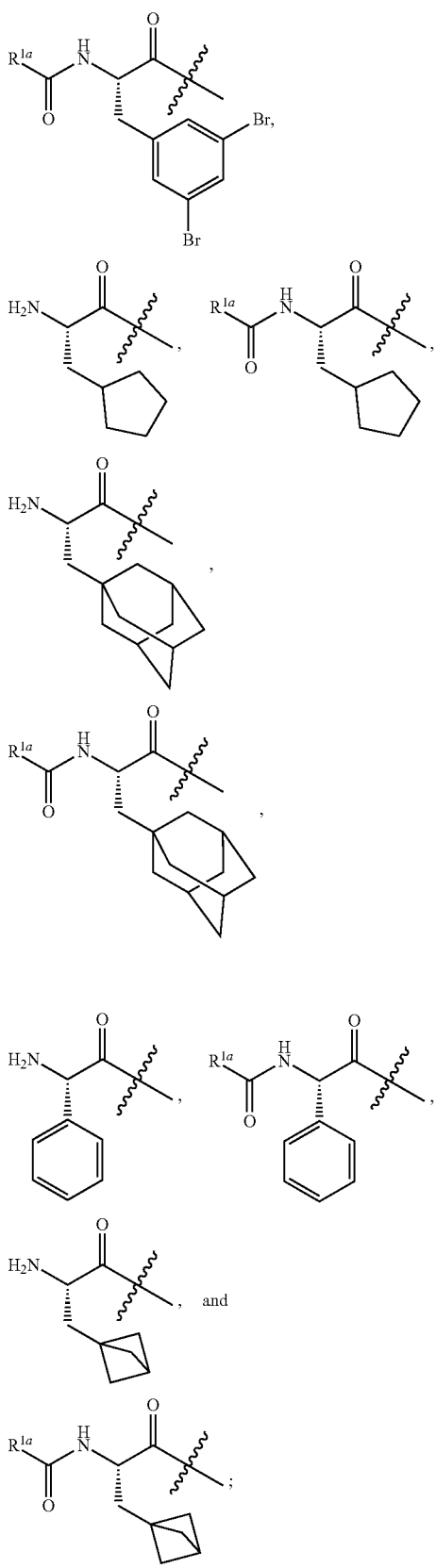

or

Aaa¹ is

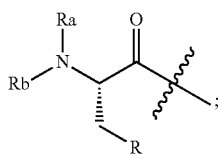

wherein R is an optionally substituted alkyl, cycloalkyl, heterocyclyl, aryl, heteroaryl, aralkyl, or heteroaralkyl; and Ra and Rb are each independently selected from H, methyl, ethyl, propyl, cyclopropyl, cyclobutyl; or Ra and Rb taken together with the nitrogen atom to which they are attached form a four-, five- or six-membered heterocyclic ring;

Aaa² is an amino acid residue selected from the group consisting of:

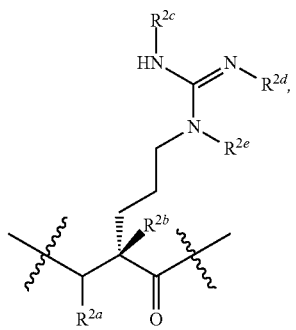

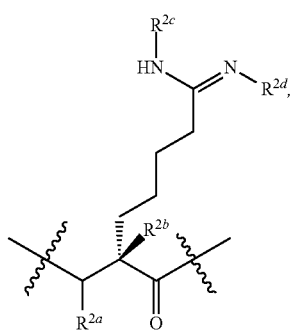

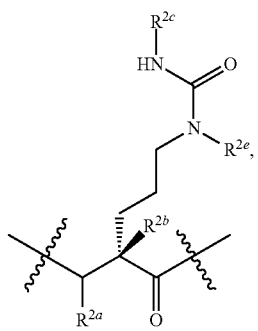

-continued
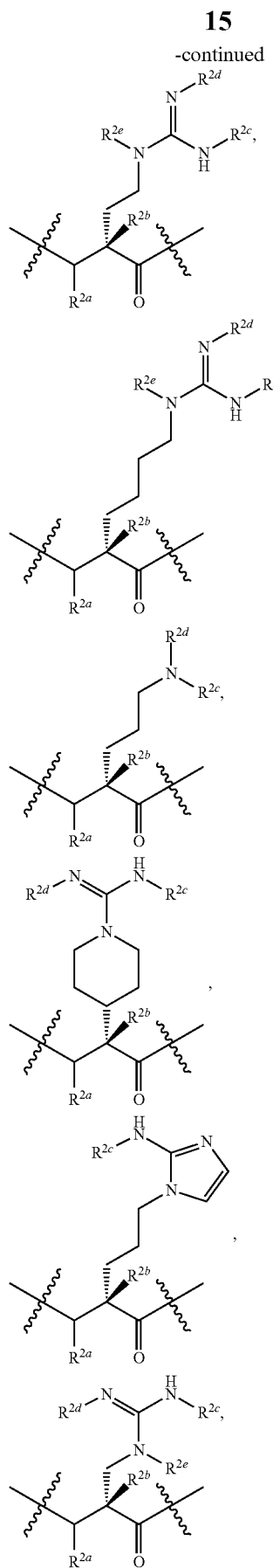
-continued
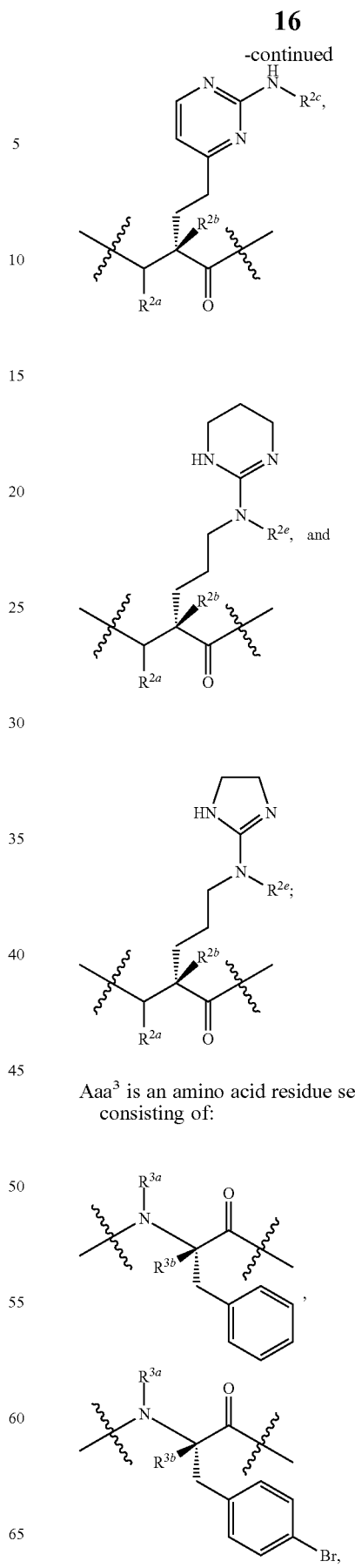
Aaa³ is an amino acid residue selected from the group consisting of:

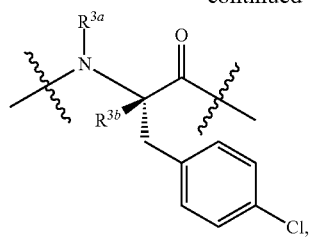
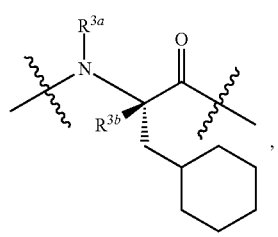
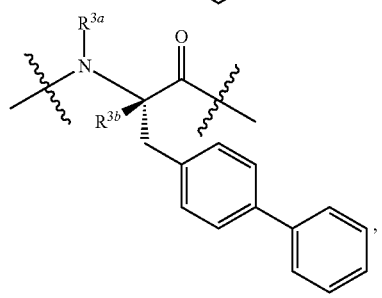
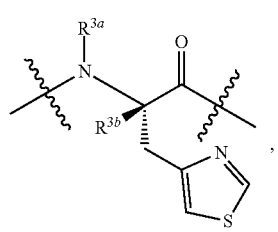
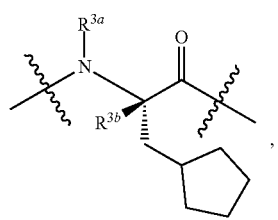
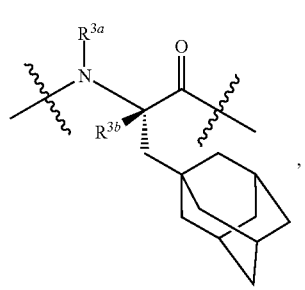
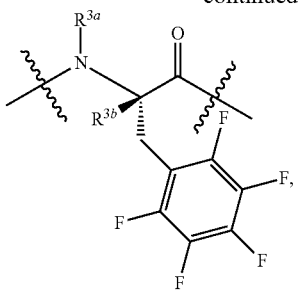
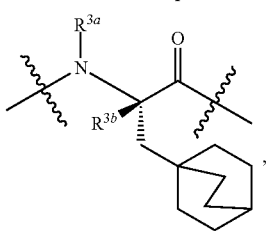
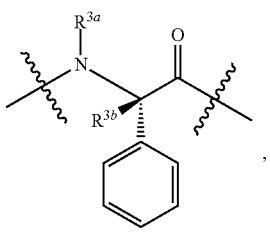
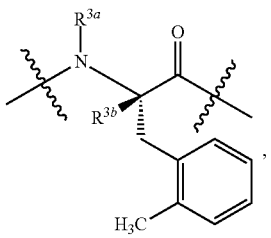
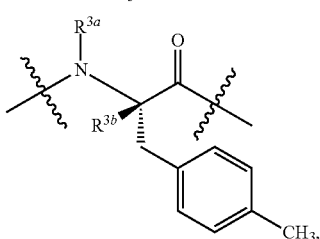
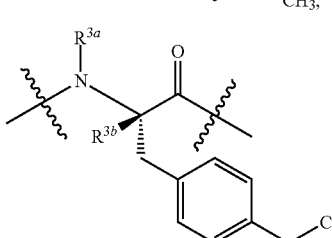
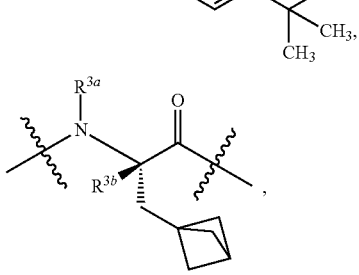

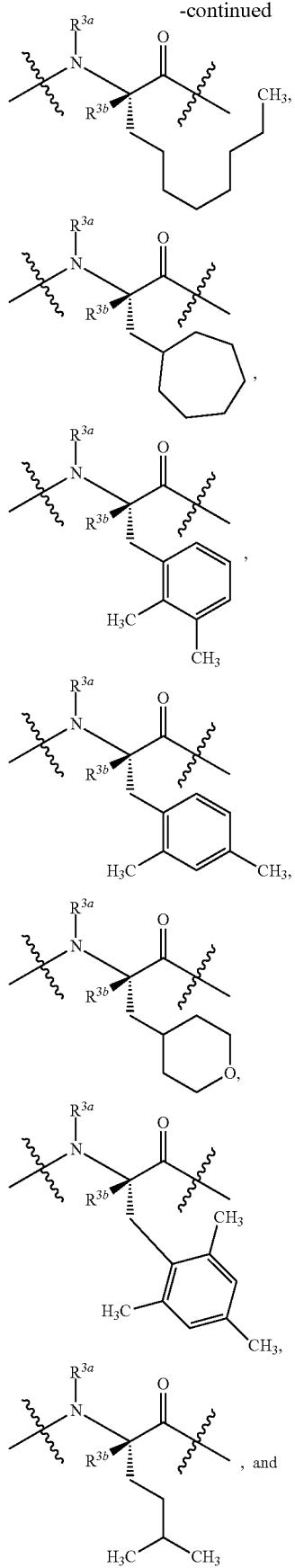
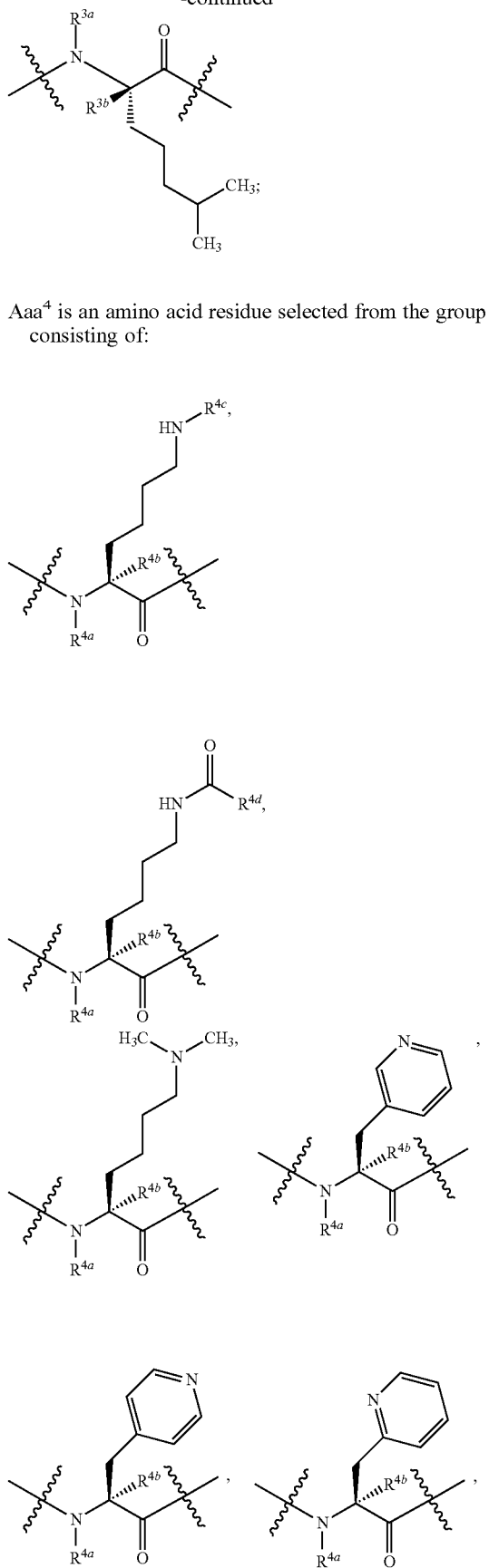
Aaa[4] is an amino acid residue selected from the group consisting of:

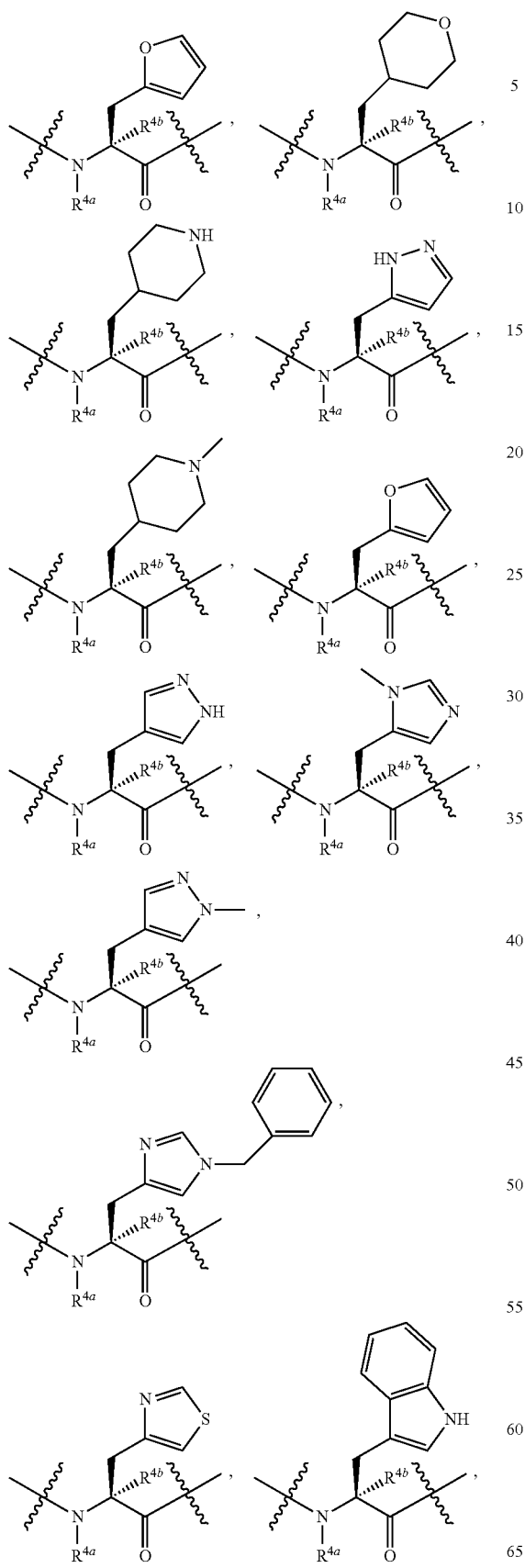
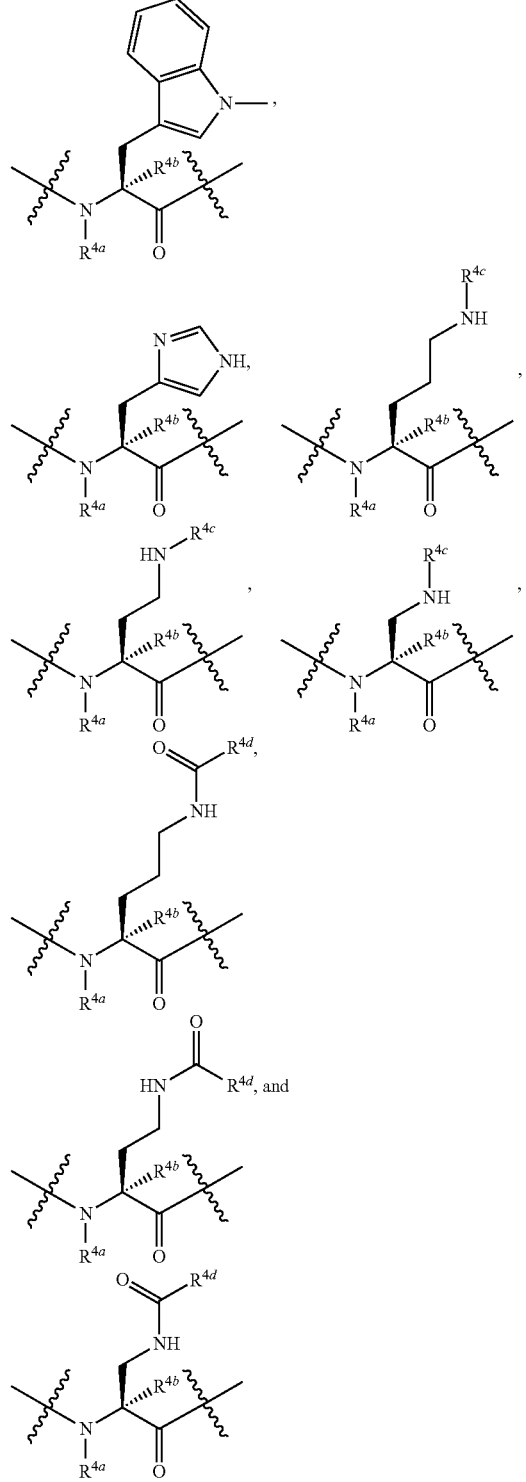
$R^{1a}$ and $R^{4d}$ are each independently $(C_1-C_6)$alkyl;
$R^{2a}$, $R^{2b}$, $R^{2c}$, $R^{3a}$, $R^{3b}$, $R^{4a}$, $R^{4b}$, $R^{4c}$ are each independently selected from the group consisting of H and $(C_1-C_6)$alkyl; and
$R^a$, $R^b$, $R^{2c}$, and $R^{2d}$ are each independently selected from the group consisting of H, $(C_1-C_6)$alkyl, C(O)$((C_1-C_6)$alkyl), C(O)$((C_1-C_6)$haloalkyl), C(O)O$((C_1-C_6)$alkyl), and C(O)O(aryl$(C_1-C_6)$alkyl); and provided that the compound of formula (I) is not
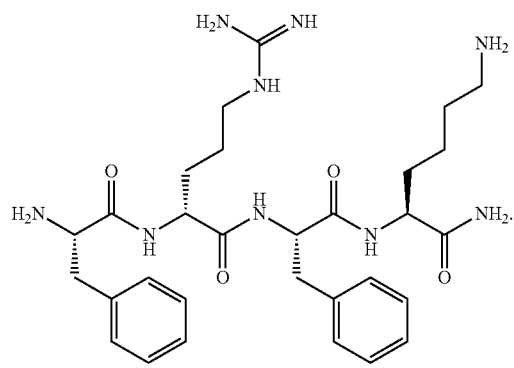 [SMILES: N=C(N)NCCC[C@@H](NC(=O)[C@@H](N)Cc1ccccc1)C(=O)N[C@@H](Cc1ccccc1)C(=O)N[C@@H](CCCCN)C(N)=O]
In certain embodiments, Aaa¹ is selected from the group consisting of:
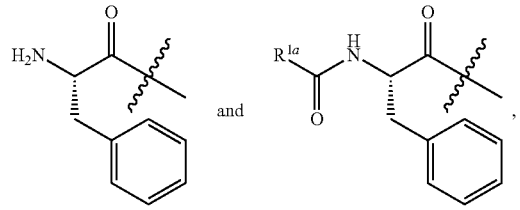
preferably
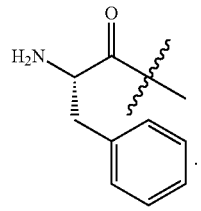 [SMILES: *C(=O)[C@@H](N)Cc1ccccc1]
In further embodiments, Aaa¹ is an amino acid residue selected from the group consisting of:
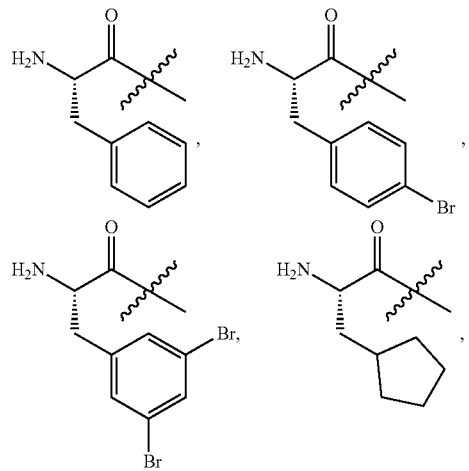
-continued
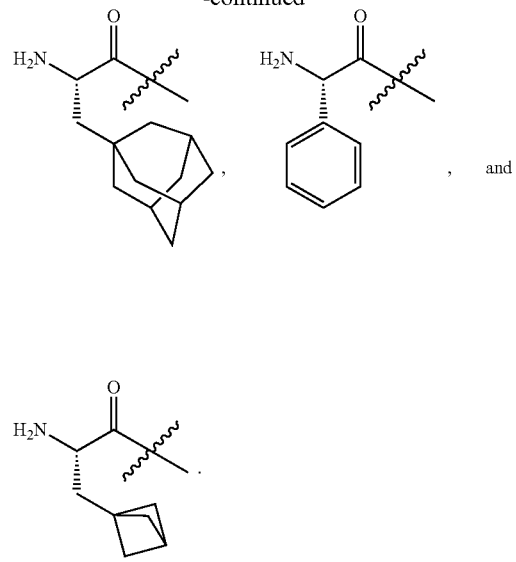
In certain embodiments, Aaa² is an amino acid residue selected from the group consisting of:
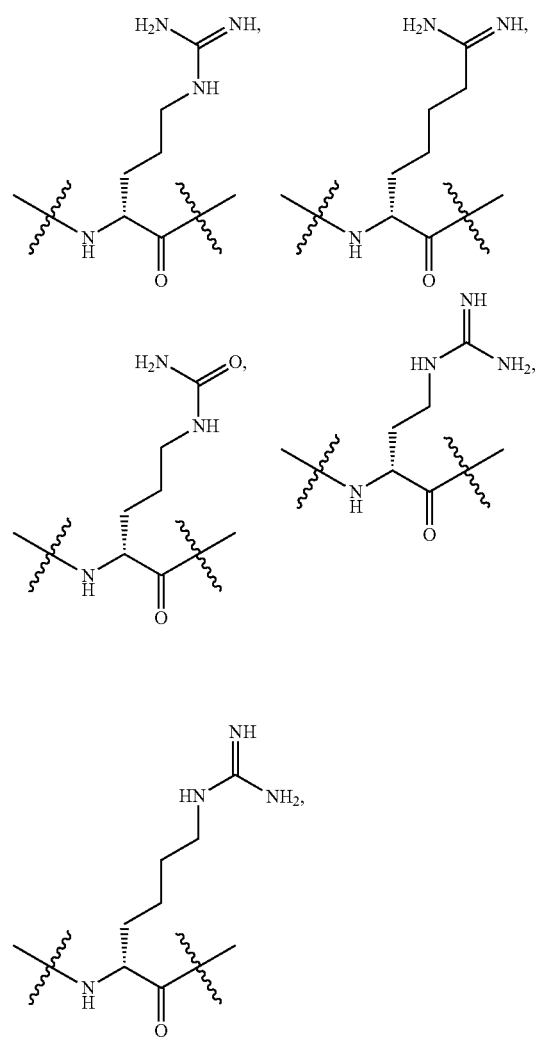

-continued
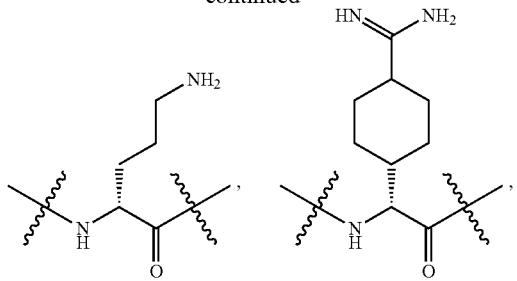
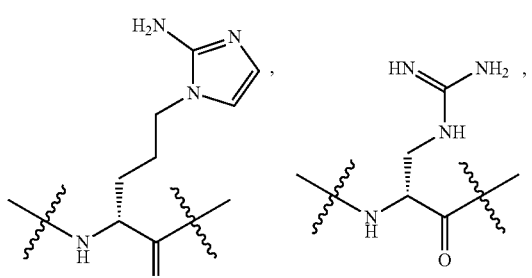
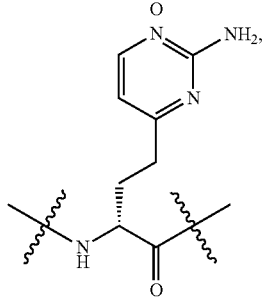
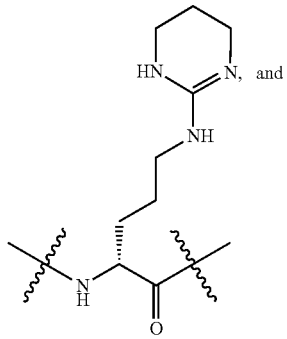, and
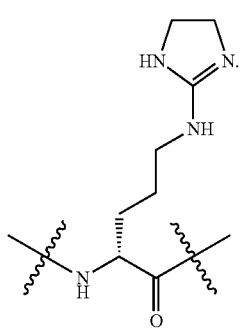
In some preferred embodiments, Aaa$^2$ is
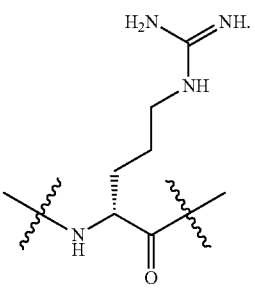 [SMILES: *N[C@H](CCCNC(=N)N)C(*)=O]
In certain embodiments, Aaa$^3$ is selected from the group consisting of:
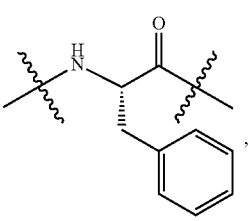,
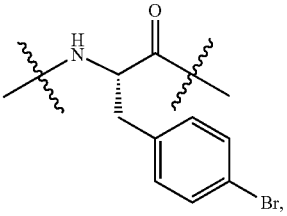,
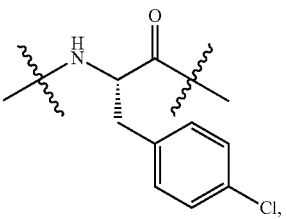,

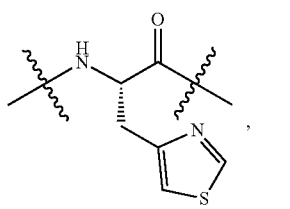
,
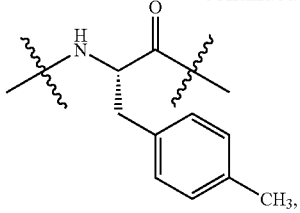
,
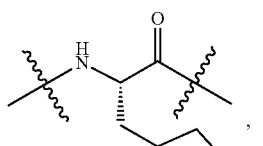
,
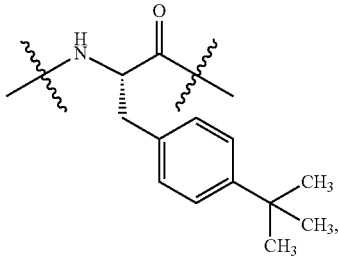
,
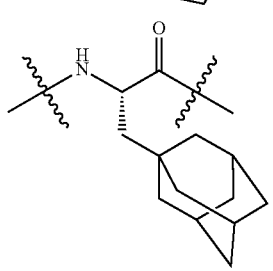
,
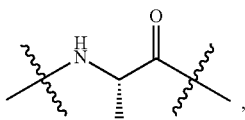
,
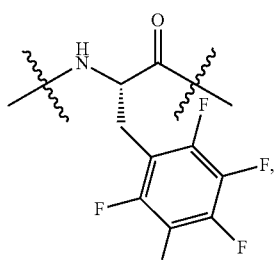
,
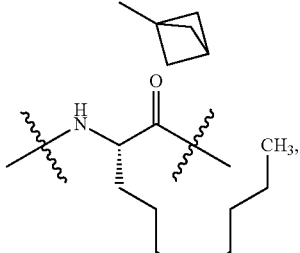
,
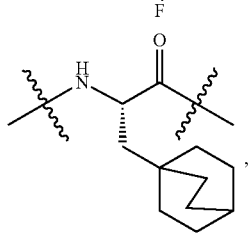
,
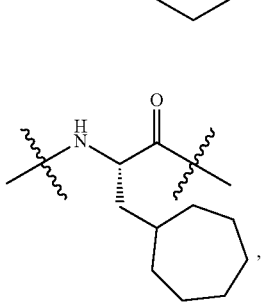
,
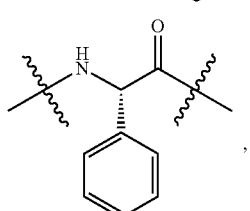
,
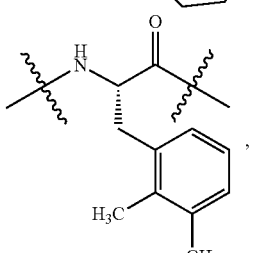
,
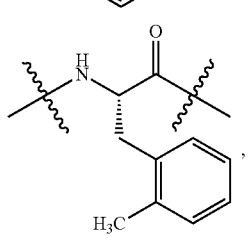
,
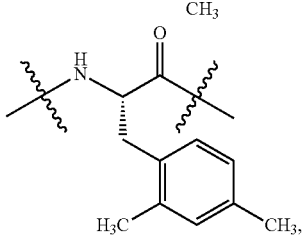
, -continued
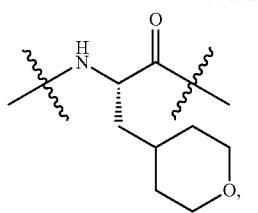
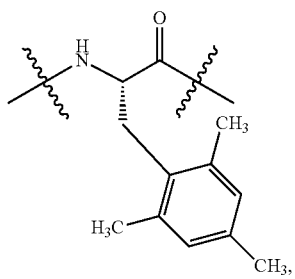
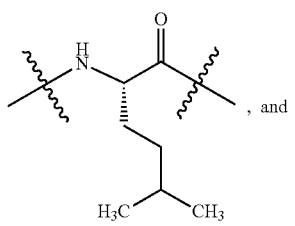, and
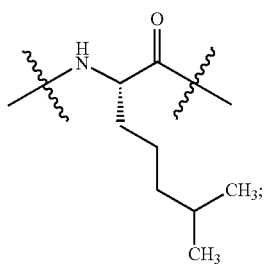;
In certain embodiments, Aaa³ is selected from the group consisting of:
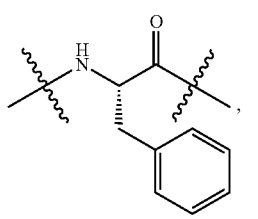,
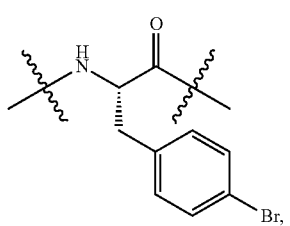,
-continued
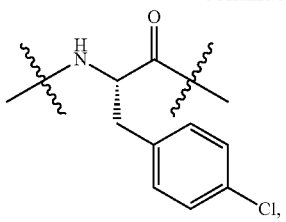,
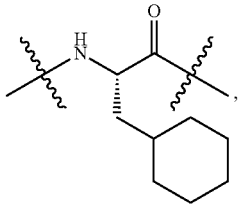,
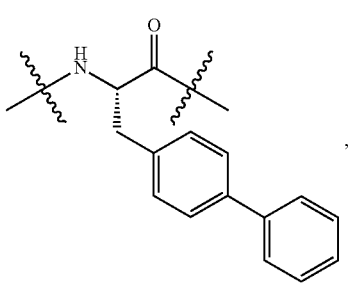,
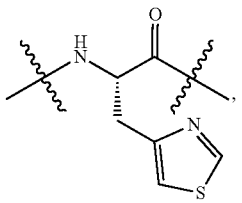,
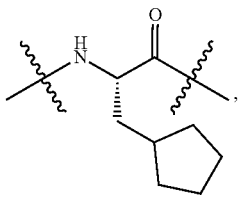,
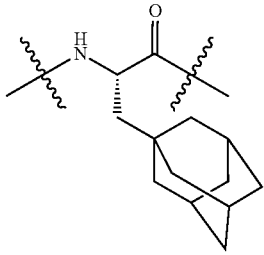,
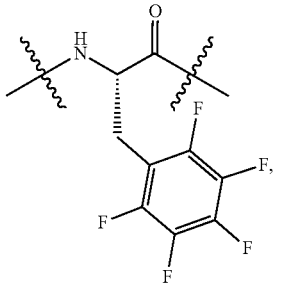,

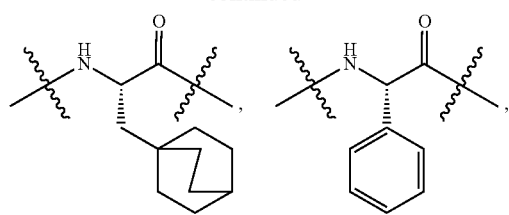
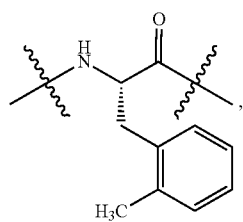
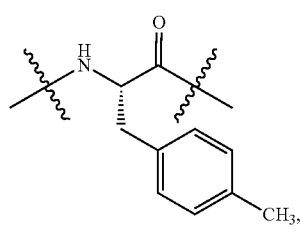
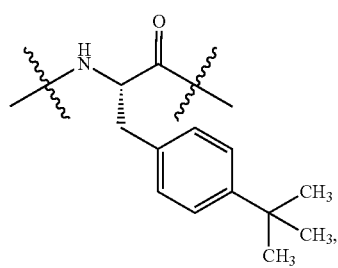
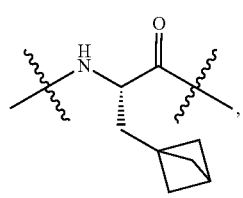
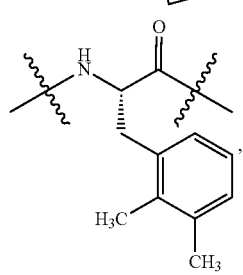
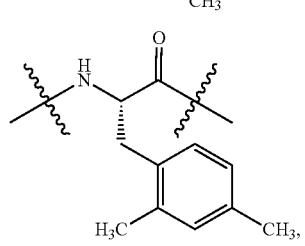
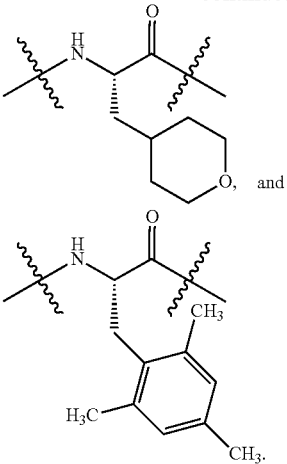
In certain other embodiments, Aaa³ is selected from the group consisting of:
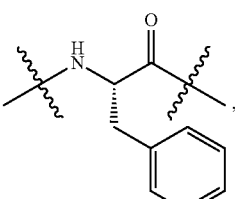
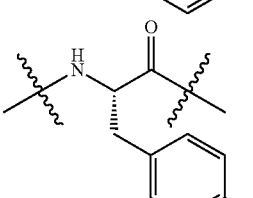
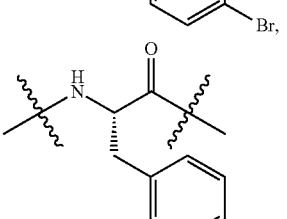
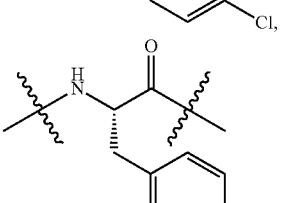
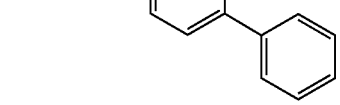
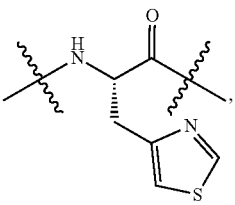

-continued
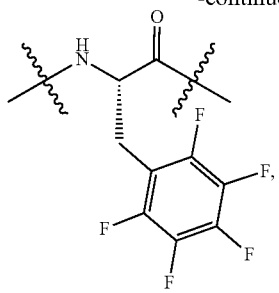
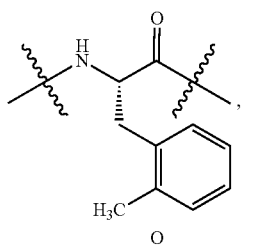
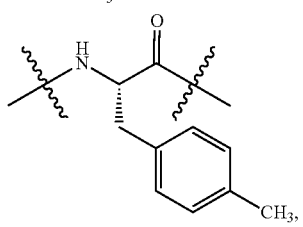
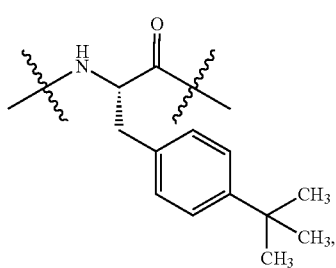
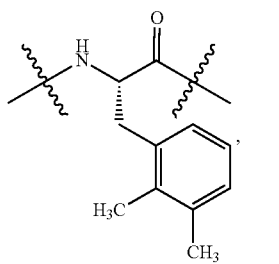
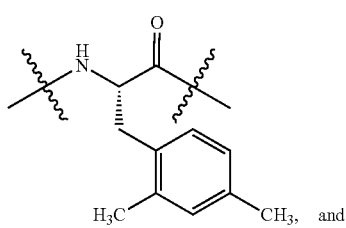 and
-continued
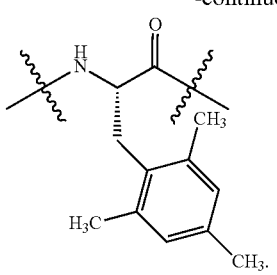
In certain embodiments, Aaa⁴ is selected from the group consisting of:
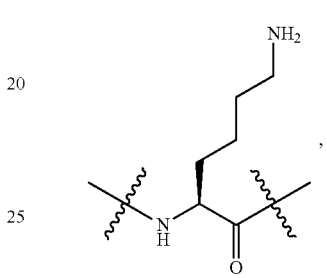
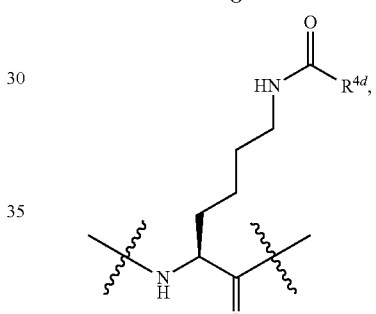
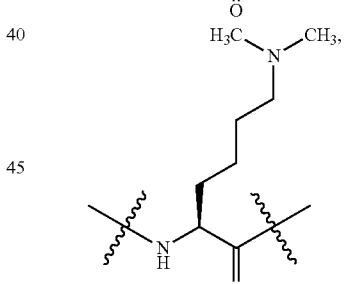
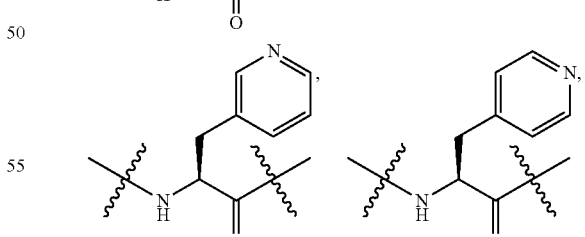
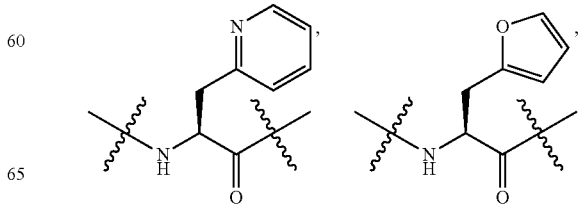

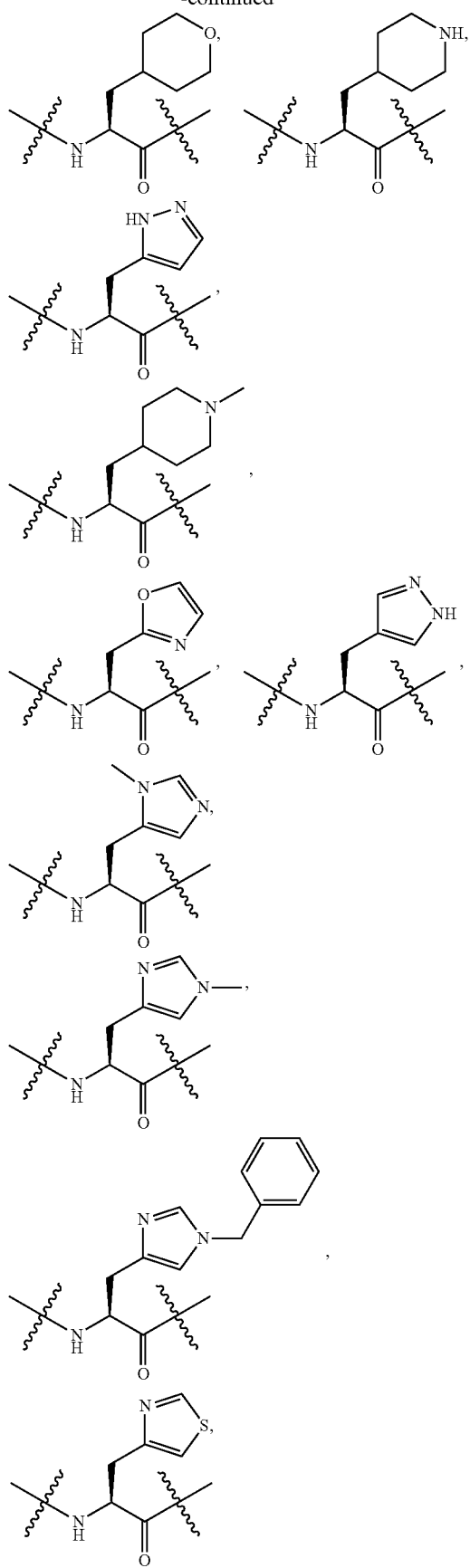
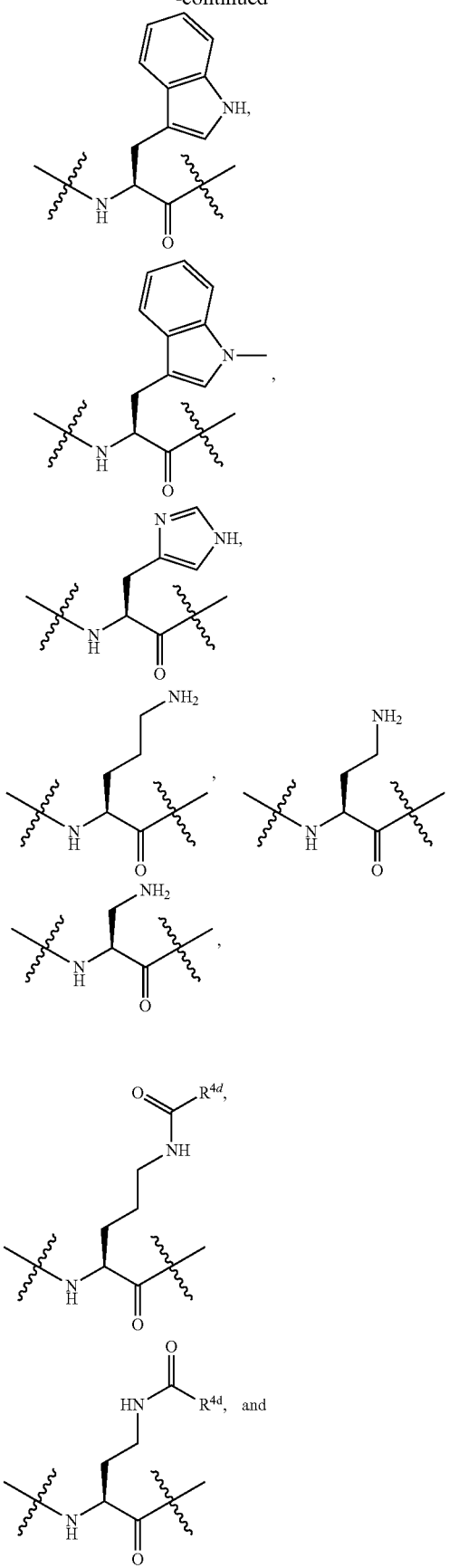

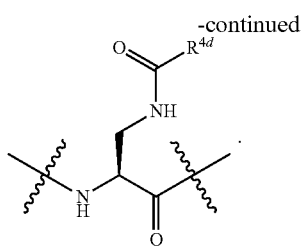
In still further embodiments, Aaa⁴ is selected from the group consisting of:
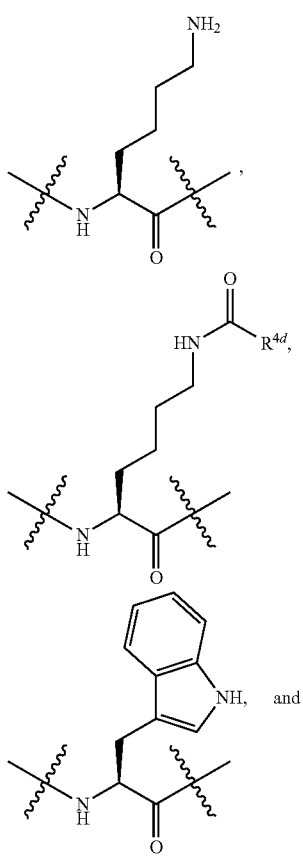
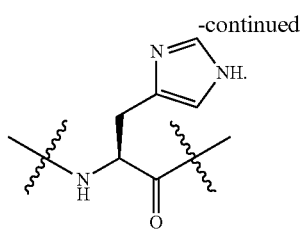
In certain embodiments, Aaa⁴ is selected from the group consisting of:
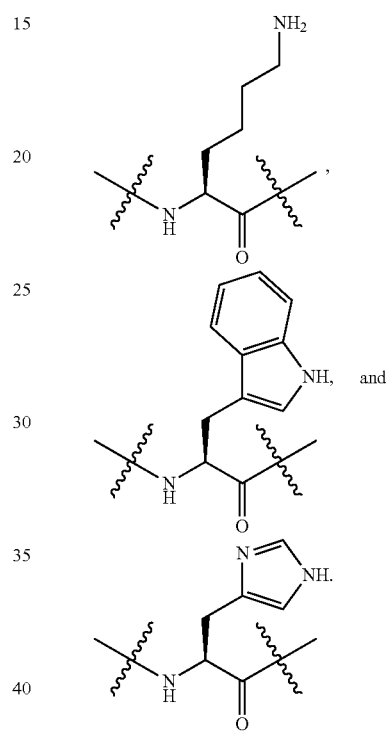
In certain embodiments, $R^a$ and $R^b$ are each independently H or methyl, preferably H.
In some embodiments, the compound of formula (I) is selected from the following table:
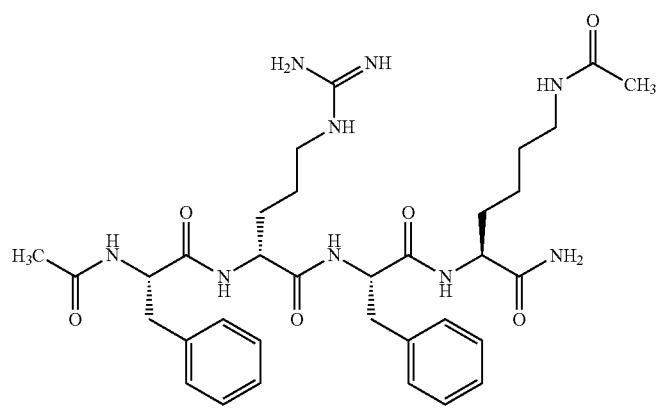 [SMILES: CC(=O)NCCCC[C@H](NC(=O)[C@H](Cc1ccccc1)NC(=O)[C@@H](CCCNC(=N)N)NC(=O)[C@H](Cc1ccccc1)NC(C)=O)C(N)=O]

-continued
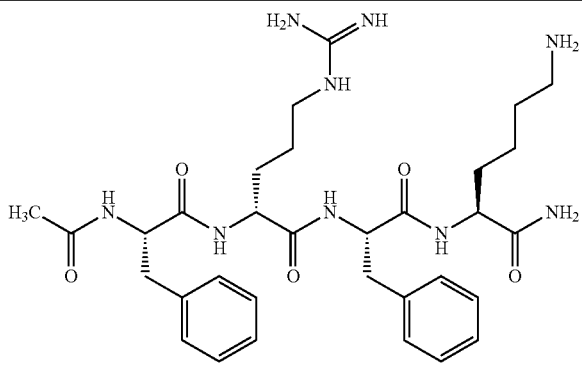
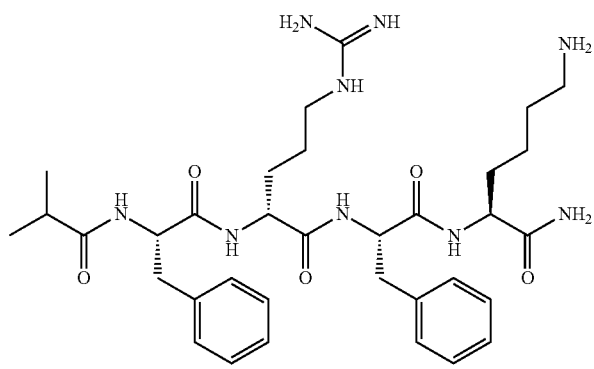 [SMILES: CC(C)C(=O)N[C@@H](Cc1ccccc1)C(=O)N[C@H](CCCNC(=N)N)C(=O)N[C@@H](Cc1ccccc1)C(=O)N[C@@H](CCCCN)C(N)=O]
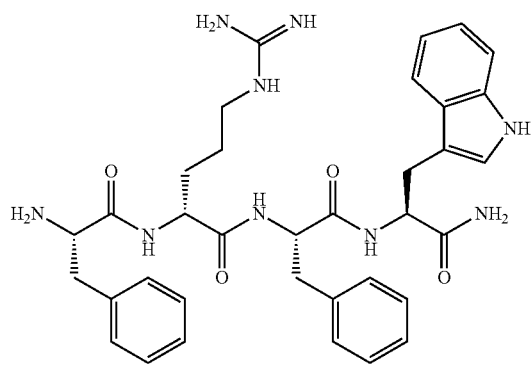 [SMILES: N=C(N)NCCC[C@@H](NC(=O)[C@@H](N)Cc1ccccc1)C(=O)N[C@@H](Cc1ccccc1)C(=O)N[C@@H](Cc1c[nH]c2ccccc12)C(N)=O]
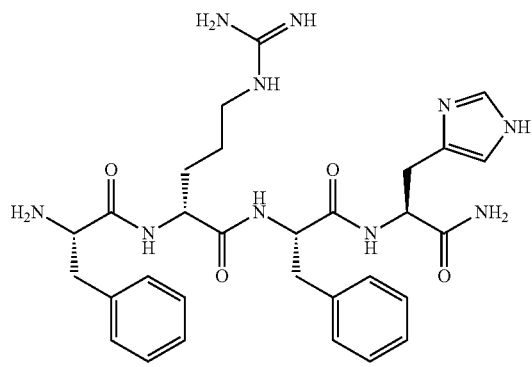 [SMILES: N=C(N)NCCC[C@@H](NC(=O)[C@@H](N)Cc1ccccc1)C(=O)N[C@@H](Cc1ccccc1)C(=O)N[C@@H](Cc1c[nH]cn1)C(N)=O]

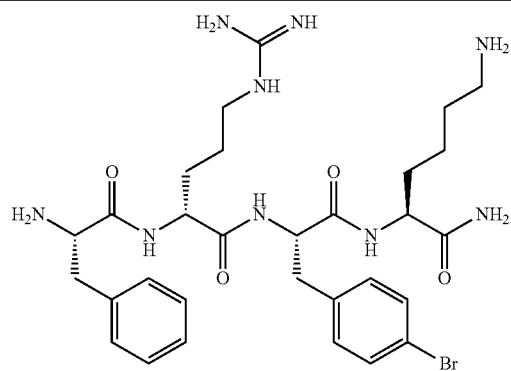
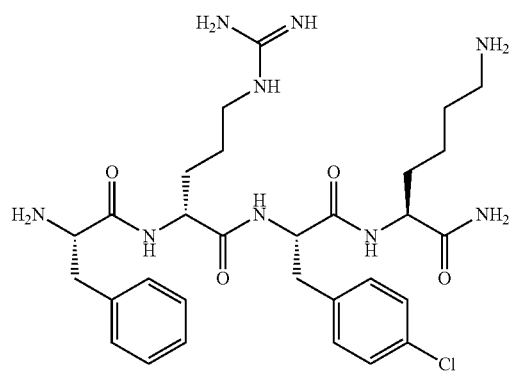 [SMILES: N=C(N)NCCC[C@@H](NC(=O)[C@@H](N)Cc1ccccc1)C(=O)N[C@@H](Cc1ccc(Cl)cc1)C(=O)N[C@@H](CCCCN)C(N)=O]
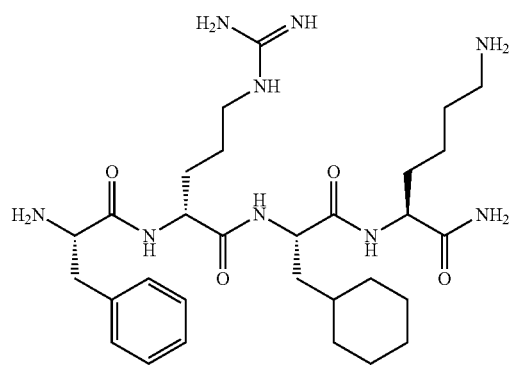 [SMILES: N=C(N)NCCC[C@@H](NC(=O)[C@@H](N)Cc1ccccc1)C(=O)N[C@@H](CC1CCCCC1)C(=O)N[C@@H](CCCCN)C(N)=O]
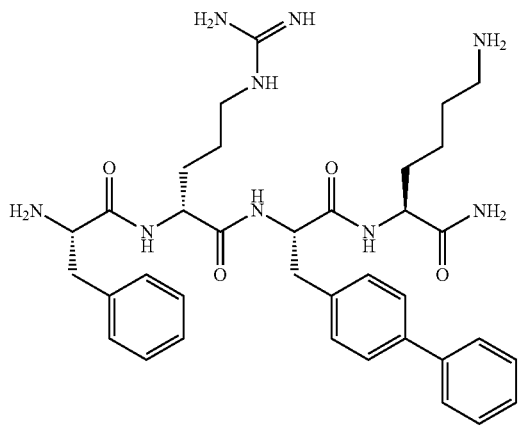 [SMILES: N=C(N)NCCC[C@@H](NC(=O)[C@@H](N)Cc1ccccc1)C(=O)N[C@@H](Cc1ccc(-c2ccccc2)cc1)C(=O)N[C@@H](CCCCN)C(N)=O]

-continued
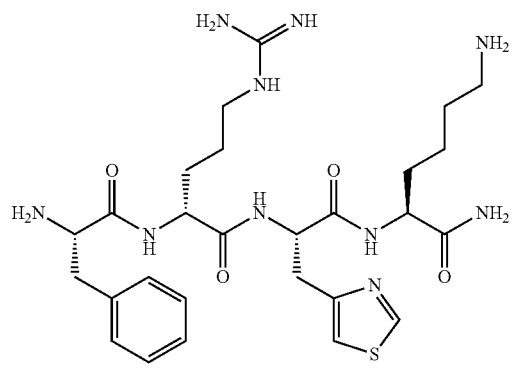 [SMILES: N=C(N)NCCC[C@@H](NC(=O)[C@@H](N)Cc1ccccc1)C(=O)N[C@@H](Cc1cscn1)C(=O)N[C@@H](CCCCN)C(N)=O]
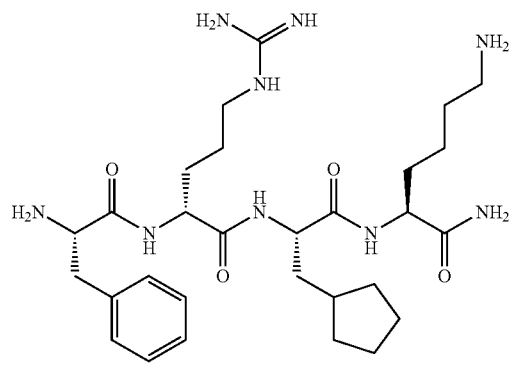 [SMILES: N=C(N)NCCC[C@@H](NC(=O)[C@@H](N)Cc1ccccc1)C(=O)N[C@@H](CC1CCCC1)C(=O)N[C@@H](CCCCN)C(N)=O]
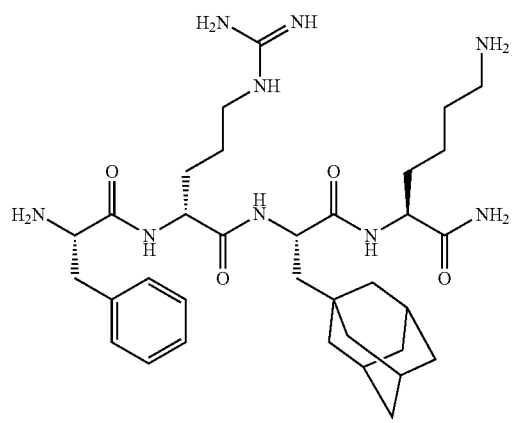 [SMILES: N=C(N)NCCC[C@@H](NC(=O)[C@@H](N)Cc1ccccc1)C(=O)N[C@@H](CC12CC3CC(CC(C3)C1)C2)C(=O)N[C@@H](CCCCN)C(N)=O]
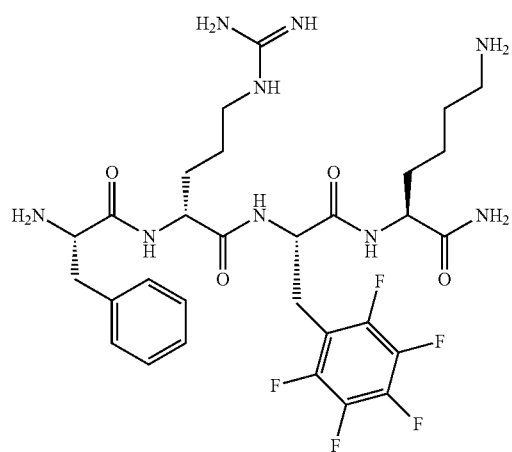 [SMILES: N=C(N)NCCC[C@@H](NC(=O)[C@@H](N)Cc1ccccc1)C(=O)N[C@@H](Cc1c(F)c(F)c(F)c(F)c1F)C(=O)N[C@@H](CCCCN)C(N)=O]

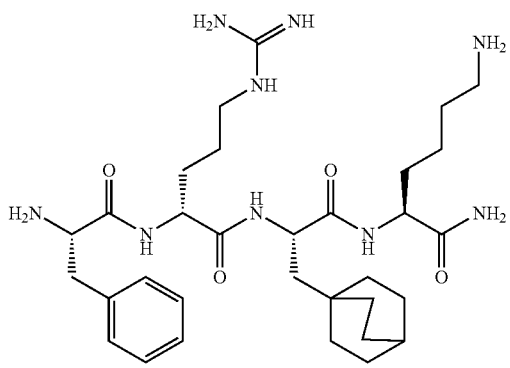 [SMILES: N=C(N)NCCC[C@@H](NC(=O)[C@@H](N)Cc1ccccc1)C(=O)N[C@@H](CC12CCC(CC1)CC2)C(=O)N[C@@H](CCCCN)C(N)=O]
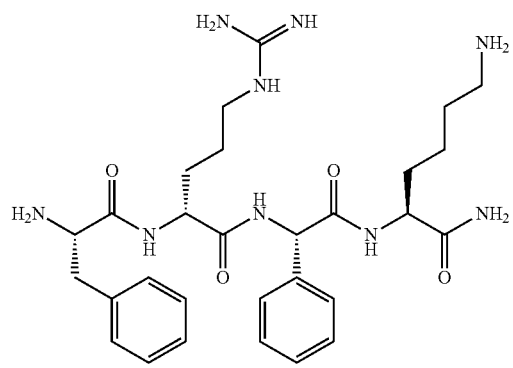 [SMILES: N=C(N)NCCC[C@@H](NC(=O)[C@@H](N)Cc1ccccc1)C(=O)N[C@H](C(=O)N[C@@H](CCCCN)C(N)=O)c1ccccc1]
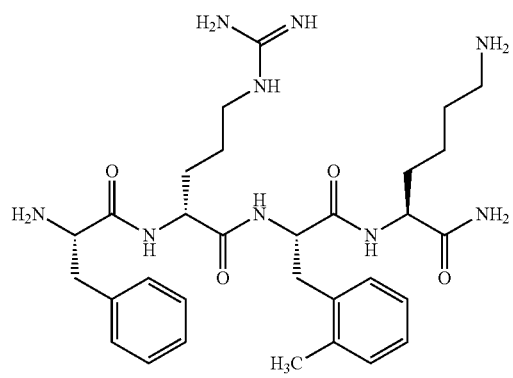 [SMILES: Cc1ccccc1C[C@H](NC(=O)[C@@H](CCCNC(=N)N)NC(=O)[C@@H](N)Cc1ccccc1)C(=O)N[C@@H](CCCCN)C(N)=O]
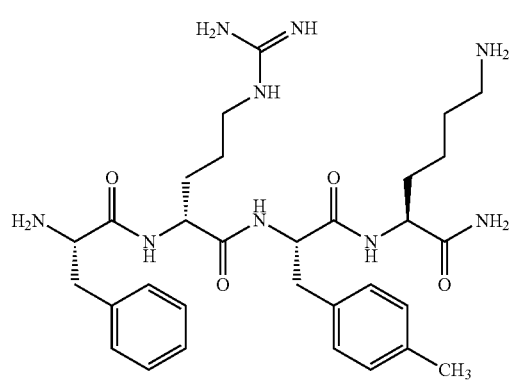 [SMILES: Cc1ccc(C[C@H](NC(=O)[C@@H](CCCNC(=N)N)NC(=O)[C@@H](N)Cc2ccccc2)C(=O)N[C@@H](CCCCN)C(N)=O)cc1]

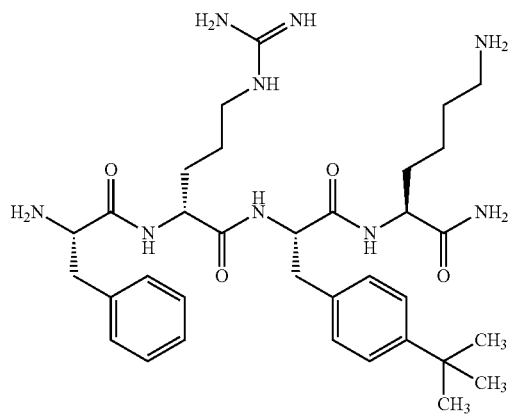 [SMILES: CC(C)(C)c1ccc(C[C@H](NC(=O)[C@@H](CCCNC(=N)N)NC(=O)[C@@H](N)Cc2ccccc2)C(=O)N[C@@H](CCCCN)C(N)=O)cc1]
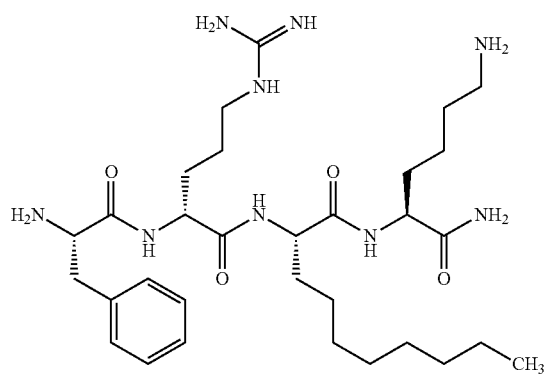 [SMILES: CCCCCCCC[C@H](NC(=O)[C@@H](CCCNC(=N)N)NC(=O)[C@@H](N)Cc1ccccc1)C(=O)N[C@@H](CCCCN)C(N)=O]
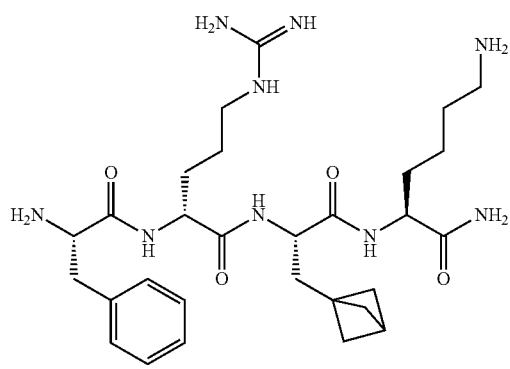 [SMILES: N=C(N)NCCC[C@@H](NC(=O)[C@@H](N)Cc1ccccc1)C(=O)N[C@@H](CC12CC(C1)C2)C(=O)N[C@@H](CCCCN)C(N)=O]
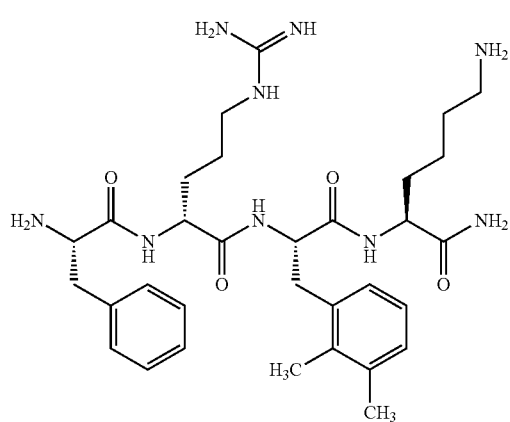 [SMILES: Cc1cccc(C[C@H](NC(=O)[C@@H](CCCNC(=N)N)NC(=O)[C@@H](N)Cc2ccccc2)C(=O)N[C@@H](CCCCN)C(N)=O)c1C]

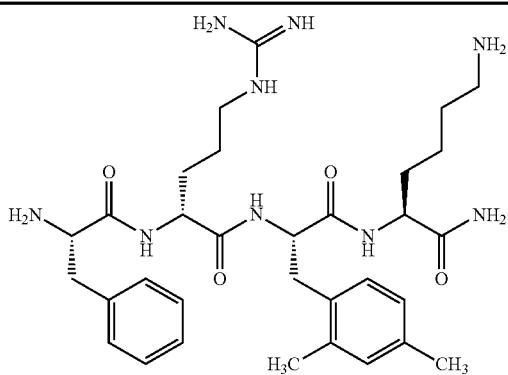
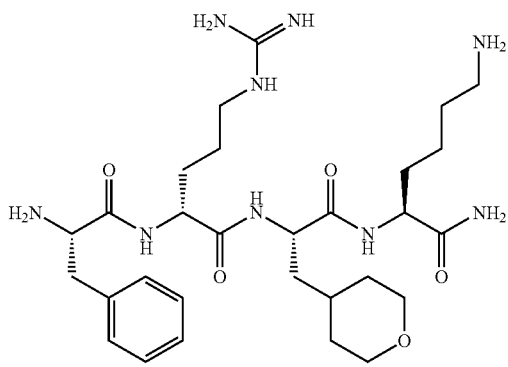 [SMILES: N=C(N)NCCC[C@@H](NC(=O)[C@@H](N)Cc1ccccc1)C(=O)N[C@@H](CC1CCOCC1)C(=O)N[C@@H](CCCCN)C(N)=O]
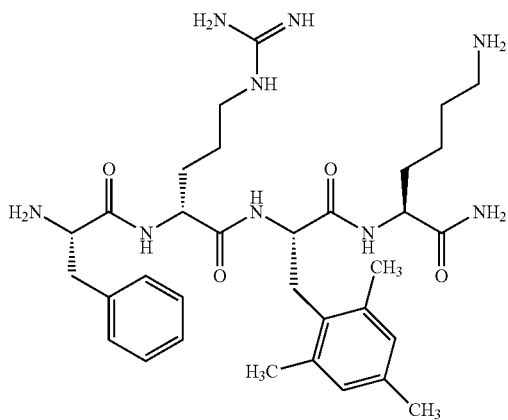 [SMILES: Cc1cc(C)c(C[C@H](NC(=O)[C@@H](CCCNC(=N)N)NC(=O)[C@@H](N)Cc2ccccc2)C(=O)N[C@@H](CCCCN)C(N)=O)c(C)c1]
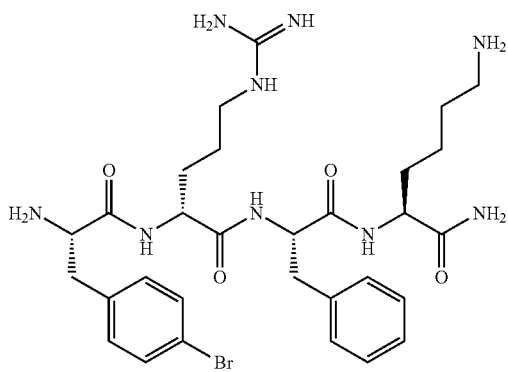 [SMILES: N=C(N)NCCC[C@@H](NC(=O)[C@@H](N)Cc1ccc(Br)cc1)C(=O)N[C@@H](Cc1ccccc1)C(=O)N[C@@H](CCCCN)C(N)=O]

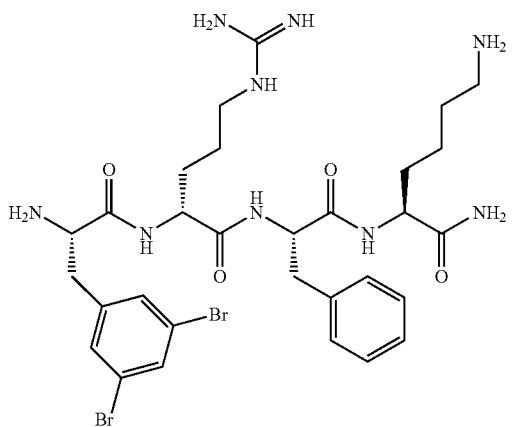 [SMILES: N=C(N)NCCC[C@@H](NC(=O)[C@@H](N)Cc1cc(Br)cc(Br)c1)C(=O)N[C@@H](Cc1ccccc1)C(=O)N[C@@H](CCCCN)C(N)=O]
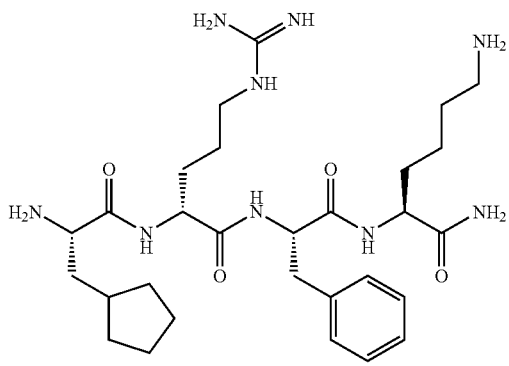 [SMILES: N=C(N)NCCC[C@@H](NC(=O)[C@@H](N)CC1CCCC1)C(=O)N[C@@H](Cc1ccccc1)C(=O)N[C@@H](CCCCN)C(N)=O]
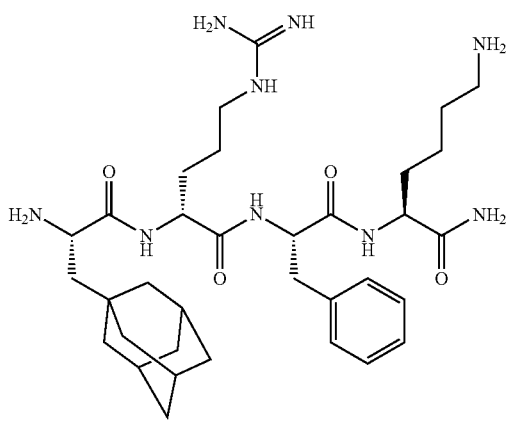 [SMILES: N=C(N)NCCC[C@@H](NC(=O)[C@@H](N)CC12CC3CC(CC(C3)C1)C2)C(=O)N[C@@H](Cc1ccccc1)C(=O)N[C@@H](CCCCN)C(N)=O]
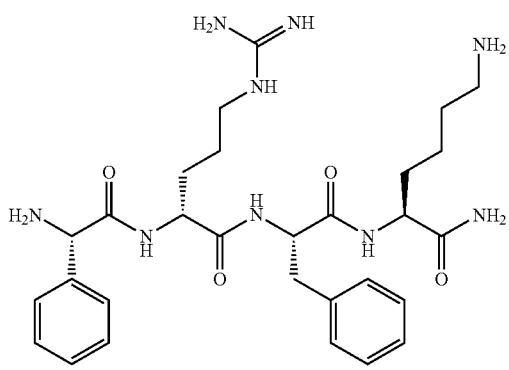 [SMILES: N=C(N)NCCC[C@@H](NC(=O)[C@@H](N)c1ccccc1)C(=O)N[C@@H](Cc1ccccc1)C(=O)N[C@@H](CCCCN)C(N)=O]

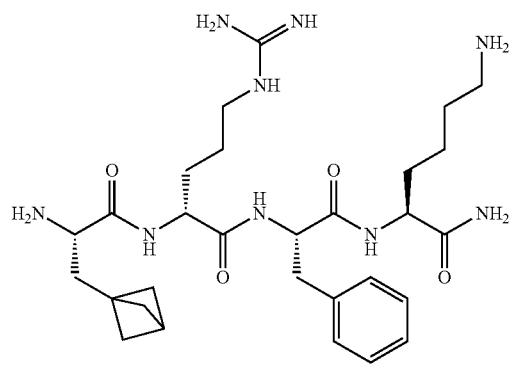 [SMILES: N=C(N)NCCC[C@@H](NC(=O)[C@@H](N)CC12CC(C1)C2)C(=O)N[C@@H](Cc1ccccc1)C(=O)N[C@@H](CCCCN)C(N)=O]
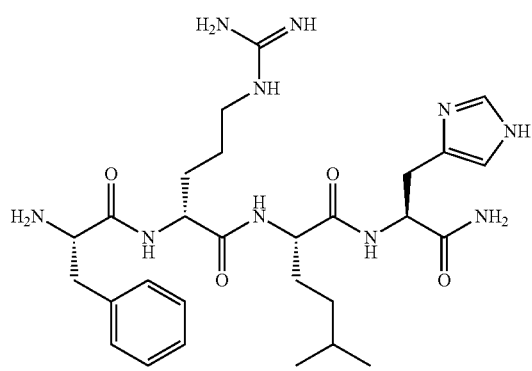 [SMILES: CC(C)CC[C@H](NC(=O)[C@@H](CCCNC(=N)N)NC(=O)[C@@H](N)Cc1ccccc1)C(=O)N[C@@H](Cc1c[nH]cn1)C(N)=O]
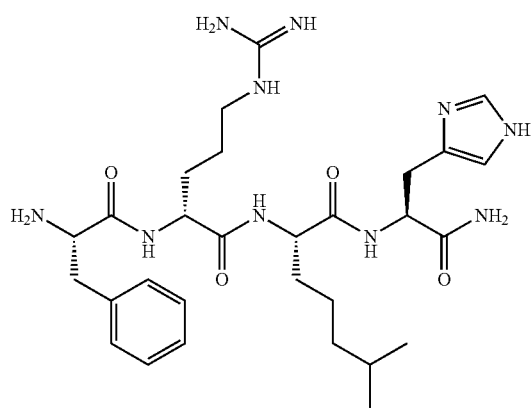 [SMILES: CC(C)CCC[C@H](NC(=O)[C@@H](CCCNC(=N)N)NC(=O)[C@@H](N)Cc1ccccc1)C(=O)N[C@@H](Cc1c[nH]cn1)C(N)=O]
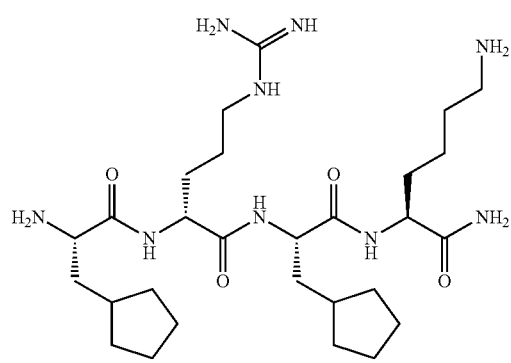 [SMILES: N=C(N)NCCC[C@@H](NC(=O)[C@@H](N)CC1CCCC1)C(=O)N[C@@H](CC1CCCC1)C(=O)N[C@@H](CCCCN)C(N)=O]

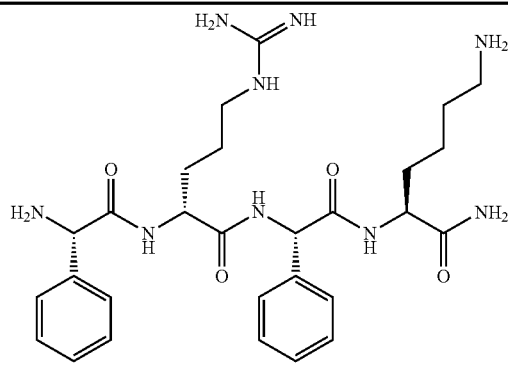

Peptide Synthesis

The peptidic compounds of the invention may be prepared using a peptide synthesis method, such as conventional liquid-phase peptide synthesis or solid-phase peptide synthesis, or by peptide synthesis by means of an automated peptide synthesizer (Kelley et al., Genetics Engineering Principles and Methods, Setlow, J. K. eds., Plenum Press NY. (1990) Vol. 12, pp. 1 to 19; Stewart et al., Solid-Phase Peptide Synthesis (1989) W. H.; Houghten, Proc. Natl. Acad. Sci. USA (1985) 82: p. 5132). The peptide thus produced can be collected or purified by a routine method, for example, chromatography, such as gel filtration chromatography, ion exchange column chromatography, affinity chromatography, reverse phase column chromatography, and HPLC, ammonium sulfate fractionation, ultrafiltration, and immunoadsorption.

In a solid-phase peptide synthesis, peptides are typically synthesized from the carbonyl group side (C-terminus) to amino group side (N-terminus) of the amino acid chain. In certain embodiments, an amino-protected amino acid is covalently bound to a solid support material through the carboxyl group of the amino acid, typically via an ester or amido bond and optionally via a linking group. The amino group may be deprotected and reacted with (i.e., "coupled" with) the carbonyl group of a second amino-protected amino acid using a coupling reagent, yielding a dipeptide bound to a solid support. These steps (i.e., deprotection, coupling) may be repeated to form the desired peptide chain. Once the desired peptide chain is complete, the peptide may be cleaved from the solid support.

In certain embodiments, the protecting groups used on the amino groups of the amino acid residues include 9-fluorenylmethyloxycarbonyl group (Fmoc) and t-butyloxycarbonyl (Boc). The Fmoc group is removed from the amino terminus with base while the Boc group is removed with acid. In alternative embodiments, the amino protecting group may be formyl, acrylyl (Acr), benzoyl (Bz), acetyl (Ac), trifluoroacetyl, substituted or unsubstituted groups of aralkyloxycarbonyl type, such as the benzyloxycarbonyl (Z), p-chlorobenzyloxycarbonyl, p-bromobenzyloxycarbonyl, p-nitrobenzyloxycarbonyl, p-methoxybenzyloxycarbonyl, benzhydryloxycarbonyl, 2(p-biphenylyl)isopropyloxycarbonyl, 2-(3,5-dimethoxyphenyl)isopropyloxycarbonyl, p-phenylazobenzyloxycarbonyl, triphenylphosphonoethyloxycarbonyl or 9-fluorenylmethyloxycarbonyl group (Fmoc), substituted or unsubstituted groups of alkyloxycarbonyl type, such as the tert-butyloxycarbonyl (BOC), tert-amyloxycarbonyl, diisopropylmethyloxycarbonyl, isopropyloxycarbonyl, ethyloxycarbonyl, allyloxycarbonyl, 2 methylsulphonylethyloxycarbonyl or 2,2,2-trichloroethyloxycarbonyl group, groups of cycloalkyloxycarbonyl type, such as the cyclopentyloxycarbonyl, cyclohexyloxycarbonyl, adamantyloxycarbonyl or isobornyloxycarbonyl group, and groups containing a hetero atom, such as the benzenesulphonyl, p-toluenesulphonyl, mesitylenesulphonyl, methoxytrimethylphenylsulphonyl, 2-nitrobenzenesulfonyl, 2-nitrobenzenesulfenyl, 4-nitrobenzenesulfonyl or 4-nitrobenzenesulfenyl group.

Many amino acids bear reactive functional groups in the side chain. In certain embodiments, such functional groups are protected in order to prevent the functional groups from reacting with the incoming amino acid. The protecting groups used with these functional groups must be stable to the conditions of peptide synthesis, but may be removed before, after, or concomitantly with cleavage of the peptide from the solid support.

In certain embodiments, the solid support material used in the solid-phase peptide synthesis method is a gel-type support such as polystyrene, polyacrylamide, or polyethylene glycol. Alternatively, materials such as pore glass, cellulose fibers, or polystyrene may be functionalized at their surface to provide a solid support for peptide synthesis.

Coupling reagents that may be used in the solid-phase peptide synthesis described herein are typically carbodiimide reagents. Examples of carbodiimide reagents include, but are not limited to, N,N'-dicyclohexylcarbodiimide (DCC), 1-(3-dimethylaminopropyl)-3-ethylcarbodiimide (EDC), N-cyclohexyl-N'-isopropylcarbodiimide (CIC), N,N'-diisopropylcarbodiimide (DIC), N-tert-butyl-N'-methylcarbodiimide (BMC), N-tert-butyl-N'-ethylcarbodiimide (BEC), bis[[4-(2,2-dimethyl-1,3-dioxolyl)]-methyl]carbodiimide (BDDC), and N,N-dicyclopentylcarbodiimide. DCC is a preferred coupling reagent.

In certain embodiments, a compound of the invention, for example, the compound pictured below, is synthesized in a linear sequential fashion, according to the solid phase synthesis depicted in Scheme 1:

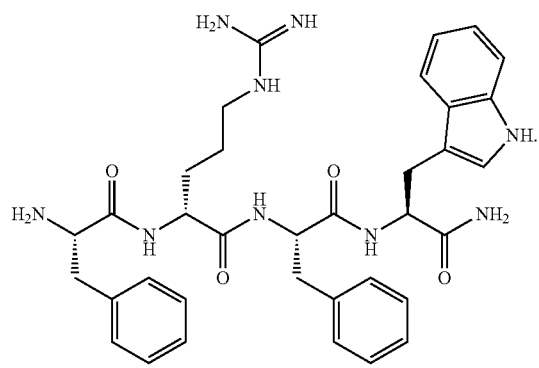

For reference in the following schemes,

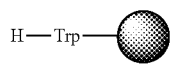

indicates

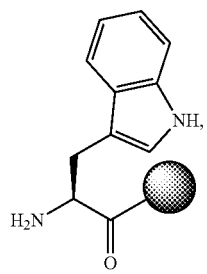

wherein

represents a solid support and optionally a linking group.

Scheme 1

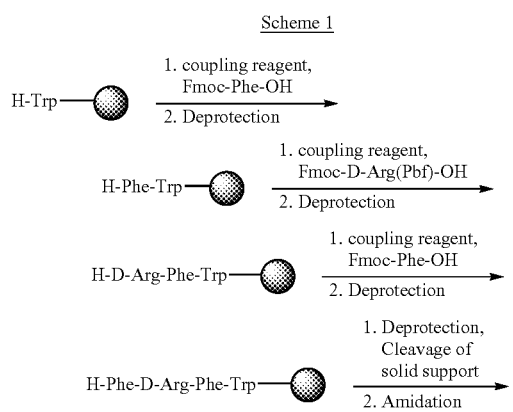

Alternatively, a compound of the invention may be synthesized in a convergent fashion, for example, according to Scheme 2:

Scheme 2

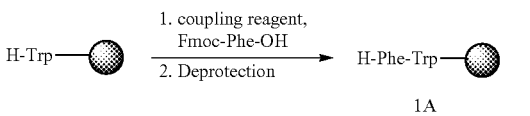

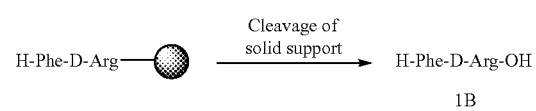

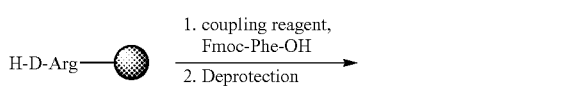

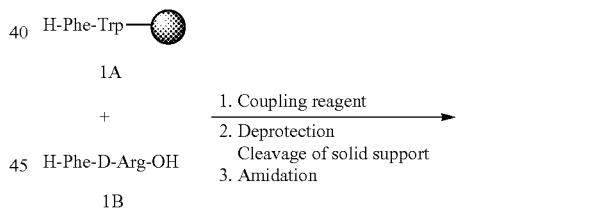

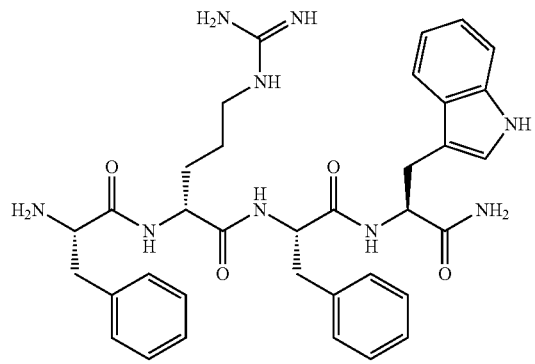 [SMILES: N=C(N)NCCC[C@@H](NC(=O)[C@@H](N)Cc1ccccc1)C(=O)N[C@@H](Cc1ccccc1)C(=O)N[C@@H](Cc1c[nH]c2ccccc12)C(N)=O]

The compounds of the invention may also be synthesized according to conventional liquid-phase peptide synthetic routes. For example, the compound pictured below may be synthesized in a convergent liquid-phase synthesis, as depicted in Scheme 3.

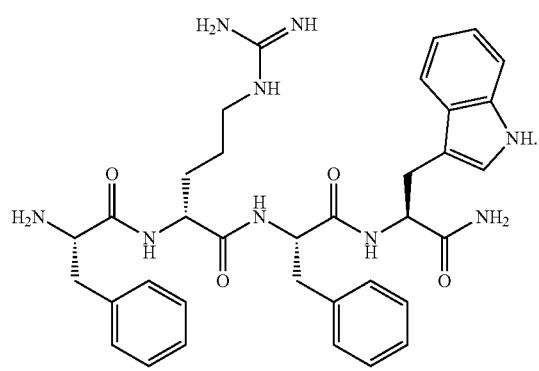
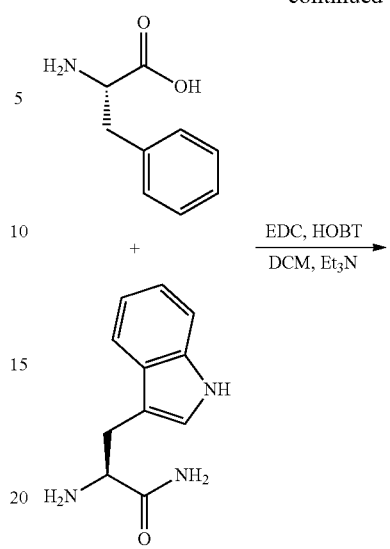
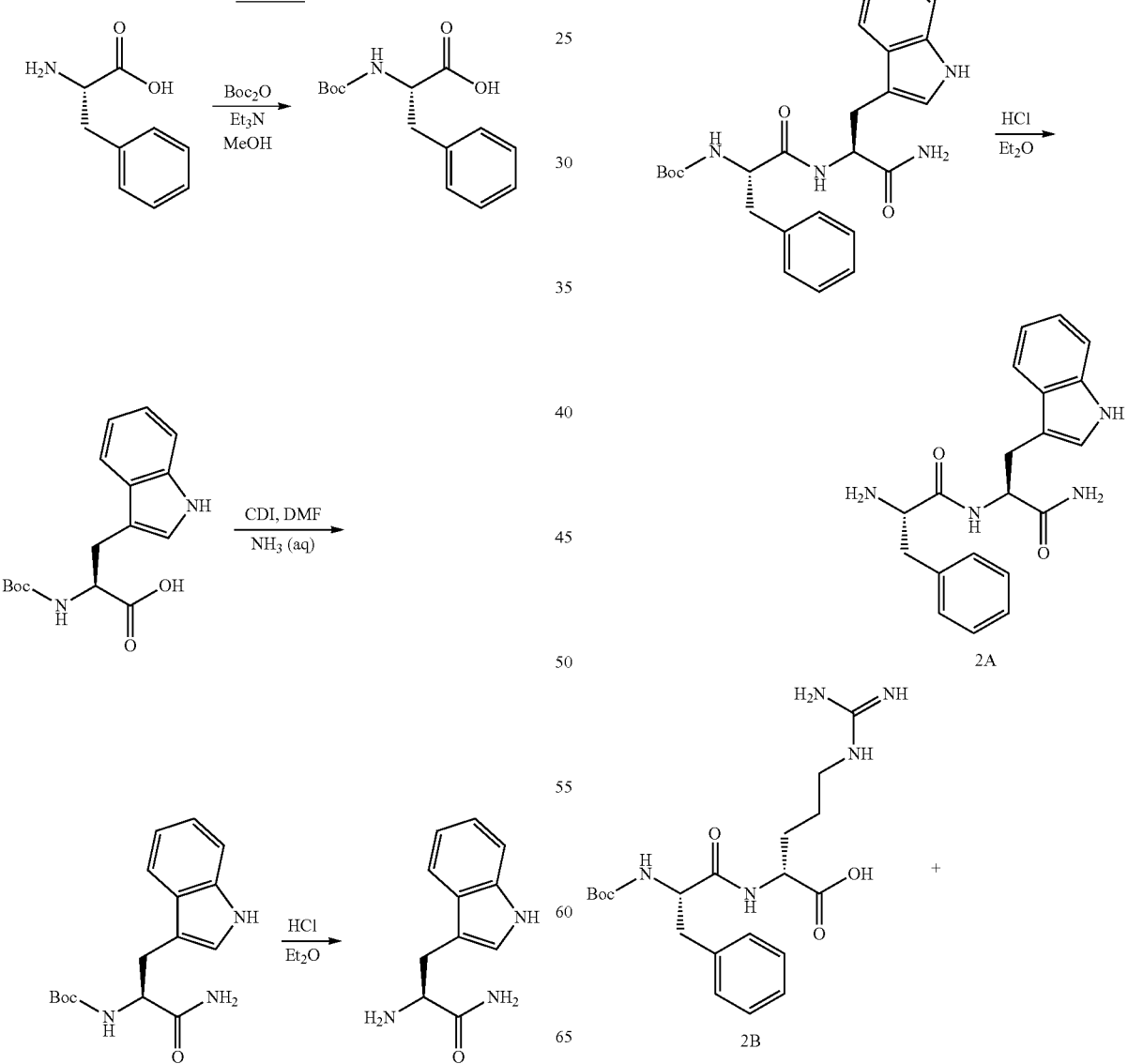
Scheme 3
2A
2B

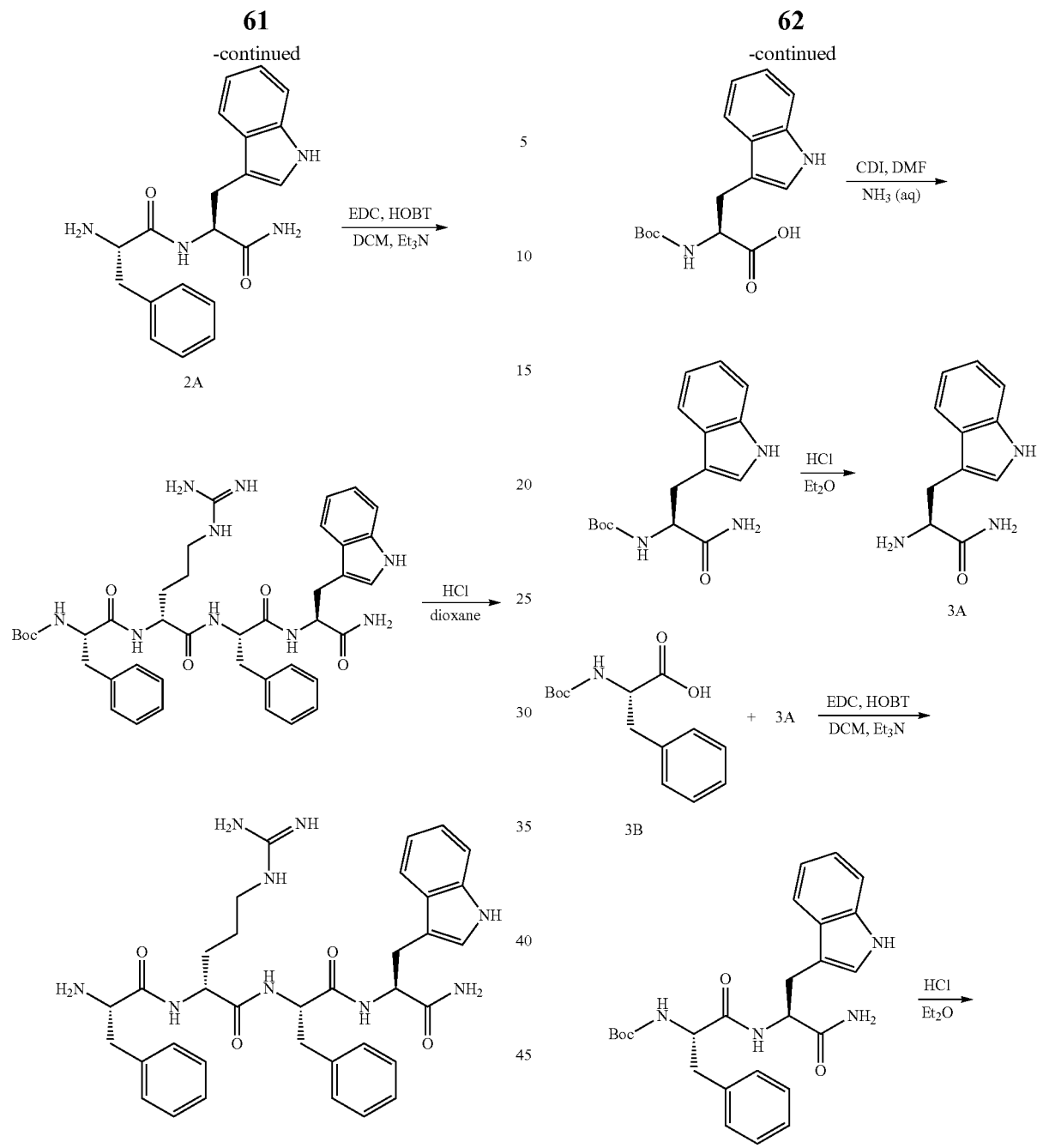
In another exemplary embodiment, a compound of the invention is made via the linear sequential liquid phase synthesis depicted in Scheme 4.
Scheme 4
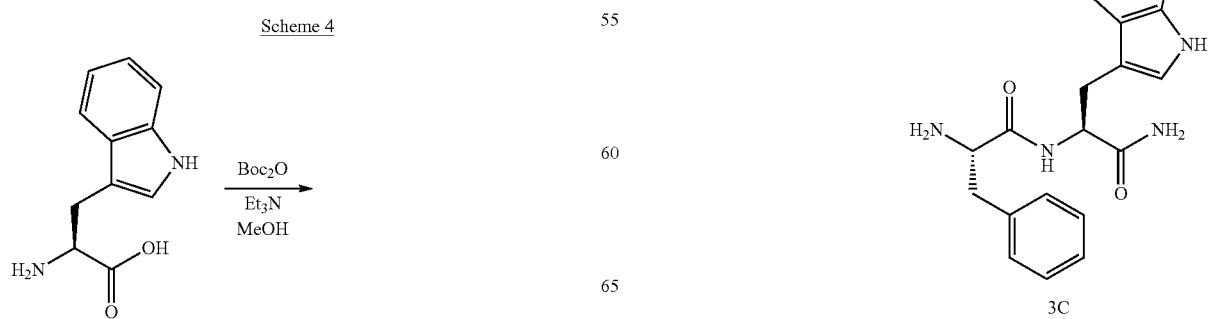

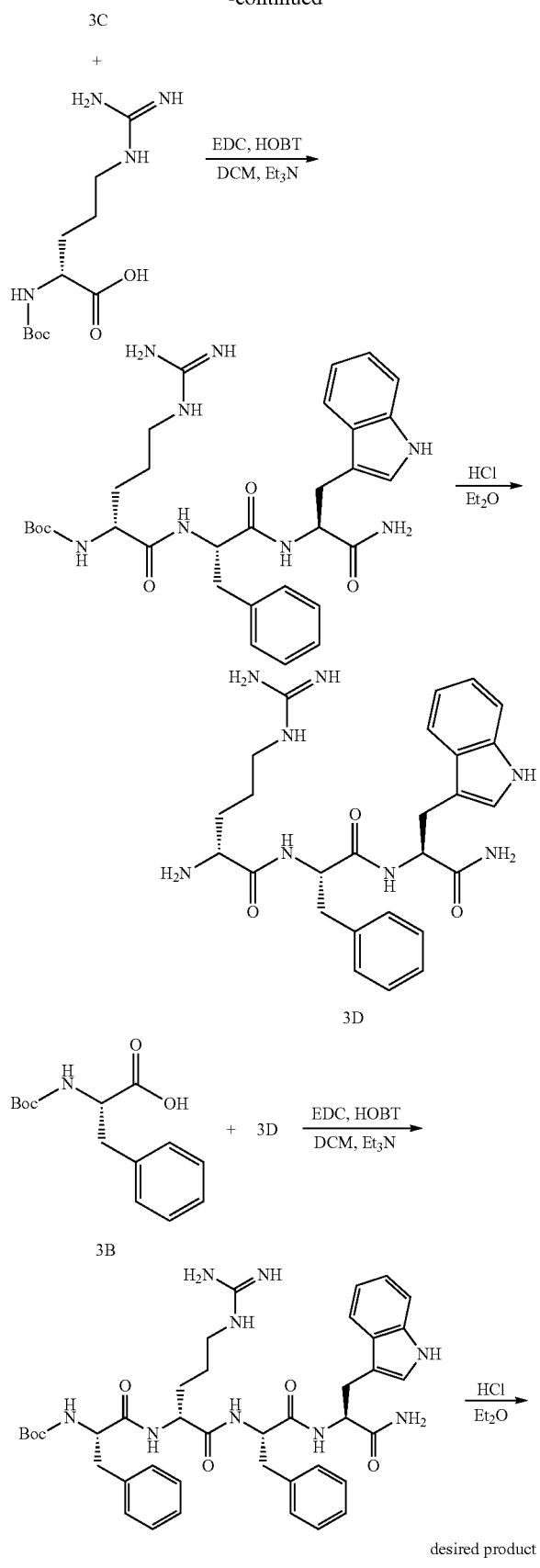

Definitions

The nomenclature used to define the peptide compounds described herein is that typically used in the art wherein the amino group at the N-terminus appears to the left and the carboxyl group at the C-terminus appears to the right.

As used herein, the term "amino acid" includes both a naturally occurring amino acid and a non-natural amino acid. The term "amino acid," unless otherwise indicated, includes both isolated amino acid molecules (i.e., molecules that include both, an amino-attached hydrogen and a carbonyl carbon-attached hydroxyl) and residues of amino acids (i.e., molecules in which either one or both an amino-attached hydrogen or a carbonyl carbon-attached hydroxyl are removed). The amino group can be alpha-amino group, beta-amino group, etc. For example, the term "amino acid alanine" can refer either to an isolated alanine H-Ala-OH or to any one of the alanine residues H-Ala-, -Ala-OH, or -Ala-. Unless otherwise indicated, all amino acids found in the compounds described herein can be either in D or L configuration. An amino acid that is in D configuration may be written such that "D" precedes the amino acid abbreviation. For example, "D-Arg" represents arginine in the D configuration. The term "amino acid" includes salts thereof, including pharmaceutically acceptable salts. Any amino acid can be protected or unprotected. Protecting groups can be attached to an amino group (for example alpha-amino group), the backbone carboxyl group, or any functionality of the side chain. As an example, phenylalanine protected by a benzyloxycarbonyl group (Z) on the alpha-amino group would be represented as Z-Phe-OH.

Many of the amino acids utilized herein are commercially available, or are otherwise known in the art.

With the exception of the N-terminal amino acid, all abbreviations of amino acids (for example, Phe) in this disclosure stand for the structure of NH—C(R)(R')—CO—, wherein R and R' each is, independently, hydrogen or the side chain of an amino acid (e.g., R=benzyl and R'=H for Phe). Accordingly, phenylalanine is H-Phe-OH. The designation "OH" for these amino acids, or for peptides (e.g., Lys-Val-Leu-OH) indicates that the C-terminus is the free acid. The designation "NH$_2$" in, for example, Phe-D-Arg-Phe-Lys-NH$_2$ indicates that the C-terminus of the protected peptide fragment is amidated. Further, certain R and R', separately, or in combination as a ring structure, can include functional groups that require protection during the liquid phase synthesis.

Where the amino acid has isomeric forms, it is the L form of the amino acid that is represented unless otherwise explicitly indicated as D form, for example, D-Arg. Notably, many amino acid residues are commercially available in both D- and L-form. For example, D-Arg is a commercially available D-amino acid.

A capital letter "D" used in conjunction with an abbreviation for an amino acid residue refers to the D-form of the amino acid residue.

As used herein, the term "peptide" refers to two or more amino acids covalently linked by at least one amide bond (i.e., a bond between an amino group of one amino acid and a carboxyl group of another amino acid selected from the amino acids of the peptide fragment). The term "peptide" includes salts thereof, including pharmaceutically acceptable salts.

The articles "a" and "an" are used herein to refer to one or to more than one (i.e., to at least one) of the grammatical object of the article. By way of example, "an element" means one element or more than one element.

The term "alkyl" as used herein is a term of art and refers to saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight-chain or branched-chain alkyl has about 30 or fewer carbon atoms in its backbone (e.g., $C_1$-$C_{30}$ for straight chain, $C_3$-$C_{30}$ for branched chain), and alternatively, about 20 or fewer, 10 or fewer (i.e., $C_1$-$C_{10}$), or 6 or fewer (i.e., $C_1$-$C_6$). Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

As used herein, "aryl" (sometimes abbreviated as "Ar") refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_6$-$C_{14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). An aryl group may be described as, e.g., a $C_6$-$C_{10}$-membered aryl, wherein the term "membered" refers to the non-hydrogen ring atoms within the moiety. Aryl groups include phenyl, naphthyl, indenyl, and tetrahydronaphthyl. Each instance of an aryl group may be independently optionally substituted, i.e., unsubstituted (an "unsubstituted aryl") or substituted (a "substituted aryl") with one or more substituents; e.g., for instance from 1 to 5 substituents, 1 to 4 substituents, 1 to 3 substituents, 1 to 2 substituents or just 1 substituent. The aromatic ring may be substituted at one or more ring positions with one or more substituents, such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. For example, in certain embodiments, the aryl group can be an unsubstituted $C_5$-$C_{12}$ aryl and in certain embodiments, the aryl group can be a substituted $C_5$-$C_{10}$ aryl.

As used herein, the term "heteroaryl" refers to a radical of an aromatic heterocycle that comprises 1, 2, 3 or 4 heteroatoms selected, independently of the others, from nitrogen, sulfur and oxygen. As used herein, the term "heteroaryl" refers to a group that may be substituted or unsubstituted. A heteroaryl may be fused to one or two rings, such as a cycloalkyl, an aryl, or a second heteroaryl ring. The point of attachment of a heteroaryl to a molecule may be on the heteroaryl, cycloalkyl, heterocycloalkyl or aryl ring, and the heteroaryl group may be attached through carbon or a heteroatom. Examples of heteroaryl groups include imidazolyl, furyl, pyrrolyl, thienyl, thiazolyl, isoxazolyl, isothiazolyl, thiadiazolyl, oxadiazolyl, pyridinyl, pyrimidyl, pyrazinyl, pyridazinyl, quinolyl, isoquinolyl, indazolyl, benzoxazolyl, benzisooxazolyl, benzofuryl, benzothiazolyl, indolizinyl, imidazopyridinyl, pyrazolyl, triazolyl, oxazolyl, tetrazolyl, benzimidazolyl, benzoisothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidyl, pyrazolo[3,4]pyrimidyl or benzo(b)thienyl, each of which can be optionally substituted. The aromatic heterocycle may be substituted at one or more ring positions with one or more substituents, such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like.

The term "heterocyclyl" as used herein refers to a radical of a non-aromatic ring system, including, but not limited to, monocyclic, bicyclic, and tricyclic rings, which can be completely saturated or which can contain one or more units of unsaturation—for the avoidance of doubt, the degree of unsaturation does not result in an aromatic ring system—and having 3 to 12 atoms including at least one heteroatom, such as nitrogen, oxygen, or sulfur. For purposes of exemplification, which should not be construed as limiting the scope of this term, the following are examples of heterocyclyl rings: aziridinyl, azirinyl, oxiranyl, thiiranyl, thiirenyl, dioxiranyl, diazirinyl, azetyl, oxetanyl, oxetyl, thietanyl, thietyl, diazetidinyl, dioxetanyl, dioxetenyl, dithietanyl, dithietyl, furyl, dioxalanyl, pyrrolyl, oxazolyl, thiazolyl, imidazolyl, oxadiazolyl, thiadiazolyl, triazolyl, triazinyl, isothiazolyl, isoxazolyl, thiophenyl, pyrazolyl, tetrazolyl, pyridyl, pyridazinyl, pyrimidinyl, pyrazinyl, triazinyl, tetrazinyl, quinolinyl, isoquinolinyl, quinoxalinyl, quinazolinyl, pyridopyrazinyl, benzoxazolyl, benzothiophenyl, benzimidazolyl, benzothiazolyl, benzoxadiazolyl, benzthiadiazolyl, indolyl, benztriazolyl, naphthyridinyl, azepines, azetidinyl, morpholinyl, oxopiperidinyl, oxopyrrolidinyl, piperazinyl, piperidinyl, pyrrolidinyl, quinicludinyl, thiomorpholinyl, tetrahydropyranyl, and tetrahydrofuranyl. More generally, the term "heterocyclic ring" or "heterocycle" refers to a ring of atoms of at least two different elements, one of which is carbon. Additional reference is made to: Oxford Dictionary of Biochemistry and Molecular Biology, Oxford University Press, Oxford, 1997 as evidence that the term "heterocyclic ring" is a term well-established in field of organic chemistry.

As used herein, the term "arylalkyl" or "aralkyl" refers to a radical of an aryl or heteroaryl group ("heteroaralkyl") that is attached to a ($C_1$-$C_2$)alkyl group via an alkylene linker. As used herein, the term "arylalkyl" refers to a group that may be substituted or unsubstituted. The term "arylalkyl" is also intended to refer to those compounds wherein one or more methylene groups in the alkyl chain of the arylalkyl group can be replaced by a heteroatom such as O, N, P, Si, and S, and wherein the nitrogen, phosphorus and sulfur atoms may optionally be oxidized and the nitrogen heteroatom may optionally be quaternized with appended alkyl and/or aryl groups. Arylalkyl groups include for example, benzyl.

As used herein, "cycloalkyl" refers to a radical of a non-aromatic cyclic hydrocarbon group having from 3 to 12 ring carbon atoms ("$C_3$-$C_{12}$ cycloalkyl"). In some embodiments, a cycloalkyl group has 3 to 10 ring carbon atoms ("$C_3$-$C_{10}$ cycloalkyl"). In some embodiments, a cycloalkyl group has 3 to 8 ring carbon atoms ("$C_3$-$C_6$ cycloalkyl"). In some embodiments, a cycloalkyl group has 3 to 6 ring carbon atoms ("$C_3$-$C_6$ cycloalkyl"). In some embodiments, a cycloalkyl group has 5 to 7 ring carbon atoms ("$C_5$-$C_7$ cycloalkyl"). A cycloalkyl group maybe described as, e.g., a $C_4$-$C_7$-membered cycloalkyl, wherein the term "membered" refers to the non-hydrogen ring atoms within the moiety. Exemplary $C_3$-$C_6$ cycloalkyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_3$-$C_7$ cycloalkyl groups include, without limitation, the aforementioned $C_3$-$C_5$ cycloalkyl groups as well as cycloheptyl ($C_6$), cycloheptenyl ($C_7$), cycloheptadienyl ($C_7$), and cycloheptatrienyl ($C_7$), bicyclo[2.1.1]hexanyl ($C_6$), bicyclo[3.1.1]heptanyl ($C_7$), and the like. Exemplary $C_3$-$C_{10}$ cycloalkyl groups include, without limitation, the aforementioned $C_3$-$C_7$ cycloalkyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the cycloalkyl group is either monocyclic ("monocyclic cycloalkyl") or contain a fused, bridged or spiro ring system such as a bicyclic system ("biscyclic cycloalkyl") and can be saturated or can be partially unsaturated. Non-limiting examples of biscyclic cycloalkyl groups include 1-ethylbicyclo[1.1.1]pentane, 1-ethylbicyclo[2.2.2]octane and (3r,5r,7r)-1-ethyladamantane. "Cycloalkyl" also includes ring systems wherein the cycloalkyl ring, as defined above, is fused with one or more aryl groups wherein the point of attachment is on the cycloalkyl ring, and in such instances, the number of carbons continue to designate the number of carbons in the cycloalkyl ring system. Each instance of a cycloalkyl group may be independently optionally substituted, i.e., unsubstituted (an "unsubstituted cycloalkyl") or substituted (a "substituted cycloalkyl") with one or more substituents.

The invention also provides salts of the compounds of the invention.

The term "pharmaceutically acceptable salt" as used herein includes salts derived from inorganic or organic acids including, for example, hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2-sulfonic, and other acids. Pharmaceutically acceptable salt forms can include forms wherein the ratio of molecules comprising the salt is not 1:1. For example, the salt may comprise more than one inorganic or organic acid molecule per molecule of base, such as two hydrochloric acid molecules per molecule of compound. As another example, the salt may comprise less than one inorganic or organic acid molecule per molecule of base, such as two molecules of compound per molecule of tartaric acid.

The terms "carrier" and "pharmaceutically acceptable carrier" as used herein refer to a diluent, adjuvant, excipient, or vehicle with which a compound is administered or formulated for administration. Non-limiting examples of such pharmaceutically acceptable carriers include liquids, such as water, saline, and oils; and solids, such as gum acacia, gelatin, starch paste, talc, keratin, colloidal silica, urea, and the like. In addition, auxiliary, stabilizing, thickening, lubricating, flavoring, and coloring agents may be used. Other examples of suitable pharmaceutical carriers are described in Remington's PharmaceuticalSciences by E. W. Martin, herein incorporated by reference in its entirety.

As used herein, "inhibit" or "inhibiting" means reduce by an objectively measureable amount or degree compared to control. In one embodiment, inhibit or inhibiting means reduce by at least a statistically significant amount compared to control. In one embodiment, inhibit or inhibiting means reduce by at least 5 percent compared to control. In various individual embodiments, inhibit or inhibiting means reduce by at least 10, 15, 20, 25, 30, 33, 40, 50, 60, 67, 70, 75, 80, 90, 95, or 99 percent compared to control.

As used herein, the terms "treating" and "treat" refer to performing an intervention that results in (a) preventing a condition or disease from occurring in a subject that may be at risk of developing or predisposed to having the condition or disease but has not yet been diagnosed as having it; (b) inhibiting a condition or disease, e.g., slowing or arresting its development or progression; or (c) relieving or ameliorating a condition or disease, e.g., causing regression of the condition or disease. In one embodiment the terms "treating" and "treat" refer to performing an intervention that results in (a) inhibiting a condition or disease, e.g., slowing or arresting its development; or (b) relieving or ameliorating a condition or disease, e.g., causing regression of the condition or disease.

As used herein, a "subject" refers to a living animal. In various embodiments a subject is a mammal. In various embodiments a subject is a non-human mammal, including, without limitation, a mouse, rat, hamster, guinea pig, rabbit, sheep, goat, cat, dog, pig, horse, cow, or non-human primate. In certain embodiments, the subject is a human.

As used herein, "administering" has its usual meaning and encompasses administering by any suitable route of administration, including, without limitation, intravenous, intramuscular, intraperitoneal, subcutaneous, direct injection, mucosal, inhalation, oral, and topical.

As used herein, the phrase "effective amount" refers to any amount that is sufficient to achieve a desired biological effect. A "therapeutically effective amount" is an amount that is sufficient to achieve a desired therapeutic effect, e.g., to treat ischemia-reperfusion injury.

Compounds of the invention and the salts thereof can be combined with other therapeutic agents. The compounds of the invention and other therapeutic agent may be administered simultaneously or sequentially. When the other therapeutic agents are administered simultaneously, they can be administered in the same or separate formulations, but they are administered substantially at the same time. The other therapeutic agents are administered sequentially with one another and with compounds of the invention, when the administration of the other therapeutic agents and the compound of the invention is temporally separated. The separation in time between the administration of these compounds may be a matter of minutes or it may be longer.

Pharmaceutical Compositions, Routes of Administration, and Dosing

In certain embodiments, the invention is directed to a pharmaceutical composition, comprising a compound of the invention and a pharmaceutically acceptable carrier. In certain embodiments, the pharmaceutical composition comprises a plurality of compounds of the invention and a pharmaceutically acceptable carrier.

In certain embodiments, a pharmaceutical composition of the invention further comprises at least one additional pharmaceutically active agent other than a compound of the invention. The at least one additional pharmaceutically active agent can be an agent useful in the treatment of ischemia-reperfusion injury.

Pharmaceutical compositions of the invention can be prepared by combining one or more compounds of the invention with a pharmaceutically acceptable carrier and, optionally, one or more additional pharmaceutically active agents.

As stated above, an "effective amount" refers to any amount that is sufficient to achieve a desired biological effect. Combined with the teachings provided herein, by choosing among the various active compounds and weighing factors such as potency, relative bioavailability, patient body weight, severity of adverse side-effects and mode of administration, an effective prophylactic or therapeutic treatment regimen can be planned which does not cause substantial unwanted toxicity and yet is effective to treat the particular subject. The effective amount for any particular application can vary depending on such factors as the disease or condition being treated, the particular compound of the invention being administered, the size of the subject, or the severity of the disease or condition. One of ordinary skill in the art can empirically determine the effective amount of a particular compound of the invention and/or other therapeutic agent without necessitating undue experimentation. A maximum dose may be used, that is, the highest safe dose according to some medical judgment. Multiple doses per day may be contemplated to achieve appropriate systemic levels of compounds. Appropriate systemic levels can be determined by, for example, measurement of the patient's peak or sustained plasma level of the drug. "Dose" and "dosage" are used interchangeably herein.

In certain embodiments, intravenous administration of a compound may typically be from 0.1 mg/kg/day to 20 mg/kg/day. In one embodiment, intravenous administration of a compound may typically be from 0.1 mg/kg/day to 2 mg/kg/day. In one embodiment, intravenous administration of a compound may typically be from 0.5 mg/kg/day to 5 mg/kg/day. In one embodiment, intravenous administration of a compound may typically be from 1 mg/kg/day to 20 mg/kg/day. In one embodiment, intravenous administration of a compound may typically be from 1 mg/kg/day to 10 mg/kg/day.

Generally, daily oral doses of a compound will be, for human subjects, from about 0.01 milligrams/kg per day to 1000 milligrams/kg per day. It is expected that oral doses in the range of 0.5 to 50 milligrams/kg, in one or more administrations per day, will yield therapeutic results. Dosage may be adjusted appropriately to achieve desired drug levels, local or systemic, depending upon the mode of administration. For example, it is expected that intravenous administration would be from one order to several orders of magnitude lower dose per day. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of the compound.

For any compound described herein the therapeutically effective amount can be initially determined from animal models. A therapeutically effective dose can also be determined from human data for compounds which have been tested in humans and for compounds which are known to exhibit similar pharmacological activities, such as other related active agents. Higher doses may be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

The formulations of the invention can be administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the compound can be administered to a subject by any mode that delivers the compound to the desired surface. Administering a pharmaceutical composition may be accomplished by any means known to the skilled artisan. Routes of administration include but are not limited to intravenous, intramuscular, intraperitoneal, intravesical (urinary bladder), oral, subcutaneous, direct injection (for example, into a tumor or abscess), mucosal (e.g., topical to eye), inhalation, and topical.

For intravenous and other parenteral routes of administration, a compound of the invention can be formulated as a lyophilized preparation, as a lyophilized preparation of liposome-intercalated or -encapsulated active compound, as a lipid complex in aqueous suspension, or as a salt complex. Lyophilized formulations are generally reconstituted in suitable aqueous solution, e.g., in sterile water or saline, shortly prior to administration.

For oral administration, the compounds can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, e.g., EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of acid hydrolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, "Soluble Polymer-Enzyme Adducts", In: Enzymes as Drugs, Hocenberg and Roberts, eds., Wiley-Interscience, New York, N.Y., pp. 367-383 (1981); Newmark et al., *J Appl Biochem* 4:185-9 (1982). Other polymers that could be used are poly-1,3-dioxolane and poly-1,3,6-tioxocane. For pharmaceutical usage, as indicated above, polyethylene glycol moieties are suitable.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the compound of the invention (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (e.g., powder); for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the compound of the invention (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, α-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents which can be used and can include benzalkonium chloride and benzethonium chloride. Potential non-ionic detergents that could be included in the formulation as surfactants include lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the compound of the invention or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For topical administration, the compound may be formulated as solutions, gels, ointments, creams, suspensions, etc. as are well-known in the art. Systemic formulations include those designed for administration by injection, e.g., subcutaneous, intravenous, intramuscular, intrathecal or intraperitoneal injection, as well as those designed for transdermal, transmucosal oral or pulmonary administration.

For administration by inhalation, compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

Also contemplated herein is pulmonary delivery of the compounds disclosed herein (or salts thereof). The compound is delivered to the lungs of a mammal while inhaling and traverses across the lung epithelial lining to the blood stream. Other reports of inhaled molecules include Adjei et al., *Pharm Res* 7:565-569 (1990); Adjei et al., *Int J Pharmaceutics* 63:135-144 (1990) (leuprolide acetate); Braquet et al., *J Cardiovasc Pharmacol* 13(suppl. 5):143-146 (1989) (endothelin-1); Hubbard et al., *Annal Int Med* 3:206-212 (1989) (α1-antitrypsin); Smith et al., 1989, *J Clin Invest* 84:1145-1146 (a-1-proteinase); Oswein et al., 1990, "Aerosolization of Proteins", Proceedings of Symposium on Respiratory Drug Delivery II, Keystone, Colorado, March, (recombinant human growth hormone); Debs et al., 1988, *J Immunol* 140:3482-3488 (interferon-gamma and tumor necrosis factor alpha) and Platz et al., U.S. Pat. No. 5,284, 656 (granulocyte colony stimulating factor; incorporated by reference). A method and composition for pulmonary delivery of drugs for systemic effect is described in U.S. Pat. No. 5,451,569 (incorporated by reference), issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, North Carolina; and the Spinhaler powder inhaler, manufactured by Fisons Corp., Bedford, Mass.

All such devices require the use of formulations suitable for the dispensing of the compounds of the invention. Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified compound of the invention may also be prepared in different formulations depending on the type of chemical modification or the type of device employed.

Formulations suitable for use with a nebulizer, either jet or ultrasonic, will typically comprise a compound of the invention (or derivative) dissolved in water at a concentration of about 0.1 to 25 mg of biologically active compound of the invention per mL of solution. The formulation may also include a buffer and a simple sugar (e.g., for inhibitor stabilization and regulation of osmotic pressure). The nebulizer formulation may also contain a surfactant, to reduce or prevent surface induced aggregation of the compound of the invention caused by atomization of the solution in forming the aerosol.

Formulations for use with a metered-dose inhaler device will generally comprise a finely divided powder containing the compound of the invention (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing compound of the invention (or derivative) and may also include a bulking agent, such as lactose, sorbitol, sucrose, or mannitol in amounts which facilitate dispersal of the powder from the device, e.g., 50 to 90% by weight of the formulation. The compound of the invention (or derivative) should advantageously be prepared in particulate form with an average particle size of less than 10 micrometers (µm), most preferably 0.5 to 5 µm, for most effective delivery to the deep lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethylcellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described above, a compound may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer R, *Science* 249:1527-33 (1990).

The compound of the invention and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

Pharmaceutical compositions of the invention contain an effective amount of a compound as described herein and optionally therapeutic agents included in a pharmaceutically acceptable carrier. The term "pharmaceutically acceptable carrier" means one or more compatible solid or liquid filler, diluents or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The therapeutic agent(s), including specifically but not limited to a compound of the invention, may be provided in particles. Particles as used herein means nanoparticles or microparticles (or in some instances larger particles) which can consist in whole or in part of the compound of the invention or the other therapeutic agent(s) as described herein. The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero-order release, first-order release, second-order release, delayed release, sustained release, immediate release, and any combination thereof, etc. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules which contain the compound of the invention in a solution or in a semi-solid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels described in Sawhney H S et al. (1993) *Macromolecules* 26:581-7, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release implant may be particularly suitable for treatment of chronic conditions. "Long-term" release, as used herein, means that the implant is constructed and arranged to deliver therapeutic levels of the active ingredient for at least 7 days, and preferably 30-60 days. Long-term sustained release implants are well-known to those of ordinary skill in the art and include some of the release systems described above.

It will be understood by one of ordinary skill in the relevant arts that other suitable modifications and adaptations to the compositions and methods described herein are readily apparent from the description of the invention contained herein in view of information known to the ordinarily skilled artisan, and may be made without departing from the scope of the invention or any embodiment thereof. Having now described the present invention in detail, the same will be more clearly understood by reference to the following examples, which are included herewith for purposes of illustration only and are not intended to be limiting of the invention.

Methods of Use

The present invention provides peptidic compounds that are useful for treating or preventing ischemia-reperfusion injury or myocardial infarction, or injury associated with myocardial infarction.

Accordingly, in certain embodiments, the invention is directed to a method of treating or preventing ischemia-reperfusion injury, comprising administering to a subject in need thereof a therapeutically effective amount of a compound of formula (I), described herein, or a pharmaceutically acceptable salt thereof. In certain such embodiments, the ischemia-reperfusion injury is cardiac ischemia-reperfusion injury. In some embodiments, the compound is administered orally, topically, systemically, intravenously, subcutaneously, intraperitoneally, or intramuscularly.

In other embodiments, the present invention provides a method for treating or preventing a myocardial infarction, comprising administering to a subject in need thereof a therapeutically effective amount of compound of formula (I), or a pharmaceutically acceptable salt thereof. Such methods may prevent injury to the heart upon reperfusion by preventing the initiation or progression of the infarction. In some embodiments, the compound is administered orally, topically, systemically, intravenously, subcutaneously, intraperitoneally, or intramuscularly Ischemia is reduction or decrease in blood supply to a tissue or an organ and has many different causes. Ischemia may be local, e.g., caused by thrombus or embolus, or more global, e.g., due to low perfusion pressure. An ischemic event can lead to hypoxia (reduced oxygen) and/or anoxia (absence of oxygen).

Ischemia in a tissue or organ of a mammal is a multifaceted pathological condition that is caused by oxygen deprivation (hypoxia) and/or glucose (e.g., substrate) deprivation. Oxygen and/or glucose deprivation in cells of a tissue or organ leads to a reduction or total loss of energy generating capacity and consequent loss of function of active ion transport across the cell membranes. Oxygen and/or glucose deprivation also leads to pathological changes in other cell membranes, including permeability transition in the mitochondrial membranes. In addition other molecules, such as apoptotic proteins normally compartmentalized within the mitochondria, may leak out into the cytoplasm and cause apoptotic cell death. Profound ischemia can lead to necrotic cell death.

Ischemia or hypoxia in a particular tissue or organ may be caused by a loss or severe reduction in blood supply to the tissue or organ. The loss or severe reduction in blood supply may, for example, be due to thromboembolic stroke, coronary atherosclerosis, or peripheral vascular disease. The tissue affected by ischemia or hypoxia is typically muscle, such as cardiac, skeletal, or smooth muscle.

The organ affected by ischemia or hypoxia may be any organ that is subject to ischemia or hypoxia. By way of example, but not by way of limitation, cardiac muscle ischemia or hypoxia is commonly caused by atherosclerotic or thrombotic blockages, which lead to the reduction or loss of oxygen delivery to the cardiac tissues by the cardiac arterial and capillary blood supply. Such cardiac ischemia or hypoxia may cause pain and necrosis of the affected cardiac muscle, and ultimately may lead to cardiac failure.

Reperfusion is the restoration of blood flow to any organ or tissue in which the flow of blood is decreased or blocked. For example, blood flow can be restored to any organ or tissue affected by ischemia. The restoration of blood flow (reperfusion) can occur by any method known to those in the art. For instance, reperfusion of ischemic cardiac tissues may arise from angioplasty, coronary artery bypass graft, or the use of thrombolytic drugs.

Ischemia-reperfusion injury is the cellular or tissue damage caused when blood supply returns to the affected area after a period of ischemia. The lack of oxygen and nutrients during ischemia creates a condition in which the restoration of circulation results damage to the tissues. By way of example, but not by way of limitation, forms of myocardial reperfusion injury including reperfusion-induced arrhythmias, myocardial stunning, microvascular obstruction manifesting in sluggish coronary blood flow, and lethal myocardial reperfusion injury (i.e., reperfusion-induced death of cardiomyocytes that were viable at the end of the index ischemic event). Studies have suggested that lethal myocardial reperfusion injury accounts for about 50% of the final myocardial infarct size.

In certain embodiments, the peptide is administered orally, intravenously, or parenterally.

In certain embodiments, the subject is a human.

A peptidic compound of the invention, or a pharmaceutically acceptable salt thereof, such as acetate, tartrate, or trifluoroacetate salt, may be administered to a subject suspected of, or already suffering from ischemic injury in an amount sufficient to cure, or at least partially arrest, the symptoms of the disease, including its complications and intermediate pathological phenotypes in development of the disease. Subjects suffering from ischemic injury can be identified by any or a combination of diagnostic or prognostic assays known in the art. By way of example, but by way of limitation, in some embodiments, the ischemic injury is related to cardiac ischemia, brain ischemia, renal ischemia, cerebral ischemia, intestinal ischemia, hepatic ischemia, or myocardial infarction.

By way of example, but not by way of limitation, typical symptoms of cardiac ischemia include, but are not limited to, angina (e.g., chest pain and pressure), shortness of breath, palpitations, weakness, dizziness, nausea, sweating, rapid heartbeat, and fatigue.

In some embodiments, treatment of subjects diagnosed with cardiac ischemia with at least one peptide disclosed herein ameliorates or eliminates of one or more of the following symptoms of cardiac ischemia: angina (e.g., chest pain and pressure), shortness of breath, palpitations, weakness, dizziness, nausea, sweating, rapid heartbeat, and fatigue.

By way of example, but not by way of limitation, typical symptoms of renal ischemia include, but are not limited to, uremia (i.e., high blood levels of protein by-products, such as, e.g., urea), acute episodes of dyspnea (labored or difficult breathing) caused by sudden accumulation of fluid in the lungs, hypertension, pain felt near the kidneys, weakness, hypertension, nausea, a history of leg pain, a stride that reflects compromised circulation to the legs, and bruits (sound or murmurs heard with a stethoscope) caused by turbulent blood flow within the arteries may be detected in the neck (e.g., carotid artery bruit), abdomen (which may reflect narrowing of the renal artery), and groin (femoral artery bruit).

In some embodiments, treatment of subjects diagnosed with renal ischemia with at least one peptide disclosed herein ameliorates or eliminates of one or more of the following symptoms of renal ischemia: uremia (i.e., high blood levels of protein by-products, such as, e.g., urea), acute episodes of dyspnea (labored or difficult breathing) caused by sudden accumulation of fluid in the lungs, hypertension, pain felt near the kidneys, weakness, hypertension, nausea, a history of leg pain, a stride that reflects compromised circulation to the legs, and bruits (sound or murmurs heard with a stethoscope) caused by turbulent blood flow within the arteries may be detected in the neck (e.g., carotid artery bruit), abdomen (which may reflect narrowing of the renal artery), and groin (femoral artery bruit).

By way of example, but not by way of limitation, typical symptoms of cerebral (or brain) ischemia include, but are not limited to, blindness in one eye, weakness in one arm or leg, weakness in one entire side of the body, dizziness, vertigo, double vision, weakness on both sides of the body, difficulty speaking, slurred speech, and the loss of coordination.

In some embodiments, treatment of subjects diagnosed with cerebral (or brain) ischemia with at least one peptide disclosed herein ameliorates or eliminates of one or more of the following symptoms of cerebral (or brain) ischemia: blindness in one eye, weakness in one arm or leg, weakness in one entire side of the body, dizziness, vertigo, double vision, weakness on both sides of the body, difficulty speaking, slurred speech, and the loss of coordination.

In another aspect, the present invention relates to methods of treating ischemia reperfusion injury and/or side effects associated with existing therapeutics against ischemia reperfusion injury. In therapeutic applications, a composition or medicament comprising at least one compound of the invention, or a pharmaceutically acceptable salt thereof, such as acetate, tartrate or trifluoroacetate, is administered to a subject suspected of, or already suffering from ischemic reperfusion injury in an amount sufficient to cure, or at least partially arrest, the symptoms of the disease, including its complications and intermediate pathological phenotypes in development of the disease. Subjects suffering from ischemic-reperfusion injury can be identified by any or a combination of diagnostic or prognostic assays known in the art. In some embodiments, the ischemia-reperfusion injury is related to cardiac ischemia, brain ischemia, renal ischemia, cerebral ischemia, intestinal ischemia, and hepatic ischemia. In some embodiments, the peptidic compounds disclosed herein are useful in the treatment of cardiac ischemia-reperfusion injury.

In some embodiments, the peptidic compounds disclosed herein are useful in treating myocardial infarction in a subject to prevent injury to the heart upon reperfusion. In some embodiments, the invention relates to methods of coronary revascularization, comprising administering to a mammalian subject a therapeutically effective amount of a peptidic compound of the invention, or a pharmaceutically acceptable salt thereof, and performing a coronary artery bypass graft (CABG) procedure on the subject.

In some embodiments, treatment of myocardial infarction with the peptidic compounds disclosed herein reduces infarct size, increases LVDP, and increases maximal rates of contraction and relaxation (±dP/dt).

Prophylactic Methods

In some embodiments, the present invention provides methods for preventing or delaying the onset of ischemic injury or symptoms of ischemic injury in a subject at risk of having ischemia injury. In some embodiments, the present technology provides methods for preventing or reducing the symptoms of ischemic injury in a subject at risk of having ischemia injury.

In some embodiments, the present invention provides methods for preventing or delaying the onset of ischemia-reperfusion injury or symptoms of ischemia-reperfusion injury in a subject at risk of having ischemia-reperfusion injury. In some embodiments, the present invention provides methods for preventing or reducing the symptoms of ischemia reperfusion injury in a subject at risk of having ischemia-reperfusion injury.

In some embodiments, the ischemic injury, the ischemia-reperfusion injury, or symptoms of ischemic or ischemia-reperfusion injury is related to cardiac ischemia, brain ischemia, renal ischemia, cerebral ischemia, intestinal ischemia, and hepatic ischemia. In some embodiments, the ischemic injury is myocardial infarction.

In some embodiments, the peptidic compounds disclosed herein are useful in the treatment or prevention of cardiac ischemia-reperfusion injury. In some embodiments, the peptidic compounds disclosed herein are useful in the prevention of cardiac ischemia-reperfusion injury.

Subjects at risk for ischemic injury or ischemia-reperfusion injury can be identified by, e.g., any or a combination of diagnostic or prognostic assays known in the art. In prophylactic applications, a pharmaceutical composition or medicament of a compound of the invention, or a pharmaceutically acceptable salt thereof, such as acetate, tartrate, or trifluoroacetate salt, is administered to a subject susceptible to, or otherwise at risk of for ischemic injury or ischemia reperfusion injury in an amount sufficient to eliminate, reduce the risk, or delay the onset of the disease, including biochemical, histologic and/or behavioral symptoms of the disease, its complications and intermediate pathological phenotypes presenting during development of the disease or reduce the symptoms and/or complications and intermediate pathological phenotypes presenting during development of the disease. Administration of a prophylactic peptide can occur prior to the manifestation of symptoms characteristic of the disease or disorder, such that the disease or disorder is prevented, delayed in its progression, or the severity of the symptoms or side effects of the disease or disorder are reduced.

By way of example, in some embodiments, subjects may be at risk for cardiac ischemia if they have coronary artery disease (atherosclerosis), blood clots, or coronary artery spasm.

By way of example, but not by way of limitation, in some embodiments, subjects may be at risk for renal ischemia if they have kidney injury (e.g., acute kidney injury) and/or injuries or complications from surgeries in which the kidneys are deprived of normal blood flow for extended periods of time (e.g., heart-bypass surgery).

By way of example, but not by way of limitation, in some embodiments, subjects may be at risk for cerebral ischemia if they have sickle cell anemia, compressed blood vessels, ventricular tachycardia, plaque buildup in the arteries, blood clots, extremely low blood pressure as a result of heart attack, had a stroke, or congenital heart defects.

For therapeutic and/or prophylactic applications, a composition comprising at least one peptidic compound described herein, or a pharmaceutically acceptable salt thereof, such as acetate, tartrate, or trifluoroacetate salt, is administered to a subject in need thereof. In some embodiments, the peptide composition is administered one, two, three, four, or five times per day. In some embodiments, the peptide composition is administered more than five times per day. Additionally or alternatively, in some embodiments, the peptide composition is administered every day, every other day, every third day, every fourth day, every fifth day, or every sixth day. In some embodiments, the peptide composition is administered weekly, bi-weekly, tri-weekly, or monthly. In some embodiments, the peptide composition is administered for a period of one, two, three, four, or five weeks. In some embodiments, the peptide is administered for six weeks or more. In some embodiments, the peptide is administered for twelve weeks or more. In some embodiments, the peptide is administered for a period of less than one year. In some embodiments, the peptide is administered for a period of more than one year. In some embodiments, treatment with at least one peptide disclosed herein will prevent or delay the onset of one or more of the following symptoms of cardiac ischemia: angina (e.g., chest pain and pressure), shortness of breath, palpitations, weakness, dizziness, nausea, sweating, rapid heartbeat, and fatigue.

In some embodiments, treatment with at least one peptide disclosed herein will prevent or delay the onset of one or more of the following symptoms of renal ischemia: uremia (i.e., high blood levels of protein by-products, such as, e.g., urea), acute episodes of dyspnea (labored or difficult breathing) caused by sudden accumulation of fluid in the lungs, hypertension, pain felt near the kidneys, weakness, hypertension, nausea, a history of leg pain, a stride that reflects compromised circulation to the legs, and bruits (sound or murmurs heard with a stethoscope) caused by turbulent blood flow within the arteries may be detected in the neck (e.g., carotid artery bruit), abdomen (which may reflect narrowing of the renal artery), and groin (femoral artery bruit).

In some embodiments, treatment with at least one peptide disclosed herein will prevent or delay the onset of one or more of the following symptoms of cerebral (or brain) ischemia: blindness in one eye, weakness in one arm or leg, weakness in one entire side of the body, dizziness, vertigo, double vision, weakness on both sides of the body, difficulty speaking, slurred speech, and the loss of coordination.

Methods of Evaluating Metabolic Stability

In certain embodiments, the following methods can be used to evaluate the metabolic stability of the compounds of the invention.

Certain in vitro liver metabolism studies have been described previously in the following references: Obach, R S, Drug Metab Disp, 1999, 27:1350; Houston, J B et al., Drug Metab Rev, 1997, 29:891; Houston, J B, Biochem Pharmacol, 1994, 47:1469; Iwatsubo, T et al., Pharmacol Ther, 1997, 73:147; and Lave, T, et al., Pharm Res, 1997, 14:152.

Microsomal Assay: Human liver microsomes (20 mg/mL) may be obtained from Xenotech, LLC (Lenexa, Kans.). β-nicotinamide adenine dinucleotide phosphate, reduced form (NADPH), magnesium chloride ($MgCl_2$), and dimethyl sulfoxide (DMSO) may be purchased from Sigma-Aldrich.

Determination of Metabolic Stability: 7.5 mM stock solutions of test compounds are prepared in DMSO. The 7.5 mM stock solutions are diluted to 12.5-50 μM in acetonitrile (ACN). The 20 mg/mL human liver microsomes are diluted to 0.625 mg/mL in 0.1 M potassium phosphate buffer, pH 7.4, containing 3 mM $MgCl_2$. The diluted microsomes are added to wells of a 96-well deep-well polypropylene plate in triplicate. A 10 μL aliquot of the 12.5-50 μM test compound is added to the microsomes and the mixture is pre-warmed for 10 minutes. Reactions are initiated by addition of pre-warmed NADPH solution. The final reaction volume is 0.5 mL and contains 0.5 mg/mL human liver microsomes, 0.25-1.0 μM test compound, and 2 mM NADPH in 0.1 M potassium phosphate buffer, pH 7.4, and 3 mM $MgCl_2$. The reaction mixtures are incubated at 37° C., and 50 μL aliquots are removed at 0, 5, 10, 20, and 30 minutes and added to shallow-well 96-well plates which contain 50 μL of ice-cold ACN with internal standard to stop the reactions. The plates are stored at 4° C. for 20 minutes after which 100 μL of water is added to the wells of the plate before centrifugation to pellet precipitated proteins. Supernatants are transferred to another 96-well plate and analyzed for amounts of parent remaining by LC-MS/MS using an Applied Bio-systems API 4000 mass spectrometer. Testing is done in triplicate.

Data analysis: The in vitro half-lives ($t_{1/2}$s) for test compounds are calculated from the slopes of the linear regression of % parent remaining (ln) vs incubation time relationship: in vitro $t_{1/2}=0.693 k$, where k=−[slope of linear regression of % parent remaining (ln) vs incubation time]

EXAMPLES

General Procedures for Synthesis of Peptides

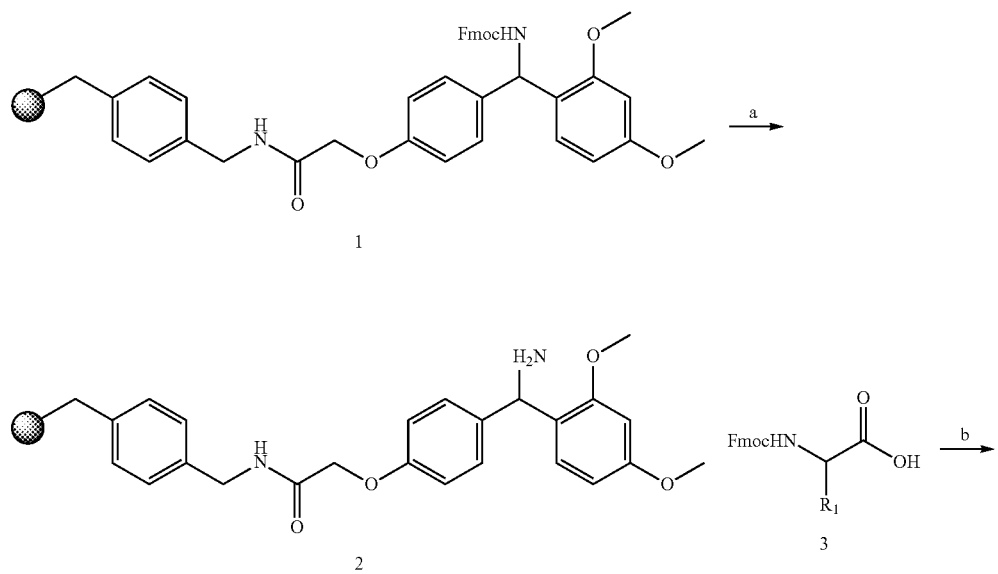

-continued
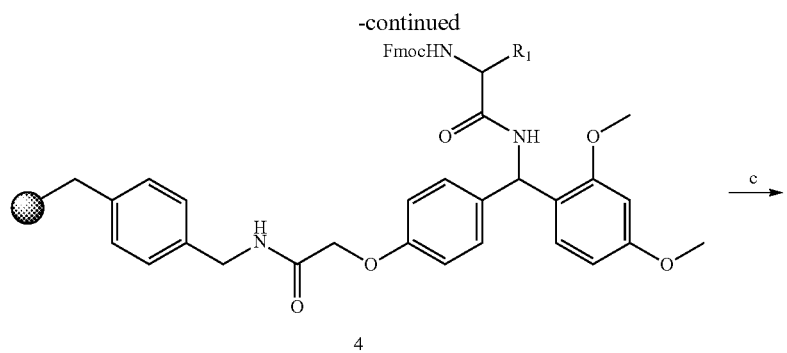
4
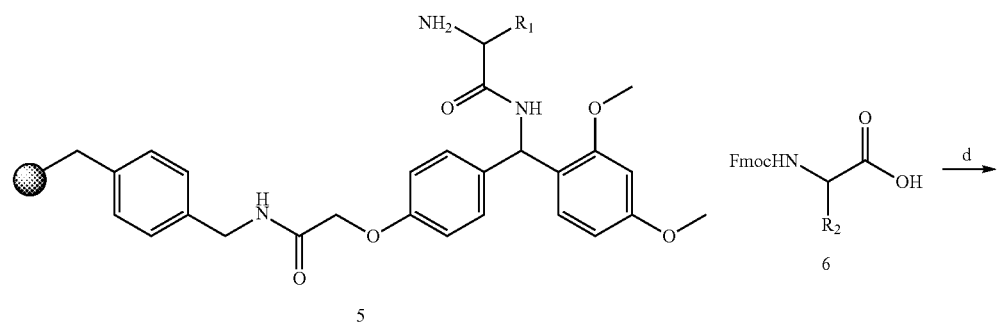
5
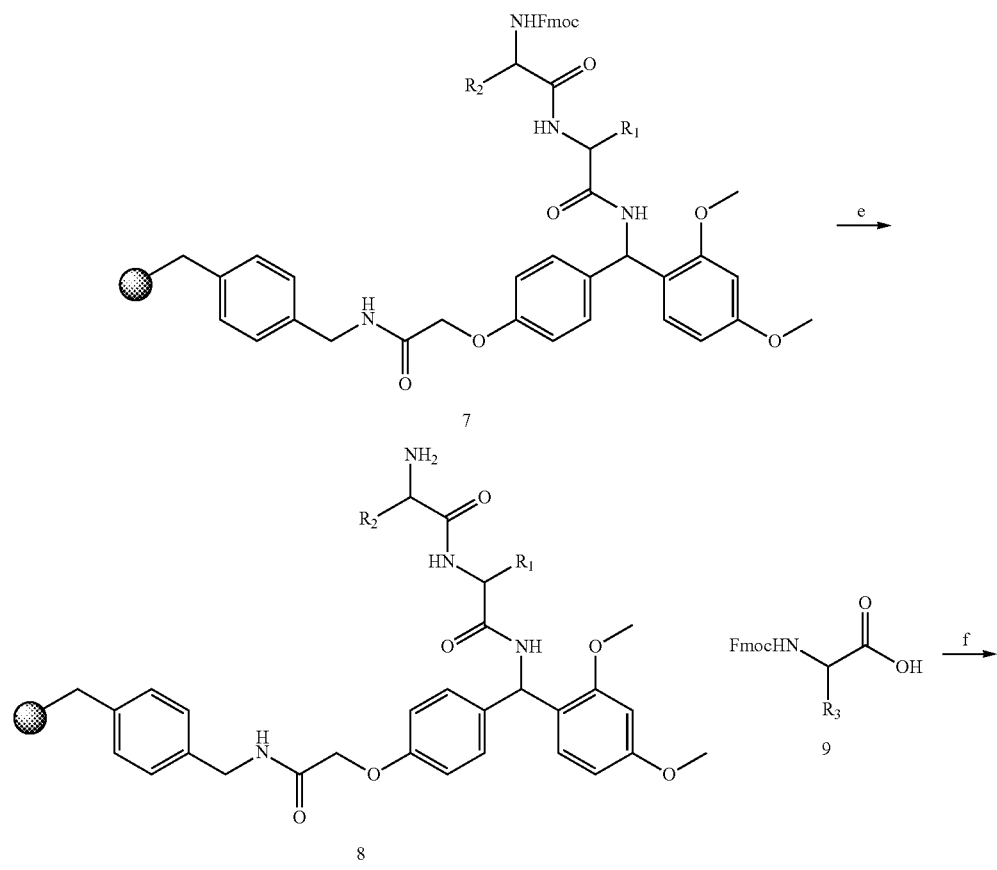
7
8

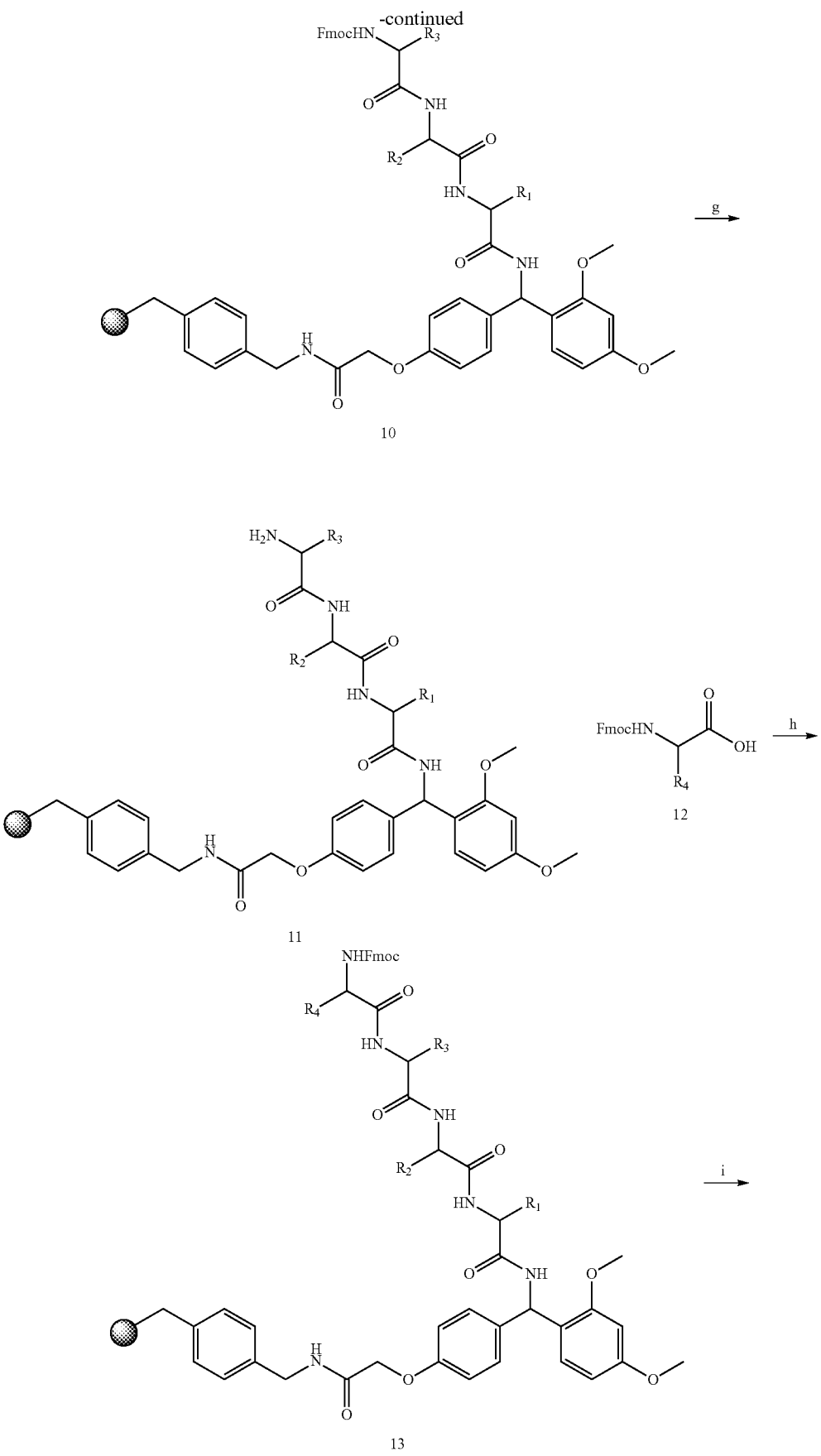

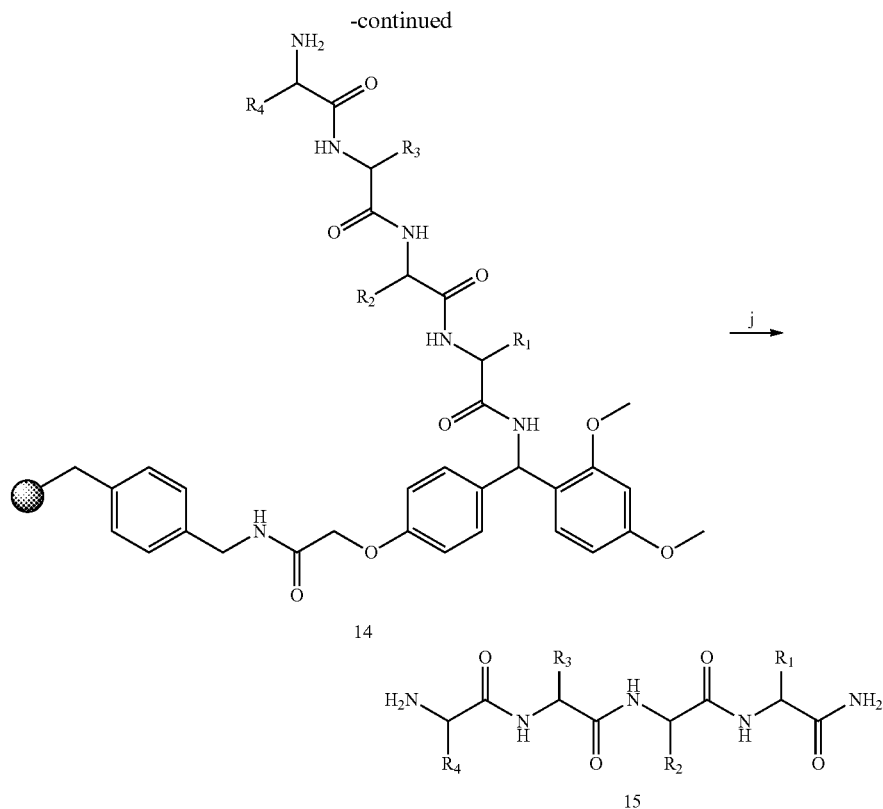

The synthesis of performed by GL Biochem (Shanghai) Ltd.

Step a. Resin Preparation

Weigh 10 g of Rink AM Resin (loading 0.6 mmol/g), dump the resins into a reaction column, and swell it for 30 min with DCM.

Step b. Deprotection

De-protect Fmoc by 20% Piperidine/DMF, mix them for 10 min, then wash it by DMF. Repeat this step.

Step c. Coupling

1) Add 12 mmol Fmoc-Lys(Boc)-OH, 12 mmol HOBT, 12 mmol HBTU and 12 mmol DIEA into the resin for coupling for 40 min at RT.
2) Washing: Wash the resins 1-2 times by DMF after the coupling is completed.

Step b-e (d-h). Increase the Length of the Peptide Chain

By repeating the step 2-4 until all the amino acids are sequentially coupled to the chain.

Step i. Deprotect the Peptide

After the last amino acid has been coupled to the chain, and then wash the resin with MeOH for 3 times. Dry the resin.

Step j. Cleavage

Weight out the dried resin, put them into a tube, add appropriate amount of cleavage solution (e.g. 95% TFA), and incubate it at 40 degree for 3.5 hours. Filter the reaction solution and then precipitate the solution by adding it into Ether.

Centrifuge the solution twice for 2 min (4000/s).

Step k. Drying

Air-dry the peptide sample for a few minutes, and then lyophilize the peptide sample.

Final Product HPLC Purification Procedure

Instrument: HPLC
Wavelength: 220 nm
Flow rate: 30 ml/min
Column: 3 cm DAC ($C_{18}$)
Mobile Phase A: ACN+TFA0.1%, B: Ultrapure water+TFA0.1%

| Gradient: time (min) | A | B |
|---|---|---|
| 0 | 18% | 82% |
| 25 | 28% | 72% |
| 40 | 40% | 60% |

1) Pre-Analysis

Take appropriate amount of sample into a 0.5 ml tube, dissolve it using ultrapure water. Filter the sample using a 0.45 um membrane, then analyze the sample using a fast gradient HPLC(10-100%)

2) Sample Preparation

Add 300 MG sample into a 20 ML beaker, then add 15 ml $H_2O$ and 5 ml ACN. Sonicate the sample until the sample is completely dissolved, then filter the solution using a 0.45 um membrane 3) HPLC Purification Purify the sample using HPLC with the above gradient, collect the fractions at 0-40 min.

Analyze the collected fraction using analytical HPLC to check purity

4) Drying and Lyophilization

Dry the collected fraction using Rotary evaporator then lyophilized it for two days.

5) Storage

Weighted and inspected the dried sample, then store it in a tube. Below 10° C., avoid light.

Example 1: Synthesis of (S)-6-amino-2-((S)-2-((R)-2-((S)-2-amino-3-phenylpropanamido)-5-guanidinopentanamido)-3-cyclohexylpropanamido)hexanamide (Phe-D-Arg-Cha-Lys-NH₂, 15a)

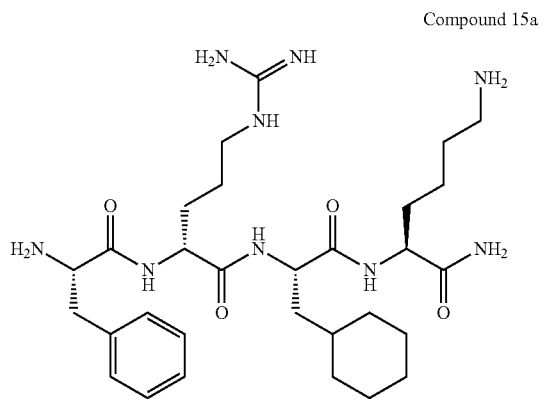 [SMILES: N=C(N)NCCC[C@@H](NC(=O)[C@@H](N)Cc1ccccc1)C(=O)N[C@@H](CC1CCCCC1)C(=O)N[C@@H](CCCCN)C(N)=O]

Compound 15a

Compound 15a was made according to Scheme 1 by using first aminoacid, L-Fmoc-(N6-Boc)-Lys (3a), second aminoacid, L-Fmoc-Cha (6a), third aminoacid, D-Fmoc-Arg (9a), and fourth aminoacid, L-Fmoc-Phe (12a) to give the desired product 15a (HPLC, 98.1%): $^1$H NMR (400 MHz, DMSO-$d_6$), δ=8.66 (m, 1H), 8.40 (m, 1H), 8.26 (m, 3H), 7.94 (m, 1H), 7.86 (m, 4H), 7.40 (m, 1H), 7.34 (m, 5H), 7.08 (m, 1H), 4.38 (m, 2H), 4.14 (m, 2H), 3.02 (m, 4H), 2.75 (m, 2H), 1.00-1.70 (m, 21H), 1.07 (m, 2H). MS (M+1): 602.44.

Example 2: Synthesis of (S)-6-amino-2-((S)-2-((R)-2-((S)-2-amino-3-cyclopentylpropanamido)-5-guanidinopentanamido)-3-cyclopentylpropanamido)hexanamide ((β-Cyclopentyl)-Ala-D-Arg-(β-Cyclopentyl)-Ala-Lys-NH₂, 15b)

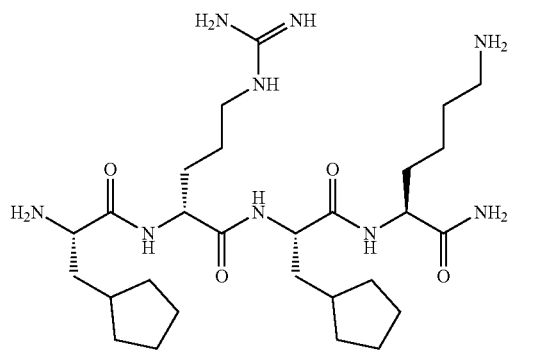

Compound 15b

Compound 15b was made according to Scheme 1 by using first aminoacid, L-Fmoc-(N6-Boc)-Lys (3a), second aminoacid, L-Fmoc-(β-Cyclopentyl)-Ala (6b), third aminoacid, D-Fmoc-Arg (9a), and fourth aminoacid, L-Fmoc-(β-Cyclopentyl)-Ala (6b) to give the desired product 15b (HPLC, 98.1%): $^1$H NMR (400 MHz, DMSO-$d_6$), δ=8.86 (m, 1H), 8.40 (m, 1H), 8.19 (m, 3H), 7.91 (m, 2H), 7.86 (m, 3H), 7.44 (m, 1H), 7.10 (m, 1H), 4.46 (m, 1H), 4.28 (m, 1H), 4.15 (m, 1H), 3.70 (m, 1H), 3.10 (m, 2H), 2.75 (m, 2H), 1.20-1.80 (m, 28H), 1.10 (m, 4H). MS (M+1): 580.45.

Example 3: Synthesis of (S)-6-amino-2-((S)-2-((R)-2-((S)-2-amino-3-cyclopentylpropanamido)-5-guanidinopentanamido)-3-phenylpropanamido)hexanamide ((β-Cyclopentyl)-Ala-D-Arg-Phe-Lys-NH₂, 15c)

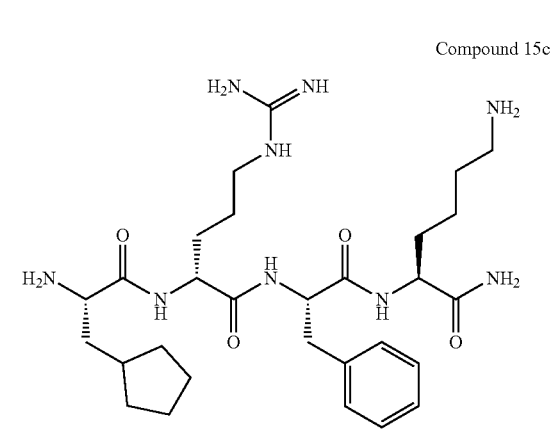 [SMILES: N=C(N)NCCC[C@@H](NC(=O)[C@@H](N)CC1CCCC1)C(=O)N[C@@H](Cc1ccccc1)C(=O)N[C@@H](CCCCN)C(N)=O]

Compound 15c

Compound 15c was made according to Scheme 1 by using first aminoacid, L-Fmoc-(N6-Boc)-Lys (3a), second aminoacid, L-Fmoc-Phe (12a), third aminoacid, D-Fmoc-Arg (9a), and fourth aminoacid, L-Fmoc-(D-Cyclopentyl)-Ala (6b) to give the desired product 15b (HPLC, 99.6%): $^1$H NMR (400 MHz, DMSO-$d_6$), δ=8.74 (m, 1H), 8.48 (m, 1H), 8.16 (m, 4H), 7.86 (m, 3H), 7.72 (m, 1H), 7.43 (m, 1H), 7.29 (m, 5H), 7.24 (m, 1H), 4.60 (m, 1H), 4.38 (m, 1H), 4.20 (m, 1H), 3.80 (m, 1H), 3.10 (m, 1H), 2.90 (m, 2H), 2.75 (m, 3H), 1.70 (m, 6H), 1.50 (m, 7H), 1.30 (m, 4H), 1.10 (m, 4H). MS (M+1): 588.45.

Example 4: Synthesis of (S)-2-((S)-3-([1,1'-biphenyl]-4-yl)-2-((R)-2-((S)-2-amino-3-phenylpropanamido)-5-guanidinopentanamido)propanamido)-6-aminohexanamide (Phe-D-Arg-(4)-Bip-Lys-NH₂, 15d)

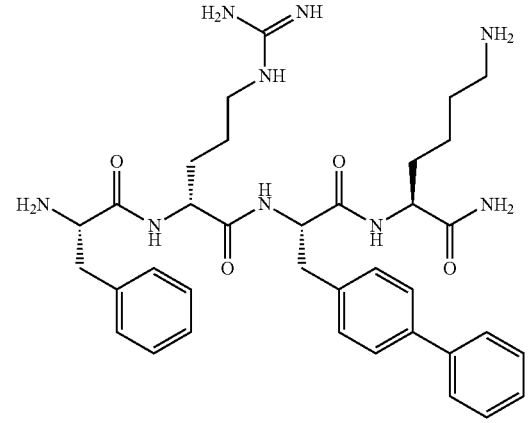

Compound 15d

Compound 15d was made according to Scheme 1 by using first aminoacid, L-Fmoc-(N6-Boc)-Lys (3a), second aminoacid, L-Fmoc-(4)-Bip (6c), third aminoacid, D-Fmoc-Arg (9a), and fourth aminoacid, L-Fmoc-Phe (12a) to give the desired product 15d (HPLC, 99.5%): $^1$H NMR (400 MHz, DMSO-$d_6$), δ=8.65 (m, 1H), 8.45 (m, 1H), 8.20 (m, 4H), 7.80 (m, 3H), 7.60 (m, 5H), 7.45 (m, 4H), 7.30 (m, 5H), 7.15 (m, 1H), 4.60 (m, 1H), 4.32 (m, 1H), 4.15 (m, 2H), 2.60-3.40 (m, 8H), 1.00-1.80 (m, 7H), 0.90 (m, 3H). MS (M+1): 672.42.

Example 5: Synthesis of (S)-6-amino-2-((S)-2-((R)-2-((S)-2-amino-3-phenylpropanamido)-5-guanidinopentanamido)-3-(thiazol-4-yl)propanamido)hexanamide (Phe-D-Arg-(β-thiazol-4-ly)-Ala-Lys-NH$_2$, 15e)

Compound 15e

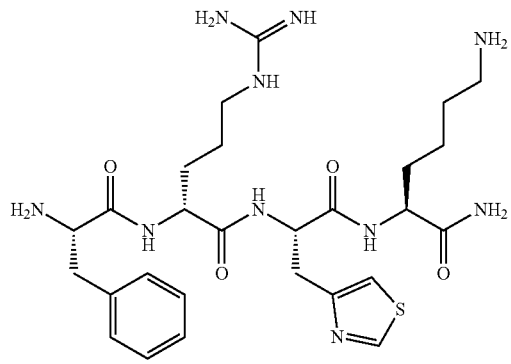

Compound 15e was made according to Scheme 1 by using first aminoacid, L-Fmoc-(N6-Boc)-Lys (3a), second aminoacid, L-Fmoc-(β-thiazol-4-ly)-Ala (6d), third aminoacid, D-Fmoc-Arg (9a), and fourth aminoacid, L-Fmoc-Phe (12a) to give the desired product 15e (HPLC, 99.5%): $^1$H NMR (400 MHz, DMSO-$d_6$), δ=8.99 (s, 1H), 8.63 (m, 1H), 8.43 (m, 1H), 8.20 (m, 3H), 8.10 (m, 1H), 7.78 (m, 3H), 7.60 (m, 1H), 7.50 (s, 1H), 7.30 (m, 6H), 7.10 (m, 1H), 4.70 (m, 1H), 4.32 (m, 1H), 4.12 (m, 2H), 3.22 (m, 1H), 3.00 (m, 5H), 2.75 (m, 2H), 1.70 (m, 1H), 1.50 (m, 3H), 1.20 (m, 4H), 0.90 (m, 2H). MS (M+1): 603.52.

Example 6: Synthesis of (S)-6-amino-2-((S)-2-((R)-2-((S)-2-amino-3-phenylpropanamido)-5-guanidinopentanamido)-3-cyclopentylpropanamido)hexanamide (Phe-D-Arg-Cpa-Lys-NH$_2$, 15f)

Compound 15f

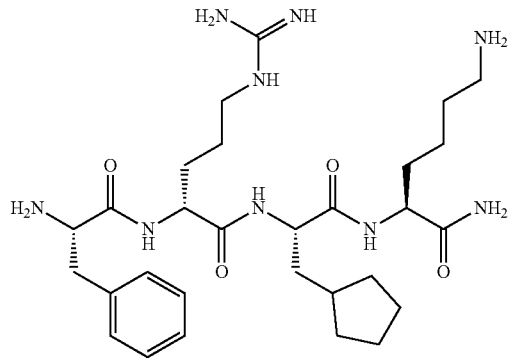

Compound 15f was made according to Scheme 1 by using first aminoacid, L-Fmoc-(N6-Boc)-Lys (3a), second aminoacid, L-Fmoc-(β-Cyclopepnyl)-Ala (6b), third aminoacid, D-Fmoc-Arg (9a), and fourth aminoacid, L-Fmoc-Phe (12a) to give the desired product 15f (HPLC, 99.7%): $^1$H NMR (400 MHz, DMSO-$d_6$+$D_2O$), δ=8.40 (m, 1H), 7.93 (m, 1H), 7.35 (m, 5H), 4.10 (m, 4H), 3.00 (m, 2H), 2.90 (m, 2H), 2.75 (m, 2H), 1.20-1.70 (m, 17H), 1.00 (m, 4H). MS (M+1): 588.56.

Example 7: Synthesis of (S)-6-amino-2-((S)-2-((R)-2-((S)-2-amino-3-phenylpropanamido)-5-guanidinopentanamido)-2-phenylacetamido)hexanamide (Phe-D-Arg-(α-Phenyl)-Gly-Lys-NH$_2$, 15 g)

Compound 15g

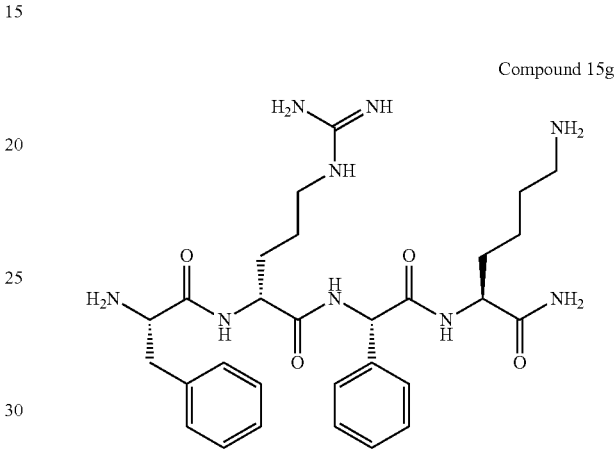

Compound 15g was made according to Scheme 1 by using first aminoacid, L-Fmoc-(N6-Boc)-Lys (3a), second aminoacid, L-Fmoc-(α-phenyl)-Gly (6e), third aminoacid, D-Fmoc-Arg (9a), and fourth aminoacid, L-Fmoc-Phe (12a) to give the desired product 15 g (HPLC, 98.6%): $^1$H NMR (400 MHz, DMSO-$d_6$), δ=8.82 (m, 1H), 8.65 (m, 1H), 8.42 (m, 1H), 8.20 (m, 3H), 7.25 (m, 3H), 7.12 (m, 1H), 7.45 (m, 3H), 7.30 (m, 10H), 5.55 (m, 1H), 4.50 (m, 1H), 4.15 (m, 3H), 3.00 (m, 4H), 2.70 (m, 2H), 1.00-1.70 (m, 10H). MS (M+1): 582.40.

Example 8: Synthesis of (S)-6-amino-2-((S)-2-((R)-2-((S)-2-amino-2-phenylacetamido)-5-guanidinopentanamido)-3-phenylpropanamido)hexanamide ((α-phenyl)-Gly-D-Arg-Phe-Lys-NH$_2$, 15 h)

Compound 15h

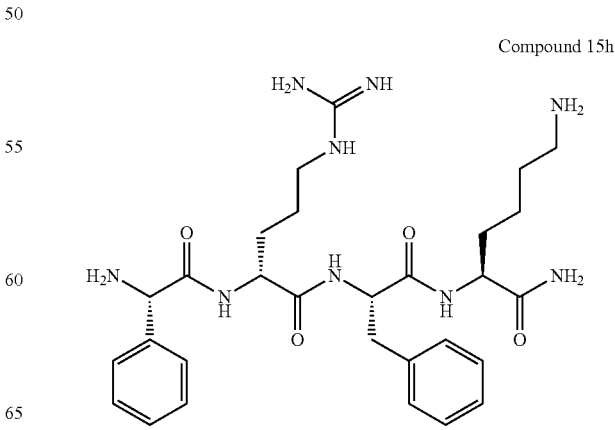

Compound 15h was made according to Scheme 1 by using first aminoacid, L-Fmoc-(N6-Boc)-Lys (3a), second aminoacid, L-Fmoc-Phe (12a), third aminoacid, D-Fmoc-Arg (9a), and fourth aminoacid, L-Fmoc-(α-phenyl)-Gly (6e) to give the desired product 15 h (HPLC, 98.5%): ¹H NMR (400 MHz, DMSO-d₆), δ=8.70 (m, 4H), 8.50 (m, 1H), 8.25 (m, 1H), 7.80 (m, 3H), 7.40 (m, 7H), 7.20 (m, 7H), 5.00 (m, 1H), 4.60 (m, 1H), 4.35 (m, 1H), 4.15 (m, 1H), 3.20 (m, 2H), 2.70 (m, 4H), 1.60 (m, 4H), 1.25 (m, 3H), 1.08 (m, 2H), 0.75 (m, 1H). MS (M+1): 582.45.

Example 9: Synthesis of (S)-6-amino-2-((S)-2-((R)-2-((S)-2-amino-2-phenylacetamido)-5-guanidinopentanamido)-2-phenylacetamido)hexanamide ((α-phenyl)-Gly-D-Arg-(α-phenyl)-Gly-Lys-NH₂, 15i)

Compound 15i

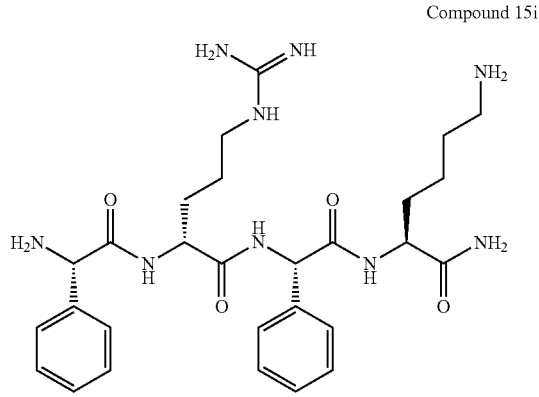 [SMILES: N=C(N)NCCC[C@@H](NC(=O)[C@@H](N)c1ccccc1)C(=O)N[C@H](C(=O)N[C@@H](CCCCN)C(N)=O)c1ccccc1]

Compound 15i was made according to Scheme 1 by using first aminoacid, L-Fmoc-(N6-Boc)-Lys (3a), second aminoacid, L-Fmoc-(α-phenyl)-Gly (6e), third aminoacid, D-Fmoc-Arg (9a), and fourth aminoacid, L-Fmoc-(α-phenyl)-Gly (6e) to give the desired product 15i (HPLC, 98.1%): ¹H NMR (400 MHz, DMSO-d₆), δ=8.85 (m, 2H), 8.22 (m, 3H), 8.45 (m, 1H), 7.85 (m, 3H), 7.65 (m, 1H), 7.55 (m, 3H), 7.45 (m, 5H), 7.30 (m, 5H), 5.58 (m, 1H), 5.06 (m, 1H), 4.58 (m, 1H), 4.18 (m, 1H), 2.90 (m, 2H), 2.75 (m, 2H), 1.60 (m, 5H), 1.30 (m, 5H), 1.10 (m, 2H). MS (M+1): 568.45.

Example 10: Synthesis of (S)-6-amino-2-((S)-2-((R)-2-((S)-2-amino-3-phenylpropanamido)-5-guanidinopentanamido)-3-(o-tolyl)propanamido)hexanamide (Phe-D-Arg-(2-Methyl)-Phe-Lys-NH₂, 15j)

Compound 15j

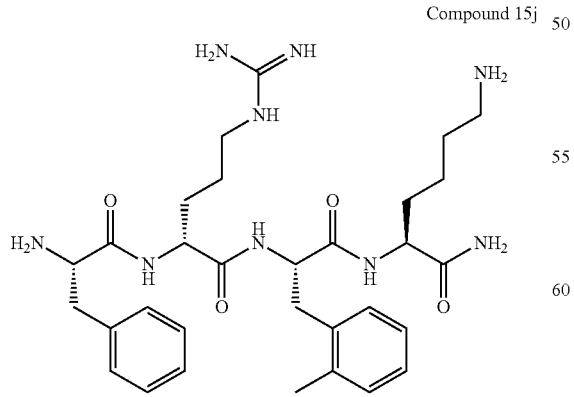

Compound 15j was made according to Scheme 1 by using first aminoacid, L-Fmoc-(N6-Boc)-Lys (3a), second aminoacid, L-Fmoc-(2-methyl)-Phe (6f), third aminoacid, D-Fmoc-Arg (9a), and fourth aminoacid, L-Fmoc-Phe (12a) to give the desired product 15j (HPLC, 99.0%): ¹H NMR (400 MHz, DMSO-d₆), δ=8.59 (m, 1H), 8.52 (m, 1H), 8.22 (m, 2H), 8.03 (m, 1H), 7.84 (m, 3H), 7.60 (m, 1H), 7.38 (m, 3H), 7.25 (m, 3H), 7.20 (m, 2H), 7.08 (m, 5H), 4.62 (m, 1H), 4.32 (m, 1H), 4.15 (m, 2H), 3.10 (m, 1H), 2.98 (m, 2H), 2.80 (m, 5H), 2.32 (s, 3H), 1.68 (m, 1H), 1.55 (m, 3H), 1.38 (m, 3H), 1.10 (m, 1H), 0.88 (m, 2H). MS (M+1): 610.45.

Example 11: Synthesis of (S)-6-amino-2-((S)-2-((R)-2-((S)-2-amino-3-phenylpropanamido)-5-guanidinopentanamido)-3-(p-tolyl)propanamido)hexanamide (Phe-D-Arg-(4-Methyl)-Phe-Lys-NH₂, 15k)

Compound 15k

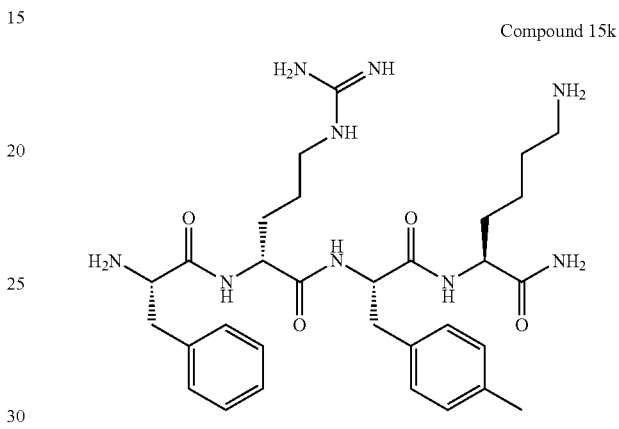

Compound 15k was made according to Scheme 1 by using first aminoacid, L-Fmoc-(N6-Boc)-Lys (3a), second aminoacid, L-Fmoc-(4-methyl)-Phe (6 g), third aminoacid, D-Fmoc-Arg (9a), and fourth aminoacid, L-Fmoc-Phe (12a) to give the desired product 15k (HPLC, 98.7%): ¹H NMR (400 MHz, DMSO-d₆), δ=8.55 (m, 1H), 8.42 (m, 1H), 8.21 (m, 3H), 8.14 (m, 1H), 7.83 (m, 3H), 7.58 (m, 1H), 7.25 (m, 6H), 7.15 (m, 5H), 4.56 (m, 1H), 4.20 (m, 1H), 4.16 (m, 2H), 3.00 (m, 3H), 2.78 (m, 4H), 2.24 (s, 3H), 1.65 (m, 1H), 1.55 (m, 3H), 1.20 (m, 4H), 0.85 (m, 2H). MS (M+1): 610.45.

Example 12: Synthesis of (S)-6-amino-2-((S)-2-((R)-2-((S)-2-amino-3-phenylpropanamido)-5-guanidinopentanamido)-3-(4-(tert-butyl)phenyl)propanamido)hexanamide (Phe-D-Arg-(4-tert-Butyl)-Phe-Lys-NH₂, 15l)

Compound 15l

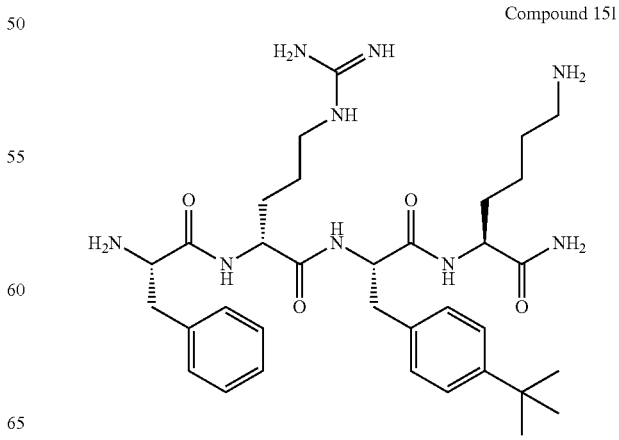

Compound 15l was made according to Scheme 1 by using first aminoacid, L-Fmoc-(N6-Boc)-Lys (3a), second aminoacid, L-Fmoc-(4-tert-Butyl)-Phe (6 h), third aminoacid, D-Fmoc-Arg (9a), and fourth aminoacid, L-Fmoc-Phe (12a) to give the desired product 15l (HPLC, 98.9%): ¹H NMR (400 MHz, DMSO-d₆+D₂O), δ=7.25 (m, 5H), 7.12 (m, 4H), 4.45 (m, 1H), 4.12 (m, 1H), 3.95 (m, 2H), 3.05 (m, 2H), 2.90 (m, 1H), 2.70 (m, 5H), 1.60 (m, 4H), 1.35 (m, 2H), 1.16 (s, 9H), 0.95 (m, 2H), 0.70 (m, 2H). MS (M+1): 652.68.

Example 13: Synthesis of (S)-2-((R)-2-((S)-2-amino-3-phenylpropanamido)-5-guanidinopentanamido)-N—((S)-1,6-diamino-1-oxohexan-2-yl)decanamide (Phe-D-Arg-(β-n-heptyl)-Ala-Lys-NH₂, 15 m)

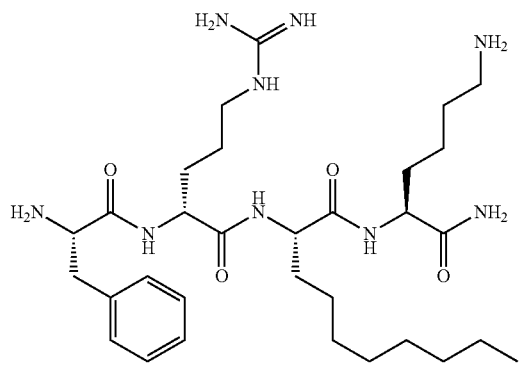

Compound 15m

Compound 15m was made according to Scheme 1 by using first aminoacid, L-Fmoc-(N6-Boc)-Lys (3a), second aminoacid, L-Fmoc-(β-n-Heptyl)-Phe (6i), third aminoacid, D-Fmoc-Arg (9a), and fourth aminoacid, L-Fmoc-Phe (12a) to give the desired product 15 m (HPLC, 99.2%): ¹H NMR (400 MHz, DMSO-d₆), δ=8.66 (m, 1H), 8.37 (m, 4H), 7.95 (m, 1H), 7.85 (m, 3H), 7.28 (m, 1H), 7.30 (m, 6H), 7.05 (m, 1H), 4.38 (m, 1H), 4.25 (m, 1H), 4.15 (m, 2H), 3.00 (m, 4H), 2.75 (m, 2H), 1.65 (m, 2H), 1.50 (m, 4H), 1.25 (m, 18H), 0.85 (m, 3H). MS (M+1): 618.67.

Example 14: Synthesis of (R)—N—((S)-1-(((S)-1-amino-3-(1H-indol-3-yl)-1-oxopropan-2-yl)amino)-1-oxo-3-phenylpropan-2-yl)-2-((S)-2-amino-3-phenylpropanamido)-5-guanidinopentanamide (Phe-D-Arg-Phe-Trp-NH₂, 15n)

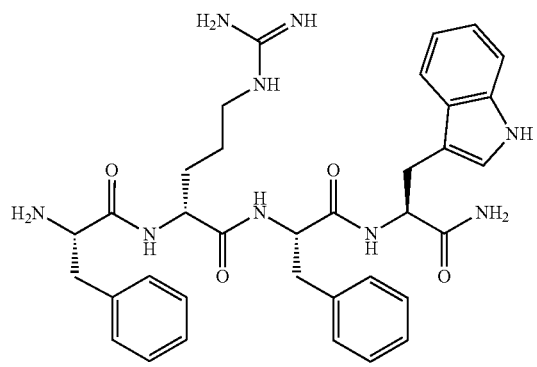

Compound 15n

Compound 15n was made according to Scheme 1 by using first aminoacid, L-Fmoc-Trp (3b), second aminoacid, L-Fmoc-Phe (12a), third aminoacid, D-Fmoc-Arg (9a), and fourth aminoacid, L-Fmoc-Phe (12a) to give the desired product 15n (HPLC, 98.7%): ¹H NMR (400 MHz, CD₃OD), δ=8.66 (m, 1H), 7.70 (m, 1H), 7.22 (m, 14H), 4.78 (m, 1H), 4.56 (m, 1H), 4.15 (m, 1H), 4.08 (m, 1H), 3.73 (m, 1H), 3.20 (m, 5H), 2.92 (m, 2H), 2.60 (m, 1H), 1.40 (m, 2H), 1.08 (m, 1H), 0.88 (m, 1H). MS (M+1): 654.61.

Example 15: Synthesis of (R)—N—((S)-1-(((S)-1-amino-3-(1H-imidazol-4-yl)-1-oxopropan-2-yl)amino)-1-oxo-3-phenylpropan-2-yl)-2-((S)-2-amino-3-phenylpropanamido)-5-guanidinopentanamide (Phe-D-Arg-Phe-His-NH₂, 15o)

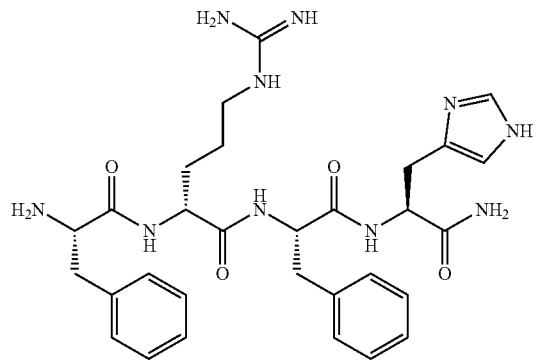

Compound 15o

Compound 15o was made according to Scheme 1 by using first aminoacid, L-Fmoc-His (3c), second aminoacid, L-Fmoc-Phe (12a), third aminoacid, D-Fmoc-Arg (9a), and fourth aminoacid, L-Fmoc-Phe (12a) to give the desired product 15o (HPLC, 98.6%): ¹H NMR (400 MHz, CD₃OD), δ=8.88 (s, 1H), 7.50 (s, 1H), 7.30 (m, 10H), 4.76 (m, 1H), 4.59 (m, 1H), 4.22 (m, 1H), 4.16 (m, 1H), 3.35 (m, 1H), 3.20 (m, 4H), 3.00 (m, 2H), 2.90 (m, 1H), 1.40 (m, 2H), 1.06 (m, 2H). MS (M+1): 605.47.

Example 16: Synthesis of (S)-6-amino-2-((S)-2-((R)-2-((S)-2-amino-3-phenylpropanamido)-5-guanidinopentanamido)-3-(2,3-dimethylphenyl)propanamido)hexanamide (Phe-D-Arg-(2,3-dimethyl)-Phe-Lys-NH₂, 15p)

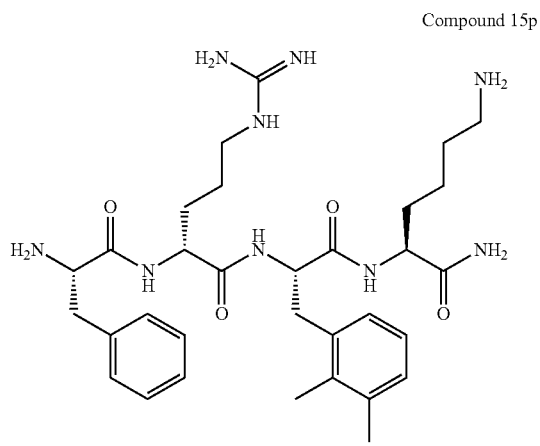 [SMILES: Cc1cccc(C[C@H](NC(=O)[C@@H](CCCNC(=N)N)NC(=O)[C@@H](N)Cc2ccccc2)C(=O)N[C@@H](CCCCN)C(N)=O)c1C]

Compound 15p

Compound 15p was made according to Scheme 1 by using first aminoacid, L-Fmoc-Lys (3a), second aminoacid, L-Fmoc-(2,3-dimethyl)-Phe (6j), third aminoacid, D-Fmoc-Arg (9a), and fourth aminoacid, L-Fmoc-Phe (12a) to give the desired product 1⁵p (HPLC, 99.1%): ¹H NMR (400 MHz, CD₃OD), δ=7.32 (m, 5H), 7.02 (m, 3H), 4.62 (m, 1H), 4.43 (m, 1H), 4.12 (m, 2H), 3.45 (m, 1H), 3.12 (m, 2H), 2.96 (m, 3H), 2.90 (m, 2H), 2.30 (s, 3H), 2.28 (s, 3H), 1.65-1.90 (m, 4H), 1.50 (m, 2H), 1.35 (m, 2H), 1.16 (m, 1H), 0.96 (m, 1H). MS (M+1): 624.31.

Example 17. Synthesis of (S)-6-amino-2-((S)-2-((R)-2-((S)-2-amino-3-phenylpropanamido)-5-guanidinopentanamido)-3-(2,4-dimethylphenyl)propanamido)hexanamide (Phe-D-Arg-(2,4-dimethyl)-Phe-Lys-NH₂, 15q)

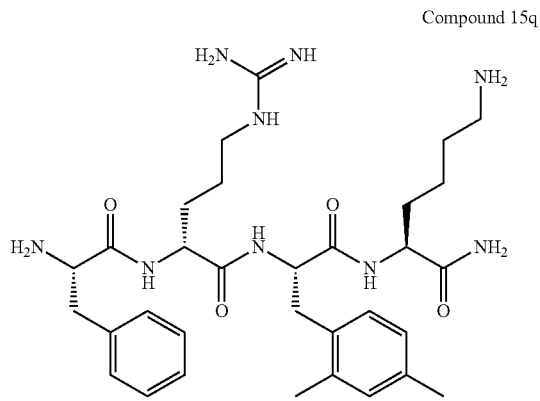 [SMILES: Cc1ccc(C[C@H](NC(=O)[C@@H](CCCNC(=N)N)NC(=O)[C@@H](N)Cc2ccccc2)C(=O)N[C@@H](CCCCN)C(N)=O)c(C)c1]

Compound 15q

Compound 15q was made according to Scheme 1 by using first aminoacid, L-Fmoc-Lys (3a), second aminoacid, L-Fmoc-(2,4-dimethyl)-Phe (6k), third aminoacid, D-Fmoc-Arg (9a), and fourth aminoacid, L-Fmoc-Phe (12a) to give the desired product 15q (HPLC, 99.4%): ¹H NMR (400 MHz, CD₃OD), δ=7.32 (m, 5H), 7.06 (m, 1H), 6.98 (s, 1H), 6.92 (m, 1H), 4.61 (m, 1H), 4.41 (m, 1H), 4.13 (m, 2H), 3.32 (m, 1H), 3.14 (m, 2H), 2.98 (m, 3H), 2.88 (m, 2H), 2.34 (s, 3H), 2.27 (s, 3H), 1.60-1.90 (m, 4H), 1.55 (m, 2H), 1.35 (m, 2H), 1.10 (m, 2H). MS (M+1): 624.45.

Example 18: Synthesis of (S)—N—((S)-1-amino-3-(1H-imidazol-4-yl)-1-oxopropan-2-yl)-2-((R)-2-((S)-2-amino-3-phenylpropanamido)-5-guanidinopentanamido)-5-methylhexanamide (Phe-D-Arg-homoLeu-His-NH₂, 15r)

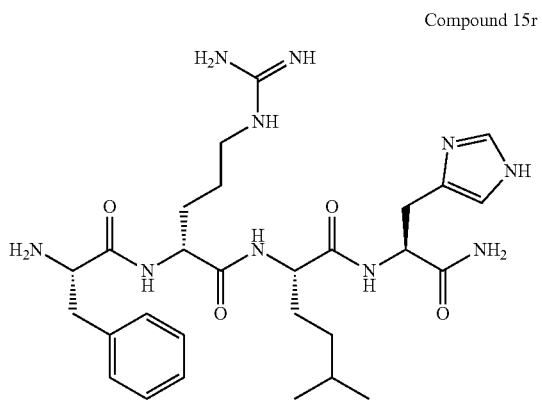 [SMILES: CC(C)CC[C@H](NC(=O)[C@@H](CCCNC(=N)N)NC(=O)[C@@H](N)Cc1ccccc1)C(=O)N[C@@H](Cc1c[nH]cn1)C(N)=O]

Compound 15r

Compound 15r was made according to Scheme 1 by using first aminoacid, L-Fmoc-His (3c), second aminoacid, L-Fmoc-homoLeu (6l), third aminoacid, D-Fmoc-Arg (9a), and fourth aminoacid, L-Fmoc-Phe (12a) to give the desired product 15r (HPLC, 98.6%): ¹H NMR (400 MHz, CD₃OD), δ=8.86 (s, 1H), 7.33 (m, 6H), 4.65 (m, 1H), 4.20 (m, 3H), 3.30 (m, 1H), 3.15 (m, 5H), 1.80 (m, 1H), 1.70 (m, 1H), 1.60 (m, 3H), 1.35 (m, 2H), 1.20 (m, 2H), 0.90 (d, J=6.8 Hz, 6H). MS (M+1): 585.45.

Example 19: Synthesis of (S)-6-amino-2-((S)-2-((R)-2-((S)-2-amino-3-phenylpropanamido)-5-guanidinopentanamido)-3-mesitylpropanamido)hexanamide (Phe-D-Arg-(2,4,6-trimethyl)-Phe-Lys-NH₂, 15s)

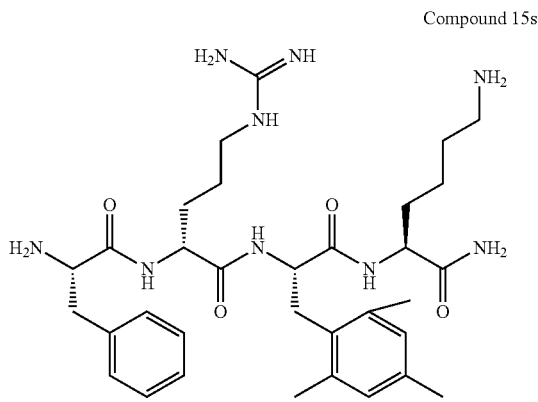 [SMILES: Cc1cc(C)c(C[C@H](NC(=O)[C@@H](CCCNC(=N)N)NC(=O)[C@@H](N)Cc2ccccc2)C(=O)N[C@@H](CCCCN)C(N)=O)c(C)c1]

Compound 15s

Compound 15s was made according to Scheme 1 by using first aminoacid, L-Fmoc-Lys (3a), second aminoacid, L-Fmoc-(2,4,6-trimethyl)-Phe (6 m), third aminoacid, D-Fmoc-Arg (9a), and fourth aminoacid, L-Fmoc-Phe (12a) to give the desired product 15s (HPLC, 98.6%): $^1$H NMR (400 MHz, CD$_3$OD), δ=7.32 (m, 5H), 6.82 (s, 2H), 4.66 (m, 1H), 4.32 (m, 1H), 4.18 (m, 2H), 3.28 (m, 1H), 3.15 (m, 2H), 3.00 (m, 5H), 2.24 (s, 6H), 2.22 (s, 3H), 1.88 (m, 1H), 1.72 (m, 2H), 1.50 (m, 5H), 1.12 (m, 2H). MS (M+1): 638.61.

Example 20: Synthesis of (S)—N—((S)-1-amino-3-(1H-imidazol-4-yl)-1-oxopropan-2-yl)-2-((R)-2-((S)-2-amino-3-phenylpropanamido)-5-guanidinopentanamido)-6-methylheptanamide (Phe-D-Arg-(2,4,6-trimethyl)-Phe-Lys-NH$_2$, 15t)

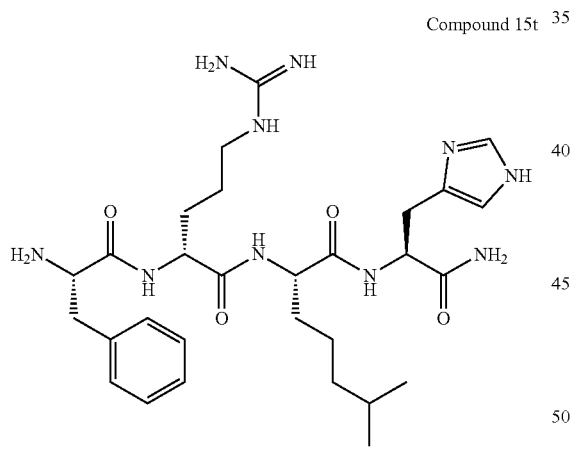

Compound 15t

Compound 15t was made according to Scheme 1 by using first aminoacid, L-Fmoc-His (3c), second aminoacid, L-Fmoc-(D-(3-methylbutan-1-yl))-Ala (6n), third aminoacid, D-Fmoc-Arg (9a), and fourth aminoacid, L-Fmoc-Phe (12a) to give the desired product 15t (HPLC, 99.5%): $^1$H NMR (400 MHz, CD$_3$OD), δ=8.85 (d, J=1.2 Hz, 1H), 7.33 (m, 6H), 4.73 (m, 1H), 4.23 (m, 3H), 3.28 (m, 1H), 3.12 (m, 5H), 1.75 (m, 2H), 1.65 (m, 4H), 1.35 (m, 3H), 1.20 (m, 2H), 0.89 (m, 6H). MS (M+1): 599.90.

Example 21: Synthesis of (S)-6-amino-2-((S)-2-((R)-2-((S)-2-amino-3-cyclohexylpropanamido)-5-guanidinopentanamido)-3-cyclohexylpropanamido)hexanamide (Cha-D-Arg-Cha-Lys-NH$_2$, 15u)

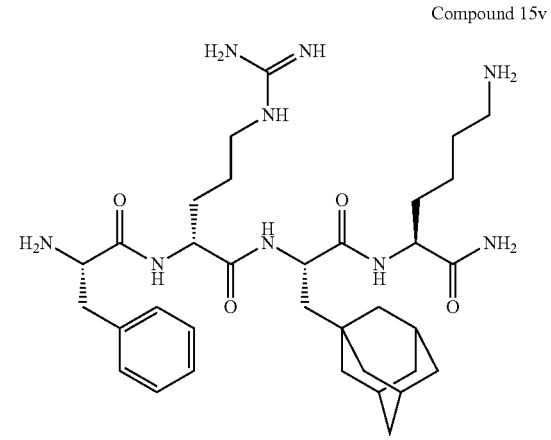 [SMILES: N=C(N)NCCC[C@@H](NC(=O)[C@@H](N)Cc1ccccc1)C(=O)N[C@@H](CC12CC3CC(CC(C3)C1)C2)C(=O)N[C@@H](CCCCN)C(N)=O]

Compound 15u

Compound 15u was made according to Scheme 1 by using first aminoacid, L-Fmoc-Lys (3a), second aminoacid, L-Fmoc-Cha (6a), third aminoacid, D-Fmoc-Arg (9a), and fourth aminoacid, L-Fmoc-Cha (6a) to give the desired product 15u (HPLC, 98.1%): $^1$H NMR (400 MHz, CD$_3$OD), δ=4.38 (m, 3H), 4.04 (m, 1H), 3.27 (m, 2H), 2.96 (m, 2H), 1.10-1.90 (m, 32H), 1.00 (m, 4H). MS (M+1): 608.60.

Example 22: Synthesis of (2S)-2-((2S)-3-(adamantan-1-yl)-2-((R)-2-((S)-2-amino-3-phenylpropanamido)-5-guanidinopentanamido)propanamido)-6-aminohexanamide (Phe-D-Arg-(β-admant-1-yl)-Ala-Lys-NH$_2$, 15v)

Compound 15v

Scheme 2
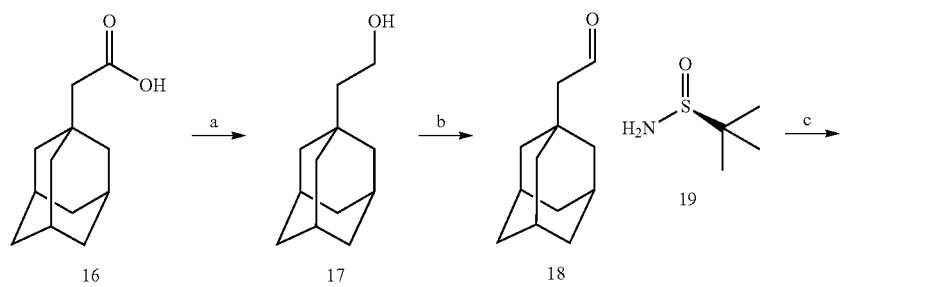
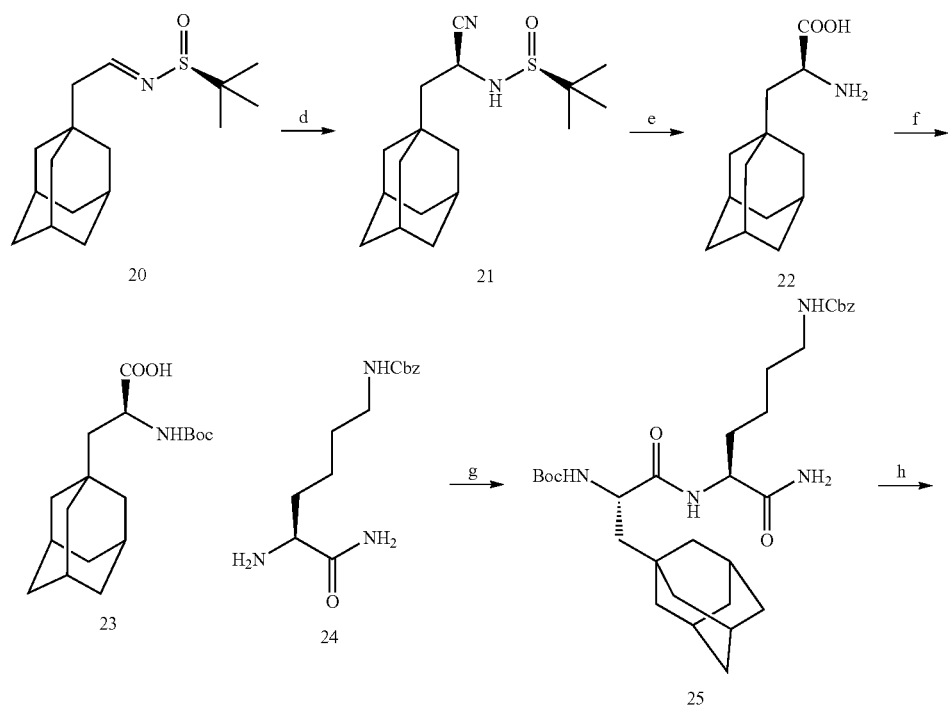
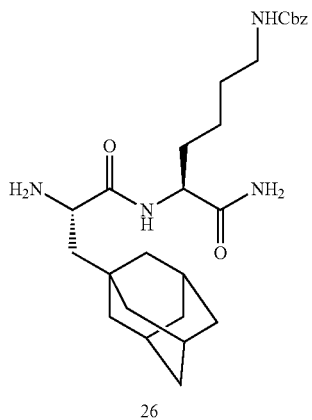

-continued
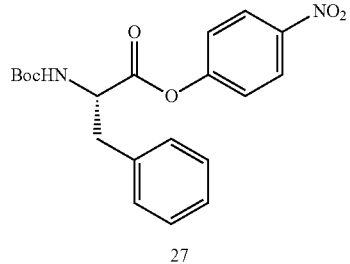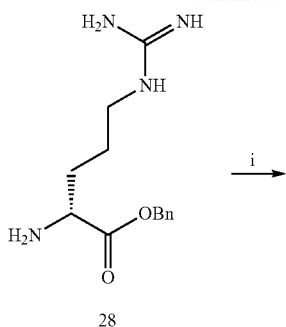
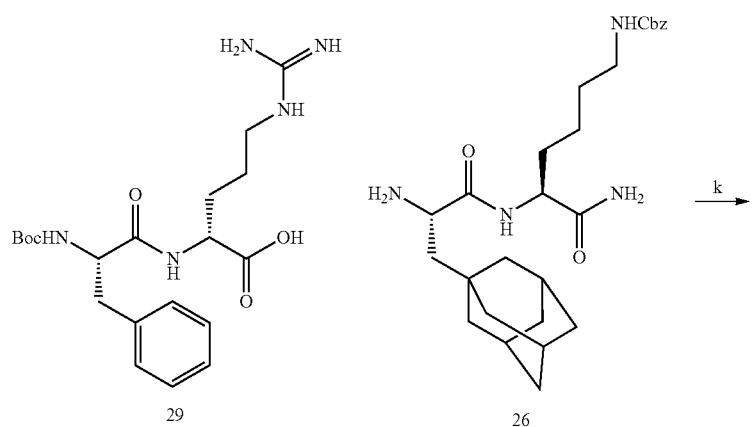
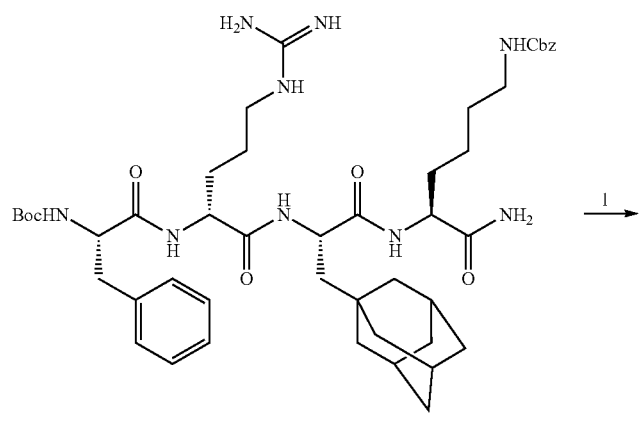
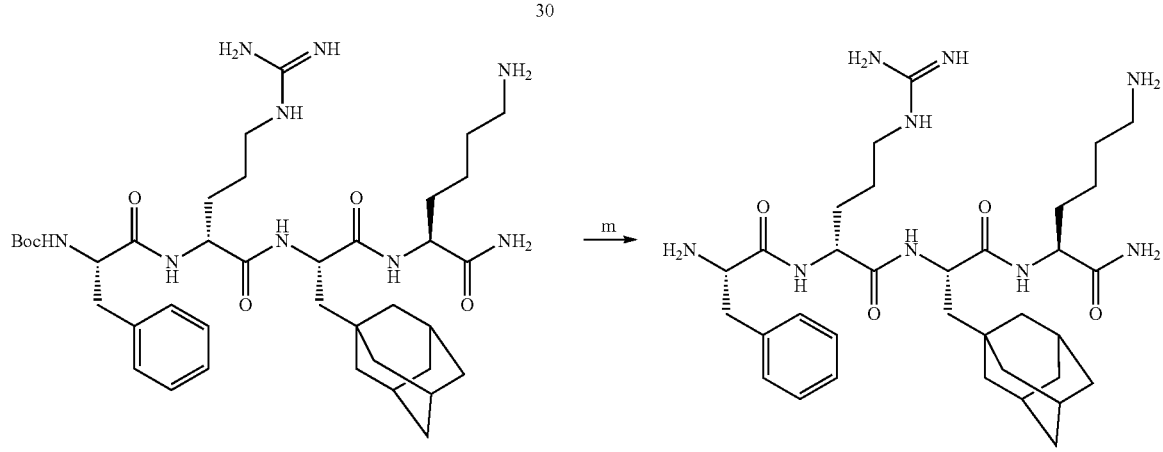

Step a: Synthesis of 2-(adamantan-1-yl)ethan-1-ol (17)

In a 5 L volume three necked flask equipped with stirrer, thermometer, 1-adamantyl acetic acid (16, 300 g, 1.53 mol), tetrahydrofuran (3 L) were charged, it was stirred with a stirrer and cooled to 5° C. Borane/THF complex (1 M THF solution, 2.6 L) was placed in a dropping funnel, it was added dropwise to the above solution. After the dropwise addition was completed, the mixture was stirred overnight while maintaining at 10° C. The reaction mixture was poured slowly into 3 L of ice water and the mixture was stirred for 30 minutes. After that, it was extracted three times with ethyl acetate (2 L), the ethyl acetate layer was washed with saturated aq. $NaHCO_3$ solution (2 L) and brine (2 L). The ethyl acetate layer after dried with anhydrous magnesium sulfate, the solvent was evaporated in vacuo to give a crude product, which was re-dissolved in 2 L water/methanol (10/90, v/v), and then concentrated to afford compound 17 (270 g, 97%) as white solid. $^1$H NMR (400 MHz, $CDCl_3$): δ 4.19-4.17 (t, J=4.0 Hz, 1H), 3.47-3.42 (m, 2H), 1.91-1.88 (m, 3H), 1.68-1.61 (m, 6H), 1.48-1.47 (m, 6H), 1.26-1.22 (m, 2H) ppm.

1) Step b: Synthesis of 2-(adamantan-1-yl)acetaldehyde (18)

An oven-dried three-necked flask was taken and filled with DCM (2 L) and DMSO (316 g, 4.04 mol). After cooling to −78° C., oxalyl chloride (270 g, 2.10 mol) was added dropwise and after addition the mixture was stirred for 15 min at −78° C. Subsequently, a solution of 1-adamantyl ethanol (17, 270 g, 1.50 mol) in DCM (2 L) was added dropwise to the reaction mixture. After stirring for 1 h at −78° C., $Et_3N$ (818 g, 8.09 mol) was added dropwise and after stirring further for 30 min, the reaction mixture was warmed to room temperature. Cold $NH_4Cl$ solution (2 L) and cold water (2 L) were added and the reaction mixture stirred for 15 min. The organic layer was washed with brine, dried over $Na_2SO_4$, filtered and concentrated to give the desired product 18 (265 g, crude) as a pale yellow oil. The product was immediately used for the next step without further purification. $^1$H NMR (400 MHz, $CDCl_3$): δ 9.79-9.78 (t, J=4.0 Hz, 1H), 2.11-2.10 (d, J=4.0 Hz, 2H), 1.95-1.92 (m, 3H), 1.70-1.59 (m, 12H) ppm.

2) Step c: Synthesis of (S)—N—((E)-2-(adamantan-1-yl)ethylidene)-2-methylpropane-2-sulfinamide (20)

Titanium tetraethoxide (700 g, 3.06 mol) was added to a stirred solution of 1-adamantyl acetaldehyde (18, 265 g, 1.49 mol) and (S)-tert-butanesulfinamide (19, 223 g, 1.84 mol) in THF (4 L) at room temperature under nitrogen atmosphere. The mixture was stirred at 15° C. for 12 h. TLC and HPLC indicated the reaction was completed. Then ethyl acetate (4 L) and water (4 L) was added. The reaction mixture was filtered through celite and the aqueous layer was extracted with ethyl acetate (2 L). The organic layer was concentrated and purified through silica gel column chromatography (PE/EtOAc=10/1) to afford the product 20 (350 g, 83%) as a white solid. $^1$H NMR (400 MHz, $CDCl_3$): δ 8.09-8.05 (t, J=6.0 Hz, 1H), 2.23-2.21 (m, 2H), 1.94-1.88 (m, 3H), 1.66-1.54 (m, 12H), 1.14 (s, 9H) ppm.

3) Step d: Synthesis of (S)—N—((S)-2-(adamantan-1-yl)-1-cyanoethyl)-2-methylpropane-2-sulfinamide (21)

To a mixture of compound 20 (350 g, 1.24 mol) and CsF (246 g, 1.62 mol) in THF (4 L) was added TMSCN (148 g, 1.49 mol). The reaction mixture was stirred at 25° C. for 12 h. TLC and HPLC indicated the reaction was completed. Cooled to −5° C. and quenched by addition of saturated aq. $NaHCO_3$ solution (2 L). The aqueous layer was extracted with ethyl acetate (2 L). The organic phases were washed with water and brine. The combined organic layers were dried over $Na_2SO_4$ and concentrated under reduced pressure. The resulting residue was dissolved in DCM (200 mL) and PE (2 L) was added. The mixture was stirred at room temperature for 1 h. The precipitates crashed out were filtered. The filter cake was washed with PE (500 mL), dried to give desired product 6 (150 g) as white solid. The filtrate was concentrated and purified by silica gel column chromatography (PE/EtOAc=2/1) to give a yellow oil (80 g), which was dissolved in DCM (80 mL) and then PE (800 mL) was added.

The mixture was stirred at room temperature for 1 h. The precipitates crashed out were filtered. The filter cake was washed with PE (300 mL), dried to give desired product 21 (62 g) as white solid. Total 212 g, yield: 55%, % ee>99%. $[α]^{21}_D$=34.61 (c=1, CHCl3). $^1$H NMR (400 MHz, $CDCl_3$): δ 4.25-4.19 (m, 1H), 3.61-3.59 (m, 1H), 2.06-1.98 (m, 3H), 1.75-1.61 (m, 14H), 1.27 (s, 9H) ppm.

4) Step e: Synthesis of (S)-3-(adamantan-1-yl)-2-aminopropanoic acid (22)

Compound 21 (50 g, 0.163 mol) was dissolved in 6 N HCl (5 L) and heated to reflux and stirred overnight (three batches were ran in parallel, totally 150 g compound 21). The reaction mixture was cooled on ice, resulting in precipitation of the product. The precipitates were collected by filtration, washed with ice-cold 6 N HCl and dried to afford the desired product 22 (108 g, yield: 85%) as a white solid. $^1$H NMR (400 MHz, $CD_3OD$): δ 4.02-3.99 (t, J=6.0 Hz, 1H), 2.05-1.98 (m, 3H), 1.90-1.85 (m, 1H), 1.81-1.59 (m, 12H), 1.53-1.47 (m, 1H) ppm.

5) Step f: Synthesis of (S)-3-(adamantan-1-yl)-2-((tert-butoxycarbonyl)amino)propanoic acid (23)

To a solution of adamantyl-alanine (22, 108 g, 0.415 mol) in $H_2O$ (500 mL) at 0° C. was added $K_2CO_3$ (115 g, 0.831 mol). After 10 min, $Boc_2O$ (181 g, 0.831 mol) in dioxane (1 L) was added dropwise. After stirring for 5 h, LC-MS analysis indicated complete consumption of the starting material. The reaction mixture was diluted with $H_2O$ (2 L) and acidified to pH=4 using 0.5 N HCl. The precipitates were collected by filtration to give the product (80 g, HPLC purity >98%, ee >98%). The filtrate was extracted with EtOAc (2×1 L). The combined organic layers were washed with brine (1 L), dried over $Na_2SO_4$ and concentrated to give a crude residue (45 g), which was dissolved in chloroform (125 mL) and PE (1.25 L) was added. The precipitates generated were collected by filtration, washed with PE and dried to afford 23 (22 g, HPLC purity >98%, ee>98%) as a white solid. Totally 102 g, yield: 76%. $^1$H NMR (400 MHz, $CDCl_3$): δ 5.37-5.35 (M, 0.17H), 4.77-4.55 (M, 0.74H), 4.36-4.33 (M, 0.78H), 4.18-4.16 (M, 0.19H), 1.91-1.88 (m, 3H), 1.71-1.55 (m, 13H), 1.44 (s, 9H), 1.34-1.28 (m, 1H) ppm.

6) Step g: Synthesis of (S)-3-(adamantan-1-yl)-2-aminopropanoic acid (25)

To a mixture of 23 (0.260 g, 0.804 mmol) and 24 (0.231 g, 0.731 mmol) in 5 mL of dry DCM EDCl·HCl (0.210 g, 1.096 mmol) was added followed by the addition of HOBt·H$_2$O (0.123 g, 0.804 mmol). After 10-15 min NMM (0.133 g, 1.316 mmol) was added and the mixture was stirred at ambient temperature overnight. Volatiles were removed under reduced pressure and the residue was washed with 5% of citric acid aqueous solution. Obtained white solid was purified by flash reversed-phase chromatography to afford 25 (0.320 g) as white solid. $^1$H NMR (400 MHz, Methanol-d$_4$) δ 7.34 (d, J=4.3 Hz, 4H), 7.29 (td, J=8.2, 4.0 Hz, 1H), 5.06 (s, 2H), 4.33 (dd, J=8.7, 5.0 Hz, 1H), 4.13 (dd, J=9.2, 3.0 Hz, 1H), 3.11 (t, J=6.9 Hz, 2H), 1.94 (s, 3H), 1.86-1.33 (m, 29H).

7) Step h: Synthesis of benzyl ((5S)-5-((2S)-3-(adamantan-1-yl)-2-((tert-butoxycarbonyl)amino)propanamido)-6-amino-6-oxohexyl)carbamate (26)

To a cooled solution of 25 (0.300 g, 0.513 mmol) in DCM (5 mL) TFA (2 mL) was added. Then ice/water bath was removed and the mixture was stirred at ambient temperature for 2 h. Volatiles were removed under reduced pressure and the residue was concentrated with toluene (2×). Purification by flash reversed-phase chromatography gave 0.200 g of 26 as white solid. $^1$H NMR (400 MHz, Methanol-d$_4$) δ 7.34 (d, J=4.5 Hz, 4H), 7.32-7.27 (m, 1H), 5.07 (s, 2H), 4.40 (dd, J=8.0, 6.0 Hz, 1H), 3.95 (dd, J=7.6, 5.4 Hz, 1H), 3.12 (t, J=6.9 Hz, 2H), 1.97 (s, 3H), 1.84 (dd, J=14.4, 7.7 Hz, 2H), 1.72 (q, J=12.0 Hz, 8H), 1.59 (d, J=2.7 Hz, 6H), 1.53 (q, J=7.1 Hz, 2H), 1.44 (dd, J=14.4, 5.4 Hz, 2H).

8) Step i: Synthesis of (tert-butoxycarbonyl)-L-phenylalanyl-D-arginine (29)

To a solution of Boc-Phe-ONp (27, 20.5 g, 52.94 mmol) in DMF (300 mL) D-Arg-OH*HCl (28, 9.30 g, 44.1 mmol) was added at room temperature. The reaction mixture was stirred overnight. Then reaction mixture was poured in ice-cold water and precipates (nitrophenol) was filtered off. The solvent was removed under reduced pressure. Yellow solid was washed with DCM until disappear of a color. After drying 16.0 g (yield—79%) of 29 was obtained. HPLC purity –98%. $^1$H NMR (400 MHz, Methanol-d$_4$) δ 7.31-7.19 (m, 5H), 4.30-4.20 (m, 2H), 3.20-3.10 (m, 3H), 2.80 (dd, J=9.0, 5.1 Hz, 1H), 1.87-1.81 (m, 1H), 1.73-1.64 (m, 1H), 1.53-1.45 (m, 2H), 1.35 (s, 9H).

9) Step j: Synthesis of tert-butyl ((9S,12S,15R,18S)-12-(adamantan-1-ylmethyl)-9-carbamoyl-15-(3-guanidinopropyl)-3,11,14,17-tetraoxo-1,19-diphenyl-2-oxa-4,10,13,16-tetraazanonadecan-18-yl)carbamate (30)

To a mixture of 26 (0.200 g, 0.384 mmol) and Boc-Phe-D-Arg-OH (29, 0.211 g, 0.461 mmol) in 5 mL of dry DCM EDCI·HCl (0.132 g, 0.691 mmol) was added followed by addition of HOBt·H$_2$O (0.071 g, 0.461 mmol) in one portion. After 10-15 min NMM (0.070 g, 0.691 mmol) was added and the mixture was stirred at ambient temperature overnight. After that volatiles were removed under reduced pressure. The residue was purified by flash reversed-phase chromatography to afford 30 (0.320 g) as white powder.

10) Step k: Synthesis of tert-butyl ((2S)-1-(((2R)-1-(((2S)-3-(adamantan-1-yl)-1-(((S)-1,6-diamino-1-oxohexan-2-yl)amino)-1-oxopropan-2-yl)amino)-5-guanidino-1-oxopentan-2-yl)amino)-1-oxo-3-phenylpropan-2-yl)carbamate (31)

To a cooled solution of 30 (0.245 g, 0.265 mmol) in DCM (5 mL) TFA (2 mL) was added. Then ice/water bath was removed and the mixture was stirred at ambient temperature for 2 h. Volatiles were removed under reduced pressure and the residue was concentrated with toluene (2×). Purification by flash reversed-phase chromatography and preparative HPLC gave 0.125 g of 31 as white solid.

11) Step 1: Synthesis of (2S)-2-((2S)-3-(adamantan-1-yl)-2-((R)-2-((S)-2-amino-3-phenylpropanamido)-5-guanidinopentanamido)propanamido)-6-aminohexanamide (15v)

To a flask containing 31 (0.100 g, 0.098 mmol) and Pd/C 10% w/w (0.016 g, 0.015 mmol) MeOH (10 mL) was added. The flask was flushed out with H$_2$ and the mixture was stirred for 2 h at RT. After that the mixture was filtered and volatiles were removed under reduced pressure. The residue was purified by preparative HPLC. 15v was obtained (48 mg) as white powder. (HPLC purity is 98.7% at 210 nm). $^1$H NMR (400 MHz, Methanol-d$_4$) δ 7.34-7.20 (m, 5H), 4.35 (d, J=14.5 Hz, 2H), 4.14 (dd, J=8.3, 6.2 Hz, 1H), 3.86 (t, J=7.5 Hz, 1H), 3.10 (td, J=7.1, 2.1 Hz, 2H), 3.06-2.97 (m, 2H), 2.93 (td, J=8.0, 2.9 Hz, 2H), 1.94 (s, 3H), 1.91-1.79 (m, 2H), 1.78-1.56 (m, 13H), 1.55-1.47 (d, J=9.5 Hz, 5H), 1.45-1.29 (m, 4H). MS: EI-MS: m/z 654.5 [M+1].

Example 23: Synthesis of (S)-6-amino-2-((S)-2-((R)-2-((S)-2-amino-3-phenylpropanamido)-5-guanidinopentanamido)-3-(perfluorophenyl)propanamido)hexanamide (Phe-D-Arg-(2,3,4,5,6-pentafluoro)-Phe-Lys-NH$_2$, 15w)

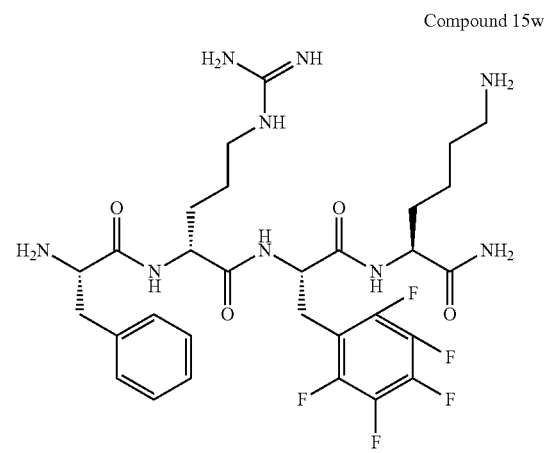 [SMILES: N=C(N)NCCC[C@@H](NC(=O)[C@@H](N)Cc1ccccc1)C(=O)N[C@@H](Cc1c(F)c(F)c(F)c(F)c1F)C(=O)N[C@@H](CCCCN)C(N)=O]

Compound 15w

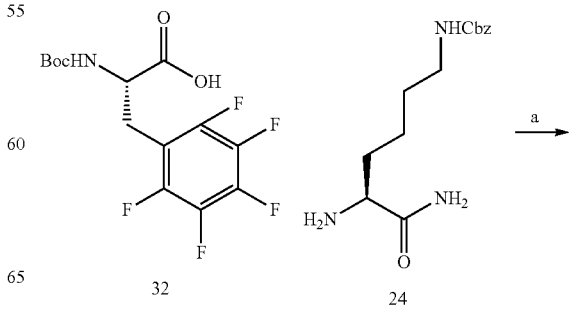

Scheme 3

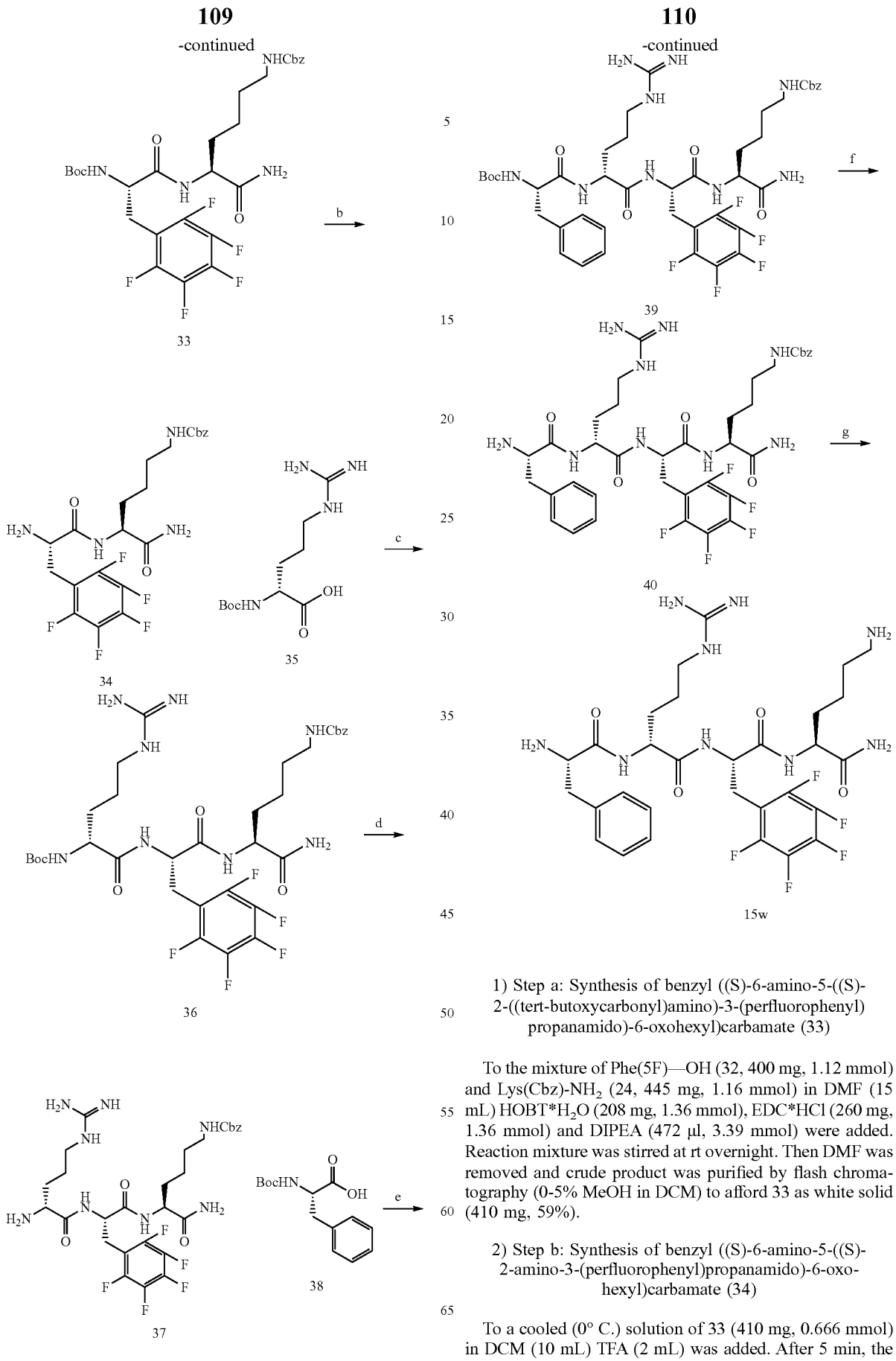

1) Step a: Synthesis of benzyl ((S)-6-amino-5-((S)-2-((tert-butoxycarbonyl)amino)-3-(perfluorophenyl)propanamido)-6-oxohexyl)carbamate (33)

To the mixture of Phe(5F)—OH (32, 400 mg, 1.12 mmol) and Lys(Cbz)-NH₂ (24, 445 mg, 1.16 mmol) in DMF (15 mL) HOBT*H₂O (208 mg, 1.36 mmol), EDC*HCl (260 mg, 1.36 mmol) and DIPEA (472 µl, 3.39 mmol) were added. Reaction mixture was stirred at rt overnight. Then DMF was removed and crude product was purified by flash chromatography (0-5% MeOH in DCM) to afford 33 as white solid (410 mg, 59%).

2) Step b: Synthesis of benzyl ((S)-6-amino-5-((S)-2-amino-3-(perfluorophenyl)propanamido)-6-oxohexyl)carbamate (34)

To a cooled (0° C.) solution of 33 (410 mg, 0.666 mmol) in DCM (10 mL) TFA (2 mL) was added. After 5 min, the ice bath was removed and the mixture stirred at ambient temperature for 2 h. Volatiles were removed under reduced pressure and the residue concentrated twice with toluene. 34 (460 mg) was obtained as white solid that was used without further purification.

3) Step c: Synthesis of benzyl ((6R,9S,12S)-12-carbamoyl-6-(3-guanidinopropyl)-2,2-dimethyl-4,7,10-trioxo-9-((perfluorophenyl)methyl)-3-oxa-5,8,11-triazahexadecan-16-yl)carbamate (36)

To the mixture of 34 (200 mg, 0.318 mmol) and Boc-D-Arg-OH (35, 83 mg, 0.325 mmol) in DMF (15 mL) HOBT*H₂O (58.4 mg, 0.382 mmol), EDC*HCl (121 mg, 0.336 mmol) and DIPEA (187 µl, 1.59 mmol) were added. Reaction mixture was stirred at rt overnight. Then DMF was removed and crude product was purified by flash chromatography (0-10% MeOH in DCM) to afford 36 as white solid (180 mg, 72%).

4) Step d: Synthesis of benzyl ((S)-6-amino-5-((S)-2-((R)-2-amino-5-guanidinopentanamido)-3-(perfluorophenyl)propanamido)-6-oxohexyl)carbamate (37)

To a cooled (0° C.) solution of 36 (175 mg, 0.222 mmol) in DCM (5 mL) TFA (1 mL) was added. After 5 min, the ice bath was removed and the mixture stirred at ambient temperature for 2 h. Volatiles were removed under reduced pressure and the residue concentrated twice with toluene. 37 (210 mg) was obtained as white solid that was used without further purification.

5) Step e: Synthesis of benzyl ((6S,9R,12S,15S)-6-benzyl-15-carbamoyl-9-(3-guanidinopropyl)-2,2-dimethyl-4,7,10,13-tetraoxo-12-((perfluorophenyl)methyl)-3-oxa-5,8,11,14-tetraazanonadecan-19-yl)carbamate (39)

To the mixture of 37 (210 mg, 0.229 mmol) and Boc-Phe-OH (38, 62 mg, 0.230 mmol) in DMF (15 mL) HOBT*H₂O (42.0 mg, 0.382 mmol), EDC*HCl (88 mg, 0.458 mmol) and DIPEA (160 µl, 1.45 mmol) were added. Reaction mixture was stirred at rt overnight. Then DMF was removed and crude product was purified by flash chromatography (0-15% MeOH in DCM) to afford 39 as white solid (220 mg).

6) Step f: Synthesis of benzyl ((S)-6-amino-5-((S)-2-((R)-2-((S)-2-amino-3-phenylpropanamido)-5-guanidinopentanamido)-3-(perfluorophenyl)propanamido)-6-oxohexyl)carbamate (40)

To a cooled (0° C.) solution of 39 (215 mg, 0.189 mmol) in DCM (5 mL) TFA (1.0 mL) was added. After 5 min, the ice bath was removed and the mixture stirred at ambient temperature for 2 h. Volatiles were removed under reduced pressure and the residue concentrated twice with toluene. 40 (220 mg) was obtained as yellowish oil that was used without further purification.

7) Step g: Synthesis of (S)-6-amino-2-((S)-2-((R)-2-((S)-2-amino-3-phenylpropanamido)-5-guanidinopentanamido)-3-(perfluorophenyl)propanamido) hexanamide (15w)

To a solution of 40 (210 mg, 0.200 mmol) in MeOH (7 mL) Pd/C (10% w/w, 15 mg) was bubbled with hydrogen at room temperature for 3 h. Then reaction mixture was filtrated through Celite pad and washed with MeOH (10 mL). The solvent was removed by evaporation. It was obtained 150 mg white solid. Purification was performed by HPLC. 15w was isolated as a white solid (49 mg, impurities <5%). ¹H NMR (400 MHz, Methanol-d₄) δ 7.38-7.24 (m, 5H), 4.55 (dd, J=8.9, 6.4 Hz, 1H), 4.38 (dd, J=8.6, 5.5 Hz, 1H), 4.13-4.05 (m, 2H), 3.34 (dd, J=14.0, 6.1 Hz, 1H), 3.15-3.00 (m, 5H), 2.95-2.89 (m, 2H), 1.89-1.34 (m, 8H), 1.28-1.12 (m, 2H). MS: EI-MS: m/z 686.6 [M+1].

Example 24: Synthesis of (2S)-2-((2S)-2-((2R)-2-((2S)-3-(adamantan-1-yl)-2-aminopropanamido)-5-guanidinopentanamido)-3-phenylpropanamido)-6-aminohexanamide ((β-Admantan-1-yl)-Ala-D-Arg-Phe-Lys-NH₂, 15x)

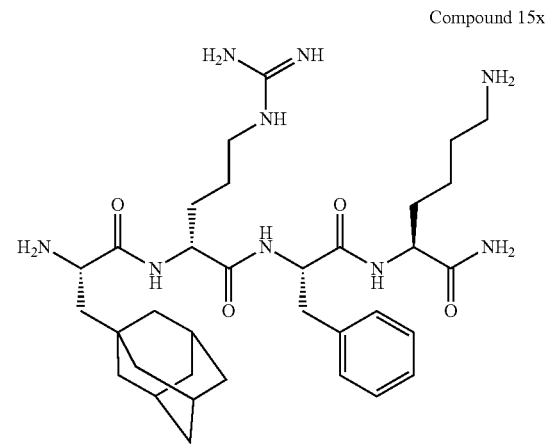 [SMILES: N=C(N)NCCC[C@@H](NC(=O)[C@@H](N)CC12CC3CC(CC(C3)C1)C2)C(=O)N[C@@H](Cc1ccccc1)C(=O)N[C@@H](CCCCN)C(N)=O]

Compound 15x

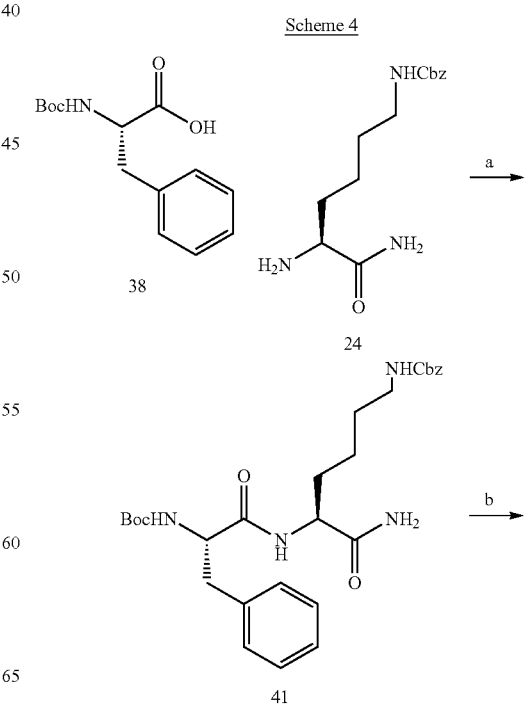

Scheme 4

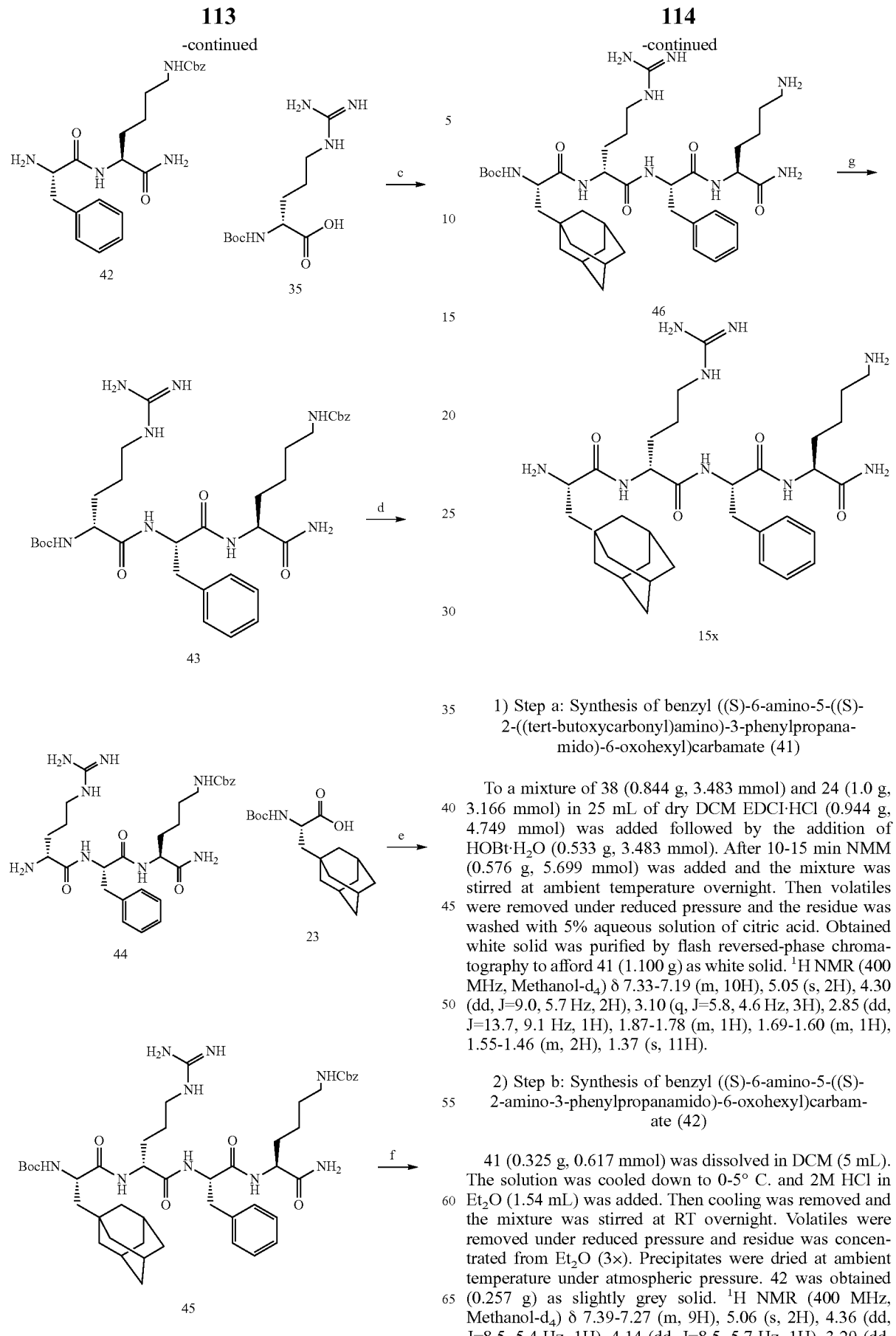

1) Step a: Synthesis of benzyl ((S)-6-amino-5-((S)-2-((tert-butoxycarbonyl)amino)-3-phenylpropanamido)-6-oxohexyl)carbamate (41)

To a mixture of 38 (0.844 g, 3.483 mmol) and 24 (1.0 g, 3.166 mmol) in 25 mL of dry DCM EDCI·HCl (0.944 g, 4.749 mmol) was added followed by the addition of HOBt·H₂O (0.533 g, 3.483 mmol). After 10-15 min NMM (0.576 g, 5.699 mmol) was added and the mixture was stirred at ambient temperature overnight. Then volatiles were removed under reduced pressure and the residue was washed with 5% aqueous solution of citric acid. Obtained white solid was purified by flash reversed-phase chromatography to afford 41 (1.100 g) as white solid. ¹H NMR (400 MHz, Methanol-d₄) δ 7.33-7.19 (m, 10H), 5.05 (s, 2H), 4.30 (dd, J=9.0, 5.7 Hz, 2H), 3.10 (q, J=5.8, 4.6 Hz, 3H), 2.85 (dd, J=13.7, 9.1 Hz, 1H), 1.87-1.78 (m, 1H), 1.69-1.60 (m, 1H), 1.55-1.46 (m, 2H), 1.37 (s, 11H).

2) Step b: Synthesis of benzyl ((S)-6-amino-5-((S)-2-amino-3-phenylpropanamido)-6-oxohexyl)carbamate (42)

41 (0.325 g, 0.617 mmol) was dissolved in DCM (5 mL). The solution was cooled down to 0-5° C. and 2M HCl in Et₂O (1.54 mL) was added. Then cooling was removed and the mixture was stirred at RT overnight. Volatiles were removed under reduced pressure and residue was concentrated from Et₂O (3×). Precipitates were dried at ambient temperature under atmospheric pressure. 42 was obtained (0.257 g) as slightly grey solid. ¹H NMR (400 MHz, Methanol-d₄) δ 7.39-7.27 (m, 9H), 5.06 (s, 2H), 4.36 (dd, J=8.5, 5.4 Hz, 1H), 4.14 (dd, J=8.5, 5.7 Hz, 1H), 3.29 (dd, J=14.4, 5.6 Hz 1H), 3.11 (t, J=6.9 Hz, 2H), 3.03 (dd, J=14.3, 8.5 Hz, 1H), 1.87-1.78 (m, 1H), 1.74-1.65 (m, 1H), 1.52 (h, J=7.7, 7.3 Hz, 2H), 1.46-1.34 (m, 2H).

3) Step c: Synthesis of benzyl ((6R,9S,12S)-9-benzyl-12-carbamoyl-6-(3-guanidinopropyl)-2,2-dimethyl-4,7,10-trioxo-3-oxa-5,8,11-triazahexadecan-16-yl)carbamate (43)

To a mixture of 42 (0.220 g, 0.475 mmol) and Boc-D-Arg (35, 0.163 g, 0.523 mmol) in 10 mL of dry DCM EDCI·HCl (0.137 g, 0.713 mmol) was added followed by the addition of HOBt·H$_2$O (0.080 g, 0.523 mmol). After 10-15 min NMM (0.106 g, 1.045 mmol) was added and the mixture was stirred at ambient temperature overnight. Then volatiles were removed under reduced pressure. The residue was purified by flash reversed-phase chromatography to afford 43 (0.170 g) as white solid. $^1$H NMR (400 MHz, Methanol-d$_4$) δ 7.34-7.20 (m, 10H), 5.06 (s, 2H), 4.63 (dd, J=10.0, 4.6 Hz, 1H), 4.29 (dd, J=9.8, 4.6 Hz, 1H), 3.92 (t, J=7.0 Hz, 1H), 3.29 (dd, J=10.8, 4.5 Hz, 1H), 3.12 (t, J=6.4 Hz, 2H), 3.03-2.99 (m, 2H), 2.90 (dd, J=13.9, 10.3 Hz, 1H), 1.94-1.85 (m, 1H), 1.81-1.70 (m, 1H), 1.60-1.47 (m, 7H), 1.41 (s, 9H) 1.23-1.14 (m, 1H).

4) Step d: Synthesis of benzyl ((S)-6-amino-5-((S)-2-((R)-2-amino-5-guanidinopentanamido)-3-phenylpropanamido)-6-oxohexyl)carbamate (44)

To a cooled solution of 43 (0.170 g, 0.236 mmol) in DCM (5 mL) TFA (2 mL) was added. Then ice/water bath was removed and the mixture was stirred at ambient temperature for 2 h. Volatiles were removed under reduced pressure and the residue was concentrated from toluene (2×). Purification by reverse-phase flash chromatography gave 0.140 g of 44 as white solid. $^1$H NMR (400 MHz, Methanol-d$_4$) δ 7.34-7.21 (m, 10H), 5.06 (s, 2H), 4.75 (dd, J=10.8, 4.9 Hz, 1H), 4.35 (dd, J=9.3, 5.0 Hz, 1H), 3.85 (t, J=6.4 Hz, 1H), 3.30-3.25 (m, 1H), 3.16-3.10 (m, 2H), 2.97 (t, J=7.0 Hz, 2H), 2.88 (dd, J=13.9, 11.0 Hz, 1H), 1.88-1.79 (m, 1H), 1.74-1.58 (m, 3H), 1.57-1.36 (m, 4H), 1.25-1.14 (m, 2H).

5) Step e: Synthesis of benzyl ((6S,9R,12S,15S)-6-(adamantan-1-ylmethyl)-12-benzyl-15-carbamoyl-9-(3-guanidinopropyl)-2,2-dimethyl-4,7,10,13-tetraoxo-3-oxa-5,8,11,14-tetraazanonadecan-19-yl)carbamate (45)

To a mixture of 44 (0.140 g, 0.213 mmol) and 23 (0.090 g, 0.277 mmol) in 5 mL of dry DCM EDCI·HCl (0.073 g, 0.383 mmol) was added followed by the addition of HOBt·H$_2$O (0.039 g, 0.256 mmol). After 10-15 min NMM (0.039 g, 0.383 mmol) was added and the mixture was stirred at ambient temperature overnight. Then volatiles were removed under reduced pressure and the residue 45 was flushed thoroughly reverse-phase flash column and used in next step without further purification.

6) Step f: Synthesis of tert-butyl ((2S)-3-(adamantan-1-yl)-1-(((R)-1-(((S)-1-(((S)-1,6-diamino-1-oxohexan-2-yl)amino)-1-oxo-3-phenylpropan-2-yl)amino)-5-guanidino-1-oxopentan-2-yl)amino)-1-oxopropan-2-yl)carbamate (46)

To a cooled solution of 45 (0.105 g, 0.114 mmol) in DCM (5 mL) was added TFA (2 mL). Then ice/water bath was removed and the mixture was stirred at ambient temperature for 2 h. Volatiles were removed under reduced pressure and the residue was concentrated from toluene (2×). Purification by reverse-phase flash chromatography and preparative HPLC gave 0.065 g of 46 as white solid. $^1$H NMR (400 MHz, Methanol-d$_4$) δ 7.31-7.18 (m, 10H), 5.04 (s, 2H), 4.65 (dd, J=11.2, 4.0 Hz, 1H), 4.38 (dd, J=8.9, 5.5 Hz, 1H), 4.08 (t, J=7.2 Hz, 1H), 3.96-3.89 (m, 1H), 3.39 (dd, J=14.1, 3.7 Hz, 1H), 3.18-3.08 (m, 2H), 3.01-2.93 (m, 2H), 2.78 (dd, J=14.0, 11.5 Hz, 1H), 1.92 (s, 3H), 1.86-1.78 (m, 3H), 1.73-1.62 (m, 6H), 1.56-1.34 (m, 12H), 1.34-1.20 (m, 2H), 1.03-0.91 (m, 1H).

7) Step g: Synthesis of (2S)-2-((2S)-2-((2R)-2-((2S)-3-(adamantan-1-yl)-2-aminopropanamido)-5-guanidinopentanamido)-3-phenylpropanamido)-6-aminohexanamide (15x)

To a flask containing 46 (0.064 g, 0.065 mmol) and Pd/C 10% w/w (0.010 g, 0.010 mmol) MeOH (5 mL) was added. The flask was flushed out with H$_2$ and the mixture was stirred for 2 h at RT. Then the mixture was filtered and volatiles were removed under reduced pressure. The residue was purified on preparative HPLC yielding 52 mg of 15x as white solid (HPLC purity is 95.4% at 210 nm). $^1$H NMR (400 MHz, Methanol-d$_4$) δ 7.31-7.20 (m, 5H), 4.66 (dd, J=11.3, 4.3 Hz, 1H), 4.43 (dd, J=8.9, 5.5 Hz, 1H), 4.15 (t, J=7.4 Hz, 1H), 3.95 (dd, J=8.6, 4.6 Hz, 1H), 3.39 (dd, J=14.1, 4.2 Hz, 1H), 3.05-2.95 (m, 4H), 2.86 (dd, J=14.1, 11.3 Hz, 1H), 1.95 (s, 3H), 1.90-1.80 (m, 3H), 1.76-1.64 (m, 8H), 1.59-1.43 (m, 10H), 1.37-1.29 (m, 2H), 1.13-1.02 (m, 1H). MS: EI-MS: m/z 654.8 [M+1].

Example 25: Synthesis of (S)-6-amino-2-((S)-2-((R)-2-((S)-2-amino-3-phenylpropanamido)-5-guanidinopentanamido)-3-(bicyclo[2.2.2]octan-1-yl)propanamido)hexanamide (Phe-D-Arg-(A-bicyclo[2.2.2]octan-1-yl)-Ala-Lys-NH$_2$, 15y)

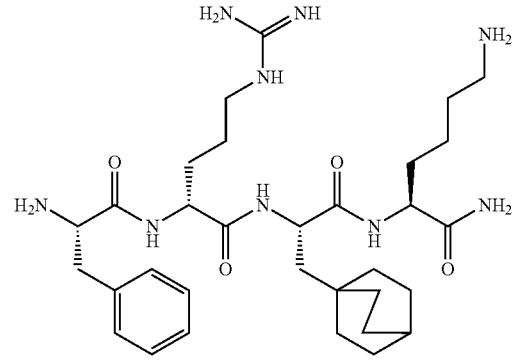

Compound 15y

Scheme 5
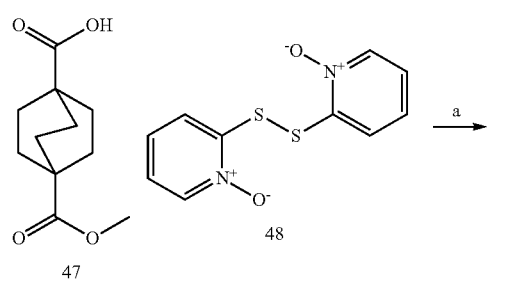
47  48
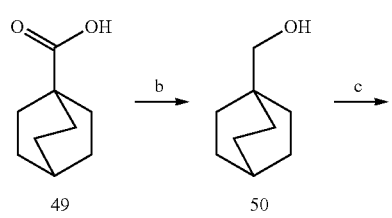
49  50
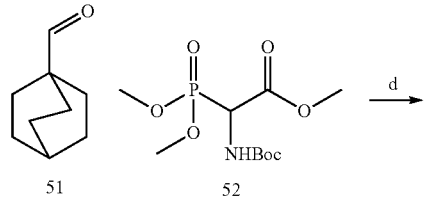
51  52
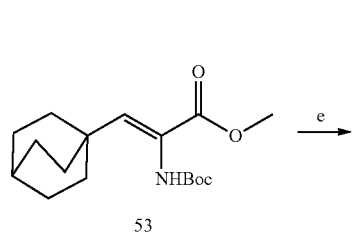
53
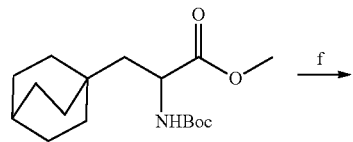
54
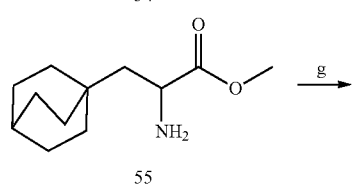
55
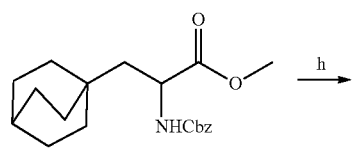
56
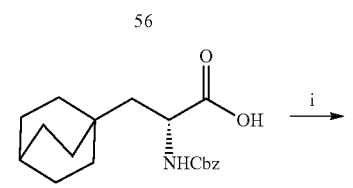
57
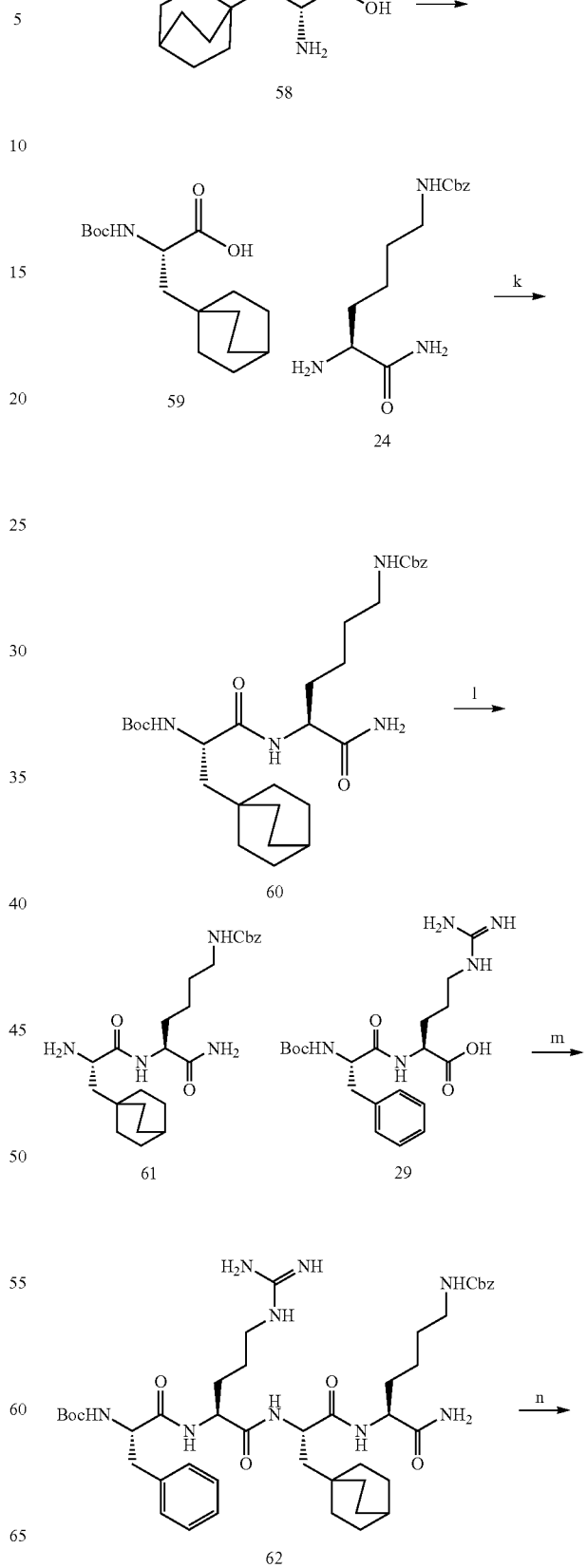
58
59  24
60
61  29
62

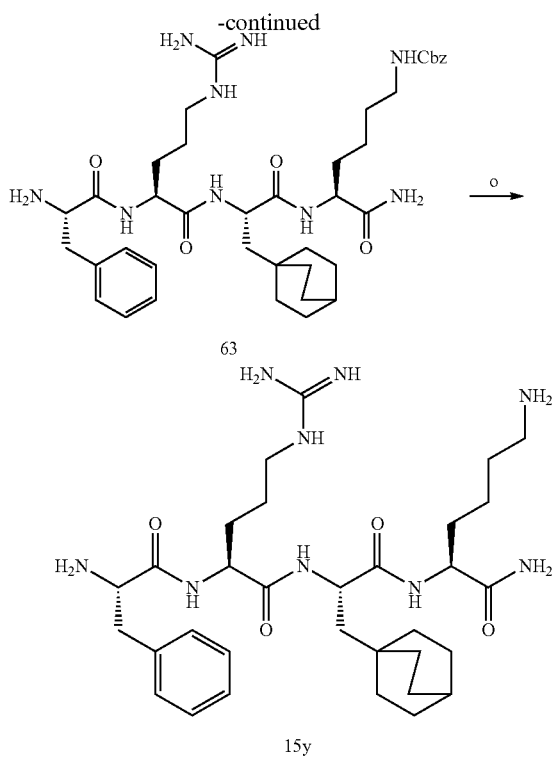

1) Step a: Synthesis of bicyclo[2.2.2]octane-1-carboxylic acid (49)

A flask was charged with 47 (35 g, 165 mmol), 48 (50.0 g, 198 mmol), and DCM (1.5 L). The flask was masked with foil to reduce ambient light. The resulting suspension was cooled to 0° C. and treated with tributylphosphine (51 mL, 206 mmol) drop wise. The ice bath was removed and stirring continued for 2 h. The reaction was cooled to 0° C. and treated with 2-methylpropane-2-thiol (165 mL, 1.46 mol). The reaction was irradiated with a 300 W Tungstern lamp for 1.25 h. The reaction was quenched by addition of a suspension of 350 g calcium hypochlorite in water (2.0 L). The mixture was diluted with ether and stirred at 0° C. for 5 min, followed by room temperature for 20 min. Celite was added to aid in separation of the layers, and the resulting mixture filtered. The eluent was poured into a separatory funnel and the layers separated. The organics were washed with brine, dried over $Na_2SO_4$, and concentrated. The resulting residue was treated with a solution of 75 g potassium hydroxide in 1.0 L methanol/water (1:1). The resulting mixture was stirred at room temperature overnight. The reaction was concentrated to remove most of the methanol and extracted with EtOAc (500 mL×2) to remove byproducts. The aqueous was made acidic by addition of con.HCl upon which a white precipitate was formed. The precipitate was collected by filtration to afford 49 (21 g, 83%). $^1$H NMR (300 MHz, DMSO-$d_6$), δ=1.60 (m, 13H).

2) Step b: Synthesis of bicyclo[2.2.2]octan-1-ylmethanol (50)

To a solution of 49 (21 g, 136 mmol) in THF (300 mL) at 0° C. was added LAH (7.7 g, 198 mmol) by portions. When the addition was completed, the reaction mixture was heated to reflux for 3 h, cooled to room temperature, and re-cooled to 0° C., quenched by 5% NaOH (5 mL) and 10 mL of water, $Na_2SO_4$ (50 g) was added, filtered by celite and the filtrate was concentrated in vacuo to give the crude product, purification by column chromatography (SiO$_2$, 100-200, eluted by PE/EtOAc=30:1) to afford the desired product as a white solid (50, 10.5 g, 54%). $^1$H NMR (300 MHz, DMSO-$d_6$), δ=4.27 (br, 1H), 2.97 (m, 2H), 1.49 (m, 7H), 1.17 (m, 6H).

3) Step c: Synthesis of bicyclo[2.2.2]octane-1-carbaldehyde (51)

Oxalyl chloride (1.8 g, 13 mmol) in 35 mL of anhydrous dichloromethane was cooled to −70° C.; DMSO (2.3 g, 30 mmol) in 30 mL of DCM was added. The mixture was stirred for 30 min at that temperature, before 50 (1.8 g, 13 mmol) in 20 mL of DCM and 1 mL of DMSO was added dropwise. During 3 h the mixture was warmed to −30° C. Et$_3$N (5.1 g, 52 mol) was added; the temperature raised to 0° C. over one hour. The reaction was quenched with 60 mL of water. The organic layer was separated, washed with water, treated with active charcoal, and dried over $Na_2SO_4$. The solvent was removed under reduced pressure to give the desired product (51, 10.0 g, crude) as colorless oil. $^1$H NMR (300 MHz, DMSO-$d_6$), δ=9.36 (s, 1H), 1.61 (s, 1H), 1.52 (m, 12H).

4) Step d: Synthesis of methyl (Z)-3-(bicyclo[2.2.2]octan-1-yl)-2-((tert-butoxycarbonyl)amino)acrylate (53)

To a solution of 51 (10 g, 72.5 mmol) and 52 (32.3 g, 108 mmol) in $CH_2Cl_2$ (50 mL) was added 1,1,3,3-Tetramethylguanidine (12.4 g, 108 mmol), when the addition was completed, the reaction mixture was stirred at room temperature for 24 h, the resulting mixture was quenched by 50 mL water, diluted by DCM 50 mL, separated the organic layer, washed with brine, dried over $Na_2SO_4$, filtered and purified by (SiO$_2$, 100-200 m, eluted by hexane/EtOAc, 10:1) to give 53 (12 g, 55%) as white solid. $^1$H NMR (300 MHz, DMSO-$d_6$), δ=8.16 (m, 1H), 6.19 (m, 1H), 3.61 (m, 3H), 1.20-1.60 (m, 22H).

5) Step e: Synthesis of methyl 3-(bicyclo[2.2.2]octan-1-yl)-2-((tert-butoxycarbonyl)amino)propanoate (54)

To a solution of 53 (12 g, 39 mmol) and Pd(OAc)$_2$ (1.2 g) in MeOH (100 mL) was purged three times with H$_2$ gas at 6 atm, then stirred at room temperature overnight. Filtered by celite and the filtrate was concentrated in vacuo to give the desired product as a white solid (54, 9.7 g, 81%).

6) Step f: Synthesis of methyl 2-amino-3-(bicyclo[2.2.2]octan-1-yl)propanoate (55)

A solution of 54 (9.7 g, 31.2 mmol) in 4 N HCl/Dioxane (100 mL) was stirred at room temperature for 2 h, the reaction mixture was concentrated in vacuo to give the desired product as white solid (55, 7.7 g, crude).

7) Step g: Synthesis of methyl 2-(((benzyloxy)carbonyl)amino)-3-(bicyclo[2.2.2]octan-1-yl)propanoate (56)

To a solution of compound 55 (7.7 g, 31 mmol) in water (100 mL) and EtOAc (100 mL) at 0° C. was added $K_2CO_3$ (8.5 g, 62 mmol) slowly, then CbzCl (4.9 mL, 34.1 mmol) was added dropwise with controlling the temperature at 0° C. 5° C., when the additional was completed, the reaction mixture was stirred at 0° C. for 1 h, LCMS showed no starting materials left, separated the organic layer, washed by brine, dried over $Na_2SOI$, filtered and purification by silica gel column chromatography (SiO2, 100-200 m, eluted by PE/EtOAc=3:1) gave the desired product as a white solid (56, 6.5 g, 61%). $^1$H NMR (300 MHz, $CDCl_3$), δ=7.35 (m, 5H), 5.15 (m, 2H), 4.90 (m, 1H), 4.45 (m, 1H), 1.20-1.70 (m, 15H). MS: $(M+H)^+$: 346.2.

8) Step h: Synthesis of (S)-2-(((benzyloxy)carbonyl)amino)-3-(bicyclo[2.2.2]octan-1-yl)propanoic acid (57)

To a solution of compound 56 (6.5 g, 18.8 mmol) in MeOH (25 mL) and THF (25 mL) was added 2N NaOH (25 mL), then the mixture was stirred at room temperature for 2 h, concentrated in vacuo to remove the most of MeOH and THF, cooled to 0° C., neutralized by 2N·HCl to pH=3~4, extracted by EtOAc (50 mL×2), washed by brine, dried over $Na_2SO_4$, filtered and concentrated in vacuo to remove the solvent, 50 nL of $PE/Et_2O$ (5.1) was added into the residue with stirring, the white solid was formed, it was filtered and washed by $PE/Et_2O$ (10 mL, 5:1), dried in vacuo to give the desired product as a white solid (5.8 g, 94%), chiral HPLC separation to give 57a and 57b.

57a: $^1$H NMR (300 MHz, DMSO-$d_6$), δ=7.55 (m, 1H), 7.40 (m, 5H), 5.15 (s, 2H), 4.04 (m, 1H), 1.20-1.50 (m, 15H).

57b: $^1$H NMR (300 MHz, DMSO-$d_6$), δ=7.52 (m, 1H), 7.35 (m, 5H), 5.04 (s, 2H), 4.00 (m, 1H), 1.20-1.50 (m, 15H).

9) Step i: Synthesis of (S)-2-amino-3-(bicyclo[2.2.2]octan-1-yl)propanoic acid (58)

The same procedure as described in Scheme 4 to give 58.

10) Step j: Synthesis of (S)-3-(bicyclo[2.2.2]octan-1-yl)-2-((tert-butoxycarbonyl)amino)propanoic acid (59)

To a suspension of 58 (200 mg, 0.856 mmol) in $H_2O$ (5 mL) $Na_2CO_3$ (190 mg, 1.80 mmol) was added at 0° C., then $Boc_2O$ (373 mg, 1.71 mmol) in 3 mL dioxane. Then additional water and dioxane (total volume of reaction mixture 20 mL) was added and pH increased till pH=9 with aq. Solution of $Na_2CO_3$. The reaction mixture was stirred overnight at RT, then acidified with 10% HCl until pH 3 and extracted with EtOAc (3×). The organic phase was separated, washed with sat. NaCl and water, dried over anh. $Na_2SO_4$, filtered and evaporated. The crude product 59 was evaporated with toluene and used in the next step without further purification.

11) Step k: Synthesis of tert-butyl ((S)-1-(((S)-1-amino-6-(((benzyloxy)carbonyl)amino)-1-oxohexan-2-yl)amino)-3-(bicyclo[2.2.2]octan-1-yl)-1-oxopropan-2-yl)carbamate (60)

To a mixture of crude product (59, 254 mg, 0.856 mmol), NE-Cbz-L-lysine hydrochloride (24, 270 mg, 0.856 mmol), HOBt monohydrate (262 mg, 1.71 mmol), EDC hydrochloride (328 mg, 1.71 mmol) in DMF (5 mL) NMM (0.47 mL, 4.28 mmol) was added at 0° C. After 5 min ice bath was removed and the reaction mixture was stirred overnight at RT, then evaporated and purified by flash column chromatography (eluent $H_2O$ (0.1% AcOH)/MeOH). 300 mg (63%) of 60 were isolated. $^1$H NMR (400 MHz, Methanol-$d_4$) δ 7.35-7.29 (m, 5H), 5.06 (s, 2H), 4.33-4.30 (m, 1H), 4.09-4.05 (m, 1H), 3.12-3.08 (m, 2H), 1.83-1.31 (multiple peaks, 26H).

12) Step 1: Synthesis of benzyl ((S)-6-amino-5-((S)-2-amino-3-(bicyclo[2.2.2]octan-1-yl)propanamido)-6-oxohexyl)carbamate (61)

To a solution of 60 (198 mg, 0.354 mmol) in DCM (8 mL) was added TFA (3 mL) at 0° C. After 5 min ice bath was removed and the reaction mixture was stirred 30 min at ambient temperature. The volatiles were evaporated, and then crude 61 was evaporated with toluene and used in the next step without purification.

13) Step m: Synthesis of benzyl ((6S,9S,12S,15S)-6-benzyl-12-(bicyclo[2.2.2]octan-1-ylmethyl)-15-carbamoyl-9-(3-guanidinopropyl)-2,2-dimethyl-4,7,10,13-tetraoxo-3-oxa-5,8,11,14-tetraazanonadecan-19-yl)carbamate (62)

To a mixture of 61 (203 mg, 0.354 mmol), 29 (149 mg, 0.354 mmol), HOBt monohydrate (81 mg, 0.531 mmol), EDC hydrochloride (102 mg, 0.531 mmol) in DMF (2 mL) NMM (0.12 mL, 1.06 mmol) was added at 0° C. After 5 min ice bath was removed and the reaction mixture was stirred 1 day at RT, then evaporated and purified by flash column chromatography (eluent $H_2O$ (0.1% AcOH)/MeOH). 130 mg of crude product 62 were isolated and used in the next step.

14) Step n: Synthesis of benzyl ((S)-6-amino-5-((S)-2-((S)-2-((S)-2-amino-3-phenylpropanamido)-5-guanidinopentanamido)-3-(bicyclo[2.2.2]octan-1-yl)propanamido)-6-oxohexyl)carbamate (63)

To a solution of crude product (62, 130 mg, 0.151 mmol) in DCM (3 mL) TFA (1.5 mL) was added at 0° C. After 5 min ice bath was removed and the reaction mixture was stirred 30 min at ambient temperature. The volatiles were evaporated, and then crude product was purified by preparative HPLC. 50 mg of 63 were isolated. $^1$H NMR (400 MHz, Methanol-$d_4$) δ 7.39-7.27 (m, 10H), 5.07 (s, 2H), 4.33-4.30 (m, 1H), 4.39-4.32 (m, 2H), 4.19-4.12 (m, 2H), 3.22-3.07 (m, 6H), 1.84-1.29 (multiple peaks, 25H).

15) Step o: Synthesis of (S)-6-amino-2-((S)-2-((S)-2-((S)-2-amino-3-phenylpropanamido)-5-guanidinopentanamido)-3-(bicyclo[2.2.2]octan-1-yl)propanamido)hexanamide (15y)

To a solution of 63 (50 mg, 0.066 mmol) in MeOH (3 mL) was added cat. amount of 10% Pd/C. The reaction mixture was evacuated and backfilled with hydrogen (×8, balloon), then stirred overnight at room temperature. The crude product was filtered through 45 μm filter, evaporated and purified by preparative HPLC. As a result, 15 mg of 15y were isolated as a white solid. $^1$H NMR (400 MHz, Methanol-$d_4$) δ 8.73 (br d, J=7.6 Hz, 1H), 7.76 (br d, J=8.8 Hz, 1H), 7.42-7.30 (m, 5H), 4.45-4.33 (multiple peaks, 2H), 4.24-4.16 (multiple peaks, 2H), 3.19-3.13 (multiple peaks, 4H), 2.99-2.94 (m, 2H), 1.93-1.19 (multiple peaks, 21H). MS: EI-MS: m/z 628.7 [M+1].

Example 26: Synthesis of (S)-6-amino-2-((S)-2-((R)-2-((S)-2-amino-3-(bicyclo[1.1.1]pentan-1-yl)propanamido)-5-guanidinopentanamido)-3-phenyl-propanamido)hexanamide ((β-bicyclo[1.1.1]pentan-1-yl)-Ala-D-Arg-Phe-Lys-NH$_2$, 15z)

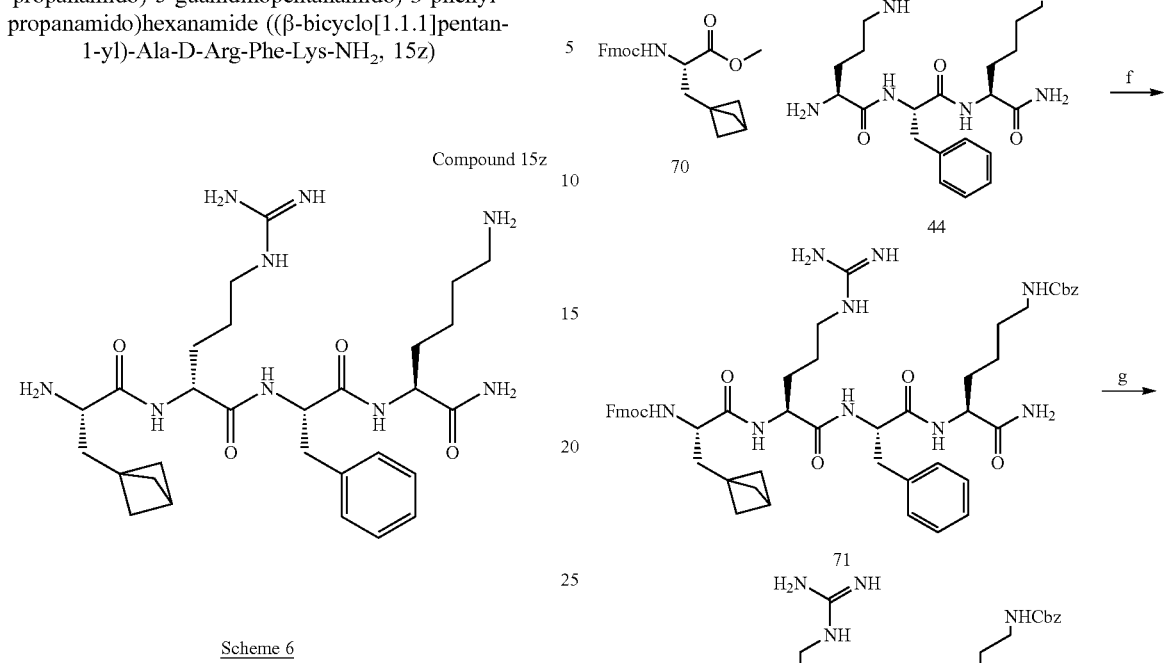

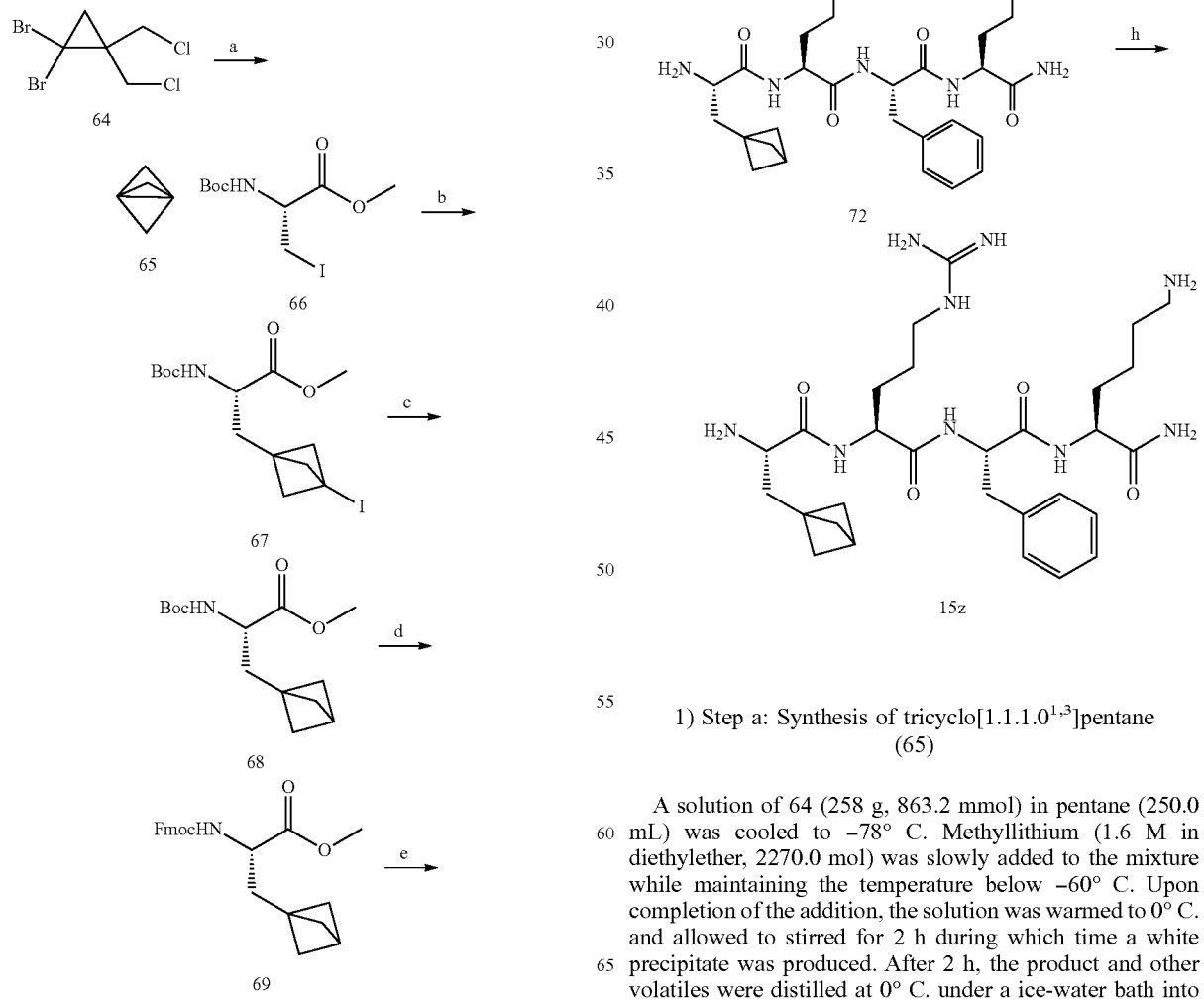

1) Step a: Synthesis of tricyclo[1.1.1.0$^{1,3}$]pentane (65)

A solution of 64 (258 g, 863.2 mmol) in pentane (250.0 mL) was cooled to −78° C. Methyllithium (1.6 M in diethylether, 2270.0 mol) was slowly added to the mixture while maintaining the temperature below −60° C. Upon completion of the addition, the solution was warmed to 0° C. and allowed to stirred for 2 h during which time a white precipitate was produced. After 2 h, the product and other volatiles were distilled at 0° C. under a ice-water bath into a receiving flask cooled to −196° C. with liquid N2. The crude product involving pentane and diethyl ether was used in next step without further purification.

2) Step b: Synthesis of methyl (S)-2-((tert-butoxy-carbonyl)amino)-3-(3-iodobicyclo[1.1.1]pentan-1-yl) propanoate (67)

66 (107.5 g, 326.8 mmol) was dissolved in a solution of 65 from last step. Flushed with argon. This solution was placed around Hg lamp (500 W) and stirred for 10 h at r.t. After completion, the mixture was washed with $NaHSO_3$-solution and test for peroxides, dried over $Na_2SO_4$, filtered off and concentrated in vacuum at 30° C. The residue was washed with PE and filtered. The solid was collected and the residue was purified by chromatographic column to give compound 67 as off-white solid (80 g, 20% for 2 steps). $^1H$ NMR (300 MHz, DMSO-$d_6$) δ 7.29 (br, 1H), 3.95 (m, 1H), 3.60 (s, 3H), 2.19 (m, 6H), 1.87 (m, 2H), 1.38 (s, 9H).

3) Step c: Synthesis of methyl (S)-3-(bicyclo[1.1.1] pentan-1-yl)-2-((tert-butoxycarbonyl)amino)pro-panoate (68)

Compound 67 (70 g, 177.0 mmol) was suspended in water (150 mL) and TTMSS (15 g, 359.0 mmol) was added. The heterogeneous mixture was stirred for 10 min, then 2-mercaptoethanol (1.39 g, 17.8 mmol) followed by AIBN (725 mg, 4.37 mmol) was added. The mixture was stirred 10 min then heated to 80° C. And the reaction mixture became colorless clear solution during heating. The reaction mixture was extracted with EA (150 mL*3), the combined organic layers were washed with brine (150 mL), dried over sodium sulfate, filtered, concentrated and purified by column chromatography ($SiO_2$, 200-300 m, eluted by PE/EtOAc=100/1 to 10/1) to give the desired product 68 (32 g, 58%). $^1H$ NMR (300 MHz, $CDCl_3$) δ 4.94 (br, 1H), 4.31 (m, 1H), 3.74 (s, 3H), 2.46 (s, 1H), 1.97 (m, 1H), 1.80 (m, 1H), 1.74 (m, 6H), 1.46 (s, 9H).

4) Step d: Synthesis of methyl (S)-2-((((9H-fluoren-9-yl)methoxy)carbonyl)amino)-3-(bicyclo[1.1.1] pentan-1-yl)propanoate (69)

Compound 68 (17.0 g, 63.4 mmol) was dissolved in 4N HCl-dioxane (100 mL) and stirred for 1 h, then the mixture was concentrated to dryness. Water (80 mL) and dioxane (80 mL) was added, following by aq. $NaHCO_3$ (5.3 g, 60.1. mmol) and FmocCl (19.6 g, 75.8 mmol). The mixture was then stirred for 3 h at r.t. After completion, solvent was removed under reduced pressure and the residue was purified by column chromatography ($SiO_2$, 200-300 m, eluted by PE/EtOAc=10/1 to 1/1) to give the desired product 69 (15.0 g, 61%). $^1H$ NMR (300 MHz, $CDCl_3$) δ 7.78 (m, 2H), 7.61 (m, 2H), 7.42 (m, 2H), 7.31 (m, 2H), 5.21 (m, 1H), 4.40 (m, 3H), 4.27 (m, 1H), 3.76 (s, 3H), 2.47 (s, 1H), 2.04 (m, 1H), 1.85 (m, 1H), 1.73 (s, 6H).

5) Step e: Synthesis of (S)-2-((((9H-fluoren-9-yl) methoxy)carbonyl)amino)-3-(bicyclo[1.1.1]pentan-1-yl)propanoic acid (70)

Compound 69 (15.0 g) was dissolved in ION aq. HCl (100 mL) and dioxane (100 mL), then the reaction was warmed to 50° C. and stirred for 24 h. After completion, solvent was removed and the residue was purified by column chromatography ($SiO_2$, 200-300 m, eluted by PE/EtOAc=10/1 to DCM/MeOH=50/1, 0.1% AcOH) to give the crude product 70 (11.0 g), further purification by beating with PE/EtOAc (150 mL, v/v=50/1) to give the purity product (70, 9.5 g, 66%) as an off-white solid. $^1H$ NMR (300 MHz, DMSO-$d_6$) δ 7.89 (m, 2H), 7.72 (m, 1H), 7.54 (m, 1H), 7.41 (m, 2H), 7.32 (m, 2H), 4.36 (m, 1H), 4.24 (m, 2H), 3.93 (m, 1H), 2.40 (s, 1H), 1.78 (m, 2H), 1.62 (m, 6H).

6) Step f: Synthesis of (9H-fluoren-9-yl)methyl ((9S,12S,15S,18S)-12-benzyl-19-(bicyclo[1.1.1] pentan-1-yl)-9-carbamoyl-15-(3-guanidinopropyl)-3, 11,14,17-tetraoxo-1-phenyl-2-oxa-4,10,13,16-tetraa-zanonadecan-18-yl)carbamate (71)

To a mixture of 70 (226 mg, 0.6 mmol), 44 (330 mg, 0.5 mmol), HOBt monohydrate (138 mg, 0.9 mmol), EDC hydrochloride (288 mg, 1.5 mmol) in DMF (20 mL) NMM (222 mL, 2 mmol) was added dropwise at RT. Reaction mixture was stirred overnight, then solvents were removed under reduced pressure and crude product was purified by flash reverse phase chromatography (eluent $H_2O$ (0.2% AcOH)/MeOH from 10% to 85% of methanol). As a result 190 mg of 71 was isolated as acetate salt. $^1H$ NMR (400 MHz, Methanol-$d_4$) δ 7.78 (d, J=7.6 Hz, 2H), 7.63 (m, 2H), 7.38 (m, 2H), 7.31-7.17 (m, 2H) 7.65-7.61 (m, 2H), 7.39-7.36 (m, 2H), 7.30-7.18 (7H, m), 4.58-4.48 (m, 2H), 4.36-4.32 (m, 1H), 4.28-4.24 (m, 1H), 4.22-4.17 (m, 2H), 4.05-4.01 (m, 1H), 3.25-3.20 (m, 1H), 3.5-2.97 (m, 4H), 2.91-2.85 (m, 1H), 2.03 (s, 9H), 1.90-1.86 (m, 2H), 1.76-1.65 (m, 10H).

7) Step g: Synthesis of benzyl ((S)-6-amino-5-((S)-2-((S)-2-((S)-2-amino-3-(bicyclo[1.1.1]pentan-1-yl) propanamido)-5-guanidinopentanamido)-3-phenyl-propanamido)-6-oxohexyl)carbamate (72)

71 (190 mg) was treated with a mixture of 20% Piperidine/DMF (3 mL). The reaction mixture was stirred 1 h at rt, then organic solvent was evaporated and crude product was purified by flash reverse phase chromatography (eluent $H_2O$ (0.2% AcOH)/MeOH from 5% to 70% of methanol). As a result, 110 mg of 72 was isolated as diacetate salt. $^1H$ NMR (400 MHz, Methanol-$d_4$) δ 7.32-7.20 (m, 5H), 4.66-4.62 (m, 1H), 4.36-4.32 (m, 1H), 4.13-4.10 (m, 1H), 3.49-3.45 (m, 1H), 3.40-3.32 (m, 1H), 3.07-2.97 (m, 4H), 2.88-2.81 (m, 1H), 1.93 (s, 9H), 1.89-1.77 (m, 2H), 1.72-1.68 (m, 1H), 1.61-1.50 (m, 3H), 1.35-1.26 (m, 1H), 1.13-1.04 (m, 1H).

8) Step h: Synthesis of (S)-6-amino-2-((S)-2-((S)-2-((S)-2-amino-3-(bicyclo[1.1.1]pentan-1-yl)propana-mido)-5-guanidinopentanamido)-3-phenylpropana-mido)hexanamide (15z)

To a solution of 72 (110 mg), in DCM (6 mL) was added TFA (2 mL) at 0° C. After 5 min ice bath was removed and the reaction mixture was stirred 3 h at ambient temperature. The volatiles were evaporated and crude product was purified by preparative HPLC to give a pure 15z. $^1H$ NMR (400 MHz, Methanol-$d_4$) δ 7.38-7.15 (m, 5H), 4.66 (dd, J=11.3, 4.2 Hz, 1H), 4.45 (dd, J=8.7, 5.7 Hz, 1H), 4.14 (t, J=7.4 Hz, 1H), 3.85 (t, J=6.7 Hz, 1H), 3.40 (dd, J=14.1, 4.2 Hz, 1H), 3.07-2.89 (m, 4H), 2.84 (dd, J=14.2, 11.4 Hz, 1H), 2.47 (s, 1H), 2.13-1.63 (m, 12H), 1.62-1.39 (m, 4H), 1.36-1.20 (m, 1H), 1.02 (m, 1H). MS: EI-MS: m/z 586.4 [M+1].

Example 27. Synthesis of (S)-6-amino-2-((S)-2-((R)-2-((S)-2-amino-3-phenylpropanamido)-5-guanidinopentanamido)-3-(bicyclo[1.1.1]pentan-1-yl)propanamido)hexanamide (Phe-D-Arg-(β-bicyclo[1.1.1]pentan-1-yl)-Ala-Lys-NH₂, 15aa)

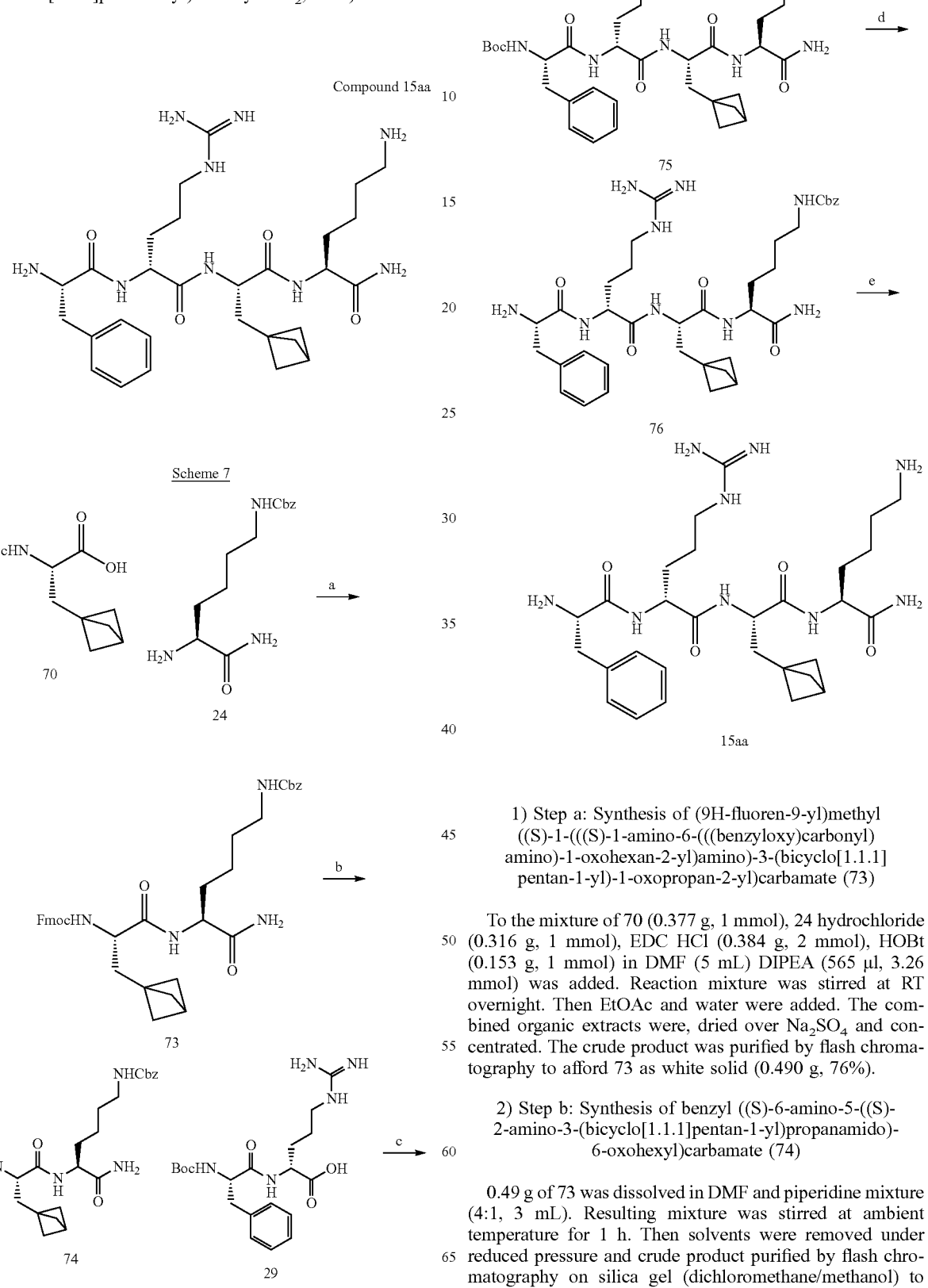

1) Step a: Synthesis of (9H-fluoren-9-yl)methyl ((S)-1-(((S)-1-amino-6-(((benzyloxy)carbonyl)amino)-1-oxohexan-2-yl)amino)-3-(bicyclo[1.1.1]pentan-1-yl)-1-oxopropan-2-yl)carbamate (73)

To the mixture of 70 (0.377 g, 1 mmol), 24 hydrochloride (0.316 g, 1 mmol), EDC HCl (0.384 g, 2 mmol), HOBt (0.153 g, 1 mmol) in DMF (5 mL) DIPEA (565 μl, 3.26 mmol) was added. Reaction mixture was stirred at RT overnight. Then EtOAc and water were added. The combined organic extracts were, dried over Na₂SO₄ and concentrated. The crude product was purified by flash chromatography to afford 73 as white solid (0.490 g, 76%).

2) Step b: Synthesis of benzyl ((S)-6-amino-5-((S)-2-amino-3-(bicyclo[1.1.1]pentan-1-yl)propanamido)-6-oxohexyl)carbamate (74)

0.49 g of 73 was dissolved in DMF and piperidine mixture (4:1, 3 mL). Resulting mixture was stirred at ambient temperature for 1 h. Then solvents were removed under reduced pressure and crude product purified by flash chromatography on silica gel (dichloromethane/methanol) to yield 0.21 g of 74 as a free base.

3) Step c: Synthesis of tert-butyl ((9S,12S,15R, 18S)-12-(bicyclo[1.1.1]pentan-1-ylmethyl)-9-carbamoyl-15-(3-guanidinopropyl)-3,11,14,17-tetraoxo-1,19-diphenyl-2-oxa-4,10,13,16-tetraazanonadecan-18-yl)carbamate (75)

To a mixture of 74 (0.2 g, 0.48 mmol), Boc-Phe-(D-)Arg-OH hydrochloride (29, 0.229 g, 0.5 mmol), HOBt monohydrate (77 mg, 0.5 mmol), EDC hydrochloride (0.192 g, 1 mmol) in DMF (5 mL) NMM (0.12 mL, 1.06 mmol) was added at 0° C. After 5 min ice bath was removed and the reaction mixture was stirred 1 day at RT, then evaporated and purified by flash column chromatography (eluent $H_2O$ (0.10% AcOH)/MeOH). 0.11 g of crude product 75 was isolated and used in the next step.

4) Step d: Synthesis of benzyl ((S)-6-amino-5-((S)-2-((R)-2-((S)-2-amino-3-phenylpropanamido)-5-guanidinopentanamido)-3-(bicyclo[1.1.1]pentan-1-yl)propanamido)-6-oxohexyl)carbamate (76)

To a solution of crude product (75, 110 mg) in DCM (3 mL) TFA (1.5 mL) was added at 0° C. After 5 min ice bath was removed and the reaction mixture was stirred 30 min at ambient temperature. The volatiles were evaporated, and then crude product was purified by preparative HPLC. 59 mg of 76 was isolated.

5) Step e: Synthesis of (S)-6-amino-2-((S)-2-((R)-2-((S)-2-amino-3-phenylpropanamido)-5-guanidinopentanamido)-3-(bicyclo[1.1.1]pentan-1-yl)propanamido)hexanamide (15aa)

To a solution of 59 mg of 76 in MeOH (20 mL) 16 mg of Pd/C 10% w/w was added. The flask was flushed out with $H_2$ and the mixture was stirred for 2 h at RT. Then precipitates were filtered off and 0.2 mL of TFA was added. Mixture was evaporated and re-evaporated with methanol three times yielding 33 mg of 15aa as foam. $^1$H NMR (400 MHz, Methanol-$d_4$) δ 8.62 (br d, J=7.6 Hz, 1H), 7.85 (br d, J=8.4 Hz, 1H), 7.43-7.31 (m, 5H), 4.43-4.40 (m, 1H), 4.29-4.17 (multiple peaks, 2H), 3.20-3.13 (m, 4H), 2.95-2.75 (m, 2H), 2.48 (m, 1H), 2.09 (dd, J=3.2, 14.8 Hz, 1H), 1.94-1.18 (multiple peaks, 18H). MS: EI-MS: m/z 586.5 [M+1].

Example 28: Synthesis of (S)-6-amino-2-((S)-2-((R)-2-((S)-2-amino-3-phenylpropanamido)-5-guanidinopentanamido)-3-(tetrahydro-2H-pyran-4-yl)propanamido)hexanamide (Phe-D-Arg-(β-tetrahydro-2H-pyran-4-yl)-Ala-Lys-NH$_2$, 15ab)

Compound 15ab

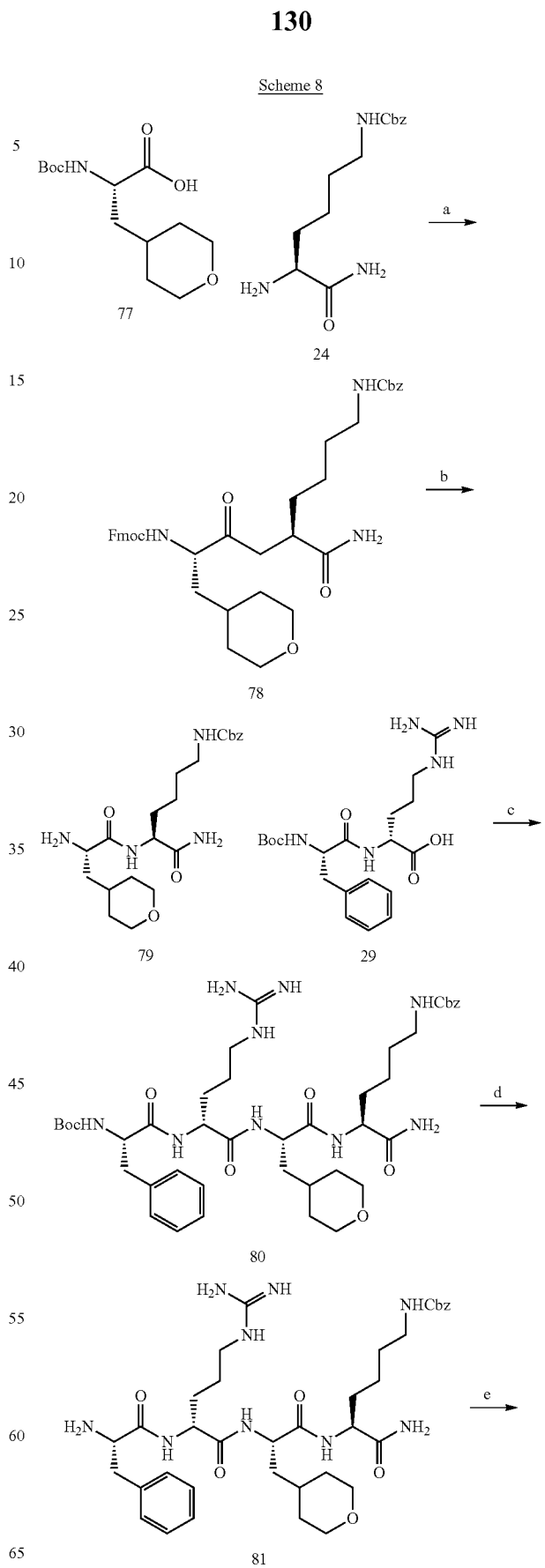

Scheme 8

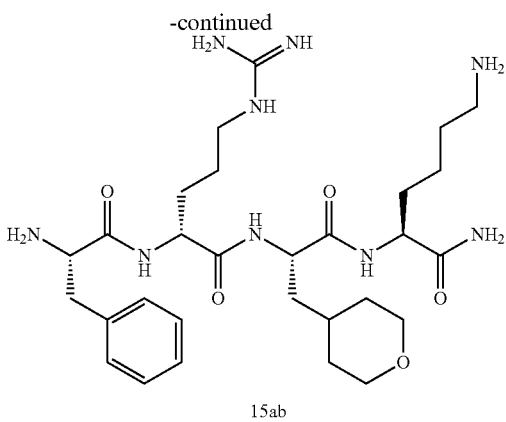

15ab

1) Step a: Synthesis of (9H-fluoren-9-yl)methyl ((S)-1-(((S)-1-amino-6-(((benzyloxy)carbonyl)amino)-1-oxohexan-2-yl)amino)-1-oxo-3-(tetrahydro-2H-pyran-4-yl)propan-2-yl)carbamate (79)

To the mixture of amino-3-(tetrahydro-2H-pyran-4-yl)propanoic acid (78, 205 mg, 0.716 mmol) and 24 (300 mg, 0.788 mmol) in DMF (7 mL) DIPE (565 µl, 3.26 mmol) were added. Reaction mixture was stirred at RT overnight. Then EtOAc and water were added. The combined organic extracts were, dried over $Na_2SO_4$ and concentrated. The crude product was purified by flash chromatography (2% EtOH in DCM) to afford 79 as white solid (380 mg, 98%). $^1$H NMR (400 MHz, Methanol-$d_4$) δ 7.35-7.27 (m, 5H), 5.06 (s, 2H), 4.31 (dd, J=9.0, 4.8 Hz, 1H), 4.09 (dd, J=9.0, 4.2 Hz, 1H), 3.89 (pent, J=5.2 Hz, 2H), 3.36 (q, J=12.1 Hz, 2H), 3.11 (t, J=6.7 Hz, 2H), 1.87-1.74 (m, 1H), 1.72-1.45 (m, 8H), 1.44 (s, 9H), 1.43-1.18 (m, 4H).

2) Step b: Synthesis of benzyl ((S)-6-amino-5-((S)-2-amino-3-(tetrahydro-2H-pyran-4-yl)propanamido)-6-oxohexyl)carbamate (80)

To a cooled (0° C.) solution of 79 (380 mg, 0.711 mmol) in DCM (7 mL) TFA (2.0 mL) was added. After 5 min, the ice bath was removed and the mixture stirred at ambient temperature for 2 h. Volatiles was removed under reduced pressure. It was obtained 395 mg (yield—90%) of 80. Yellowish solid was used without further purification. $^1$H NMR (400 MHz, Methanol-$d_4$) δ 7.36-7.28 (m, 5H), 5.06 (s, 2H), 4.39 (dd, J=8.7, 5.4 Hz, 1H), 3.96-3.90 (m, 3H), 3.47-3.40 (m, 2H), 3.12 (t, J=6.8 Hz, 2H), 1.87-1.79 (m, 2H), 1.78-1.62 (m, 5H), 1.56-1.29 (m, 6H).

3) Step c: Synthesis of tert-butyl ((9S,12S,15R,18S)-9-carbamoyl-15-(3-guanidinopropyl)-3,11,14,17-tetraoxo-1,19-diphenyl-12-((tetrahydro-2H-pyran-4-yl)methyl)-2-oxa-4,10,13,16-tetraazanonadecan-18-yl)carbamate (81)

To mixture of 80 (390 mg, 0.711 mmol) and 30 (340 mg, 0.743 mmol) in DMF (15 mL) were added HOBT*$H_2O$ (130 mg, 0.853 mmol), EDC*HCl (409 mg, 2.13 mmol) and NMM (3900 µl, 3.55 mmol). Reaction mixture was stirred at room temperature. After 48 h DMF was removed. Crude product was purified by reverse phase flash chromatography (20-65% MeOH in $H_2O$) to afford 81 as white solid (274 mg, purity–85%). Additional purification was performed by HPLC. 81 was isolated as a white solid (178 mg). $^1$H NMR (400 MHz, Methanol-$d_4$) δ 7.40-7.26 (m, 10H), 5.06 (s, 2H), 4.54 (dd, J=9.6, 6.0 Hz, 1H), 4.40-4.26 (m, 3H), 3.95-3.84 (m, 3H), 3.45-3.32 (m, 2H), 3.21-3.00 (m, 3H), 3.11 (t, J=6.8 Hz, 2H), 1.86-1.58 (m, 12H), 1.56-1.20 (m, 5H), 1.38 (s, 9H).

4) Step d: Synthesis of benzyl ((S)-6-amino-5-((S)-2-((R)-2-((S)-2-amino-3-phenylpropanamido)-5-guanidinopentanamido)-3-(tetrahydro-2H-pyran-4-yl)propanamido)-6-oxohexyl)carbamate (82)

To a cooled (0° C.) solution of 81 (175 mg) in DCM (5 mL) TFA (0.5 mL) was added. Volatiles were removed under reduced pressure. It was obtained 200 mg of LIOS-076-6. Yellowish oil 82 was used without further purification. $^1$H NMR (400 MHz, Methanol-$d_4$) δ 7.40-7.26 (m, 10H), 5.06 (s, 2H), 4.54 (dd, J=9.3, 5.9 Hz, 1H), 4.38 (dd, J=8.8, 5.3 Hz, 1H), 4.31 (dd, J=9.0, 5.1 Hz, 1H), 4.23-4.12 (m, 1H), 3.95-3.86 (m, 3H), 3.34-3.32 (m, 2H), 3.23-3.06 (m, 3H), 3.11 (t, J=6.9 Hz, 2H), 1.88-1.23 (m, 17H).

5) Step e: Synthesis of (S)-6-amino-2-((S)-2-((R)-2-((S)-2-amino-3-phenylpropanamido)-5-guanidinopentanamido)-3-(tetrahydro-2H-pyran-4-yl)propanamido)hexanamide (15ab)

A solution of 82 (200 mg, 0.235 mmol) in MeOH (10 mL) Pd/C (10% w/w, 15 mg) was purged with hydrogen at room temperature for 3 h. Then reaction mixture was filtrated through Celite pad and washed with MeOH (10 mL). The solvent was removed by evaporation. It was obtained 119 mg white solid. Purification was performed by HPLC. 15ab was isolated as white solid (9 mg, impurities <5%). $^1$H NMR (400 MHz, Methanol-$d_4$) δ 7.39-7.26 (m, 5H), 4.42-4.32 (m, 2H), 4.39 (t, J=7.4 Hz, 1H), 4.14 (t J=7.8 Hz, 1H), 3.94-3.89 (m, 2H), 3.42-3.32 (m, 2H), 3.20-3.08 (m, 4H), 2.94-2.91 (m, 2H), 3.11 (t, J=6.9 Hz, 2H), 1.87-1.25 (m, 17H). MS: EI-MS: m/z 604.5 [M+1].

Example 29: Synthesis of (2S)-2-((2R)-3-(adamantan-1-yl)-2-((R)-2-((S)-2-amino-3-phenylpropanamido)-5-guanidinopentanamido)propanamido)-6-aminohexanamide (Phe-D-Arg-D-(β-admant-1-yl)-Ala-Lys-NH₂, 15ac)

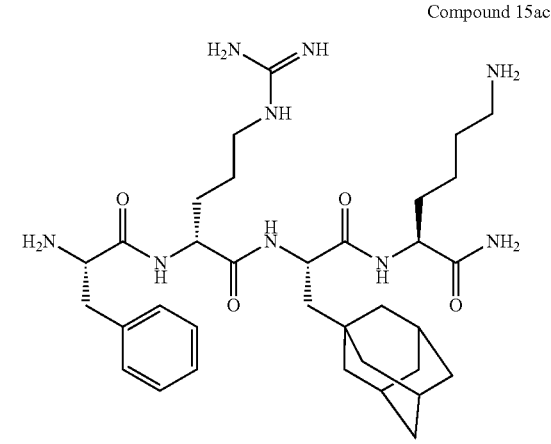 [SMILES: N=C(N)NCCC[C@@H](NC(=O)[C@@H](N)Cc1ccccc1)C(=O)N[C@@H](CC12CC3CC(CC(C3)C1)C2)C(=O)N[C@@H](CCCCN)C(N)=O]

Compound 15ac

Compound 15ac (63 mg) was isolated according to Schedule 2 as white powder. $^1$H NMR (400 MHz, Methanol-d$_4$) δ 7.42-7.26 (m, 5H), 4.45 (ddd, J=7.5, 5.1, 2.7 Hz, 2H), 4.36 (dd, J=8.7, 5.2 Hz, 1H), 4.26 (dd, J=8.8, 5.1 Hz, 1H), 3.37-3.33 (m, 1H), 3.25 (t, J=6.9 Hz, 2H), 3.00 (dd, J=14.3, 8.9 Hz, 1H), 2.94 (t, J=7.5 Hz, 2H), 2.02-1.39 (multiple peaks, 27H). MS: EI-MS: m/z 654.6 [M+1].

Example 30: Rat Permeabilized Cardiac Fiber A/R Study

Mitochondrial Functionality In Vitro Anoxia-Reoxygenation (A/R) Model
1) The Preparation of Permeabilized Cardiac Fibers The permeabilized cardiac fibers are prepared from normoxic heart as described previously (Kuka J, Vilskersts R, Cirule H, Makrecka M, Pugovics O, Kalvinsh I, Dambrova M, Liepinsh E. The cardioprotective effect of mildronate is diminished after co-treatment with L-carnitine. J Cardiovasc Pharmacol Ther. 2012 June; 17(2):215-22. doi: 10.1177/1074248411419502) with some modifications. The bundles of fibers are permeabilized using 50 μg/mL saponin and 0.5 mg/mL collagenase at 4° C. in 1 mL of buffer A (20 mM imidazole, 0.5 mM dithiothreitol, 20 mM taurine, 7.1 mM MgCl$_2$, 50 mM MES, 5 mM ATP, 15 mM phosphocreatine, 2.6 mM CaK$_2$EGTA, 7.4 mM K$_2$EGTA, pH 7.0 at 0° C.). After 15 min incubation, the fibers are washed for 15 min in 2 mL of buffer B (20 mM imidazole, 0.5 mM dithiothreitol, 20 mM taurine, 1.6 mM MgCl$_2$, 100 mM MES, 3 mM KH$_2$PO$_4$, 2.9 mM CaK$_2$EGTA, 7 mM K$_2$EGTA, pH 7.1 at 37° C.) supplemented with compound (e.g. 100 nM) or vehicle.
2) Respiration Measurements with Simultaneous H$_2$O$_2$ Flux Detection Medium for respiration measurements: MiR05—110 mM sucrose, 60 mM K-lactobionate, 0.5 mM EGTA, 3 mM MgCl$_2$, 20 mM taurine, 10 mM KH$_2$PO$_4$, 20 mM HEPES, pH 7.1 at 30° C., and 0.1% BSA essentially fatty acid free.
Protocol To induce anoxia maximal respiration rate of sample is stimulated by the addition of substrates, succinate (10 mM) with rotenone (0.5 μM) and ADP (5 mM), and preparation is left to consume all 02 in respiratory chamber (within 10-20 min), thereby entering into an anoxic state (Makrecka M, Svalbe B, Volska K, Sevostjanovs E, Liepins J, Grinberga S, Pugovics O, Liepinsh E, Dambrova M. Mildronate, the inhibitor of L-carnitine transport, induces brain mitochondrial uncoupling and protects against anoxia-reoxygenation. Eur J Pharmacol. 2014 Jan. 15; 723:55-61. doi: 10.1016/j.ejphar.2013.12.006.). After 30 min anoxia, O$_2$ is reintroduced to the chamber by opening the chamber to achieve reoxygenation. After O$_2$ concentration in chamber reaches initial concentration, the chamber is closed and O$_2$ flux is monitored for 10 min.

H$_2$O$_2$ flux (ROSflux) is measured simultaneously with respirometry in the O2k-Fluorometer using the H$_2$O$_2$-sensitive probe Ampliflu™ Red (AmR) (Makrecka-Kuka M, Krumschnabel G, Gnaiger E. High-Resolution Respirometry for Simultaneous Measurement of Oxygen and Hydrogen Peroxide Fluxes in Permeabilized Cells, Tissue Homogenate and Isolated Mitochondria. Biomolecules. 2015 Jun. 29; 5(3):1319-38. doi: 10.3390/biom5031319). 10 μM AmR, 1 U/mL horse radish peroxidase (HRP) and 5 U/mL superoxide dismutase (SOD) are added to the chamber. The reaction product between AmR and H$_2$O$_2$, catalyzed by HRP, is fluorescent, similar to resorufin. Calibrations are performed with H$_2$O$_2$ repeatedly added at 0.1 μM steps. Additional AmR can be added to ensure H$_2$O$_2$ flux measurements after reoxygenation.

The tested compound or vehicle is added at baseline (before addition of permeabilized fibers).
Study outline:
Permeabilized cardiac fibers CII OXPHOS state+30 min. anoxia+10 min. reoxygenation, in the presence of the H$_2$O$_2$-sensitive probe Ampliflu™ Red
Parameters: CII OXPHOS (normoxia, after reoxygenation), H$_2$O$_2$ (ROS) flux (normoxia, after reoxygenation), H$_2$O$_2$/O$_2$ ratio (normoxia, after reoxygenation)
CTRL (vehicle)+3-4 SBT compounds at 100 nM concentrations (n=5-6) are tested in parallel per set. The number of compounds tested in parallel as well as compound concentration(s) may be adjusted and will be recorder in the study file and in the final report.
The protocol may be modified based on the experimental results and discussions with the Sponsor. Any changes to the protocol will be documented in the study file and in the protocol amendment.
See FIG. 2.

Example 31: Langendorff Study

Ischemia-reperfusion injury-Langendorff heart preparation Protocol (Latvian Institute of Organic Synthesis)
The infarction study is performed according to the Langendorff technique as described previously (Kuka J, Vilskersts R, Cirule H, Makrecka M, Pugovics O, Kalvinsh I, et al. The cardioprotective effect of mildronate is diminished after co-treatment with L-carnitine. J Cardiovasc Pharmacol Ther. 2012; 17:215-222), with some modifications. Rats are anaesthetized with sodium pentobarbital (60 mg/kg) and heparin is administered intraperitoneally. For the infarction studies, the hearts are perfused with oxygenated (95% O2-5% CO$_2$) Krebs-Henseleit (KH) buffer solution (118 mmol/L NaCl, 4.7 mmol/L KCl, 1.24 mmol/L CaCl2), 1.64 mmol/L MgCl2, 24.88 mmol/L NaHCO$_3$, 1.18 mmol/L KH$_2$PO$_4$, and 0.05 mmol/L EDTA; pH 7.3-7.5; 36.8-37.0° C.) supplemented with 10 mM glucose at a constant perfusion pressure of 60 mmHg. A water-ethanol mixture (1:1)-filled balloon connected to a physiological pressure transducer (ADInstruments) is inserted into the left ventricle, and the baseline end-diastolic pressure set at 5-10 mmHg. The heart rate (HR), flow, left-ventricle developed pressure (LVDP), contractility (+dp/dt) are continuously recorded using a PowerLab 8/35 system from ADInstruments. The isolated rat hearts are adapted for 20 min and the left anterior descending coronary artery (LAD) is subsequently occluded for 30 min followed by 120 min of reperfusion. KH perfusion solution with or without added compound of interest (vehicle or 1 μM concentration) will be used for the whole time of isolated heart perfusion. Occlusion is confirmed by ~40% drop in coronary flow. The infarct size is determined as described previously (Kuka J, Vilskersts R, Cirule H, Makrecka M, Pugovics O, Kalvinsh I, Dambrova M, Liepinsh E. The cardioprotective effect of mildronate is diminished after co-treatment with L-carnitine. J Cardiovasc Pharmacol Ther. 2012 June; 17(2):215-22. doi: 10.1177/1074248411419502.; Liepinsh E, Kuka J, Dambrova M. Troubleshooting digital macro photography for image acquisition and the analysis of biological samples. J Pharmacol Toxicol Methods. 2013 March-April; 67(2):98-106. doi: 10.1016/j.vascn.2012.11.001.). Briefly, at the end of the reperfusion, the LAD is re-occluded, and the heart is perfused with 0.1% methylene blue dissolved in KH buffer solution. Afterwards, hearts are sectioned transversely from the apex to the base in 6 slices (5 if smaller heart) of 2 mm thickness and incubated in 1% triphenyl-tetrazolium chloride in phosphate buffer (pH 7.4, 37° C.) for 10 min to stain viable tissue red and necrotic tissue white. The planimetric analysis of cross-sectional images is performed using Image-Pro Plus v6.3 software to determine the area at risk (AR) and area of necrosis (AN), each expressed as a percentage of cross-sectional slice area. The obtained values are then used to calculate the infarct size (IS) as a percentage of the risk area according to the formula:

$$IS(\%)=AN/AR\times100\%.$$

Area of necrosis is determined by combining areas of the white necrotic and pink tissue.

Study outline 20 min. adaptation+30 min. ischemia (LAD ligation)+120 min. reperfusion. Vehicle or compound 1 µM The test article concentration(s) may be adjusted. Any changes will be recorded in the study file and the final report.

Endpoints: HR, flow, LVDP, ±dP/dt, infarct size-area of necrosis

CTRL (vehicle)+up to 4 test compounds (n=8 per treatment) tested per set

The protocol and the number of compounds to be tested may be modified based on the experimental results and discussions with the Sponsor. Any changes to the protocol will be documented in the study file and in the protocol amendment.

Figure 3:
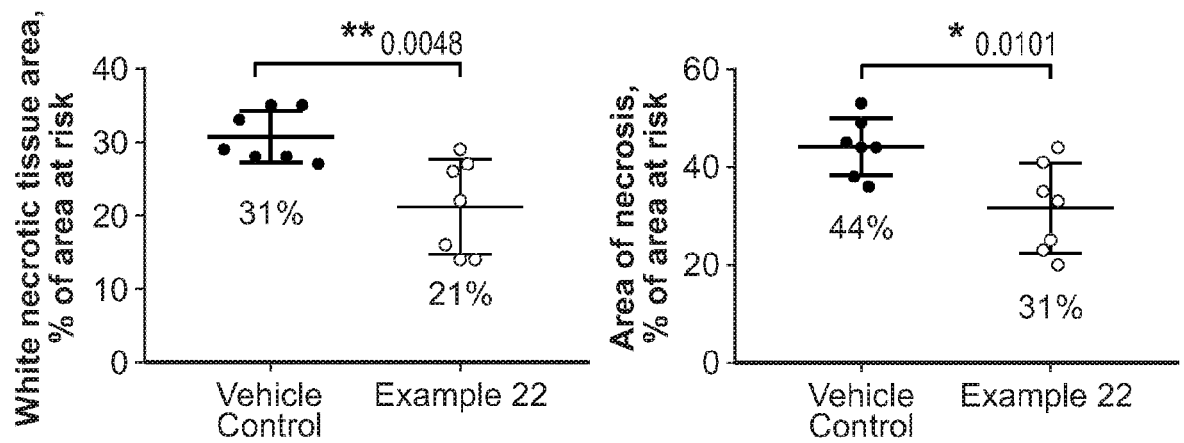
FIG. 3 depicts white necrotic tissue area as % of Area at Risk (only area of the white necrotic tissue is used in the analysis) and Infarct Size (%), mean±SD. See Example 31.

See FIG. 3.

Example 32: Rat Myocardial Infarction Model

The Rat Myocardial Infarction Model (MI) was performed by IPST Therapeutique Inc, Sherbrooke, Quebec, Canada. The animals were randomized in terms of even distribution between treatment groups based on their body weight by the Study Director with the aim of scheduling animal from each treatment group for each day of surgery (when possible).

1) Vehicle group: size of the group: n=8. Route of administration: s.c.;
2) Test article group: size of the group: n=8. Route of administration: s.c.; Treatment: 0.01, 0.1, 0.5 and 2 mg/kg doses, 30 min before ischemia.

EXPERIMENTAL PROCEDURES

Study Design

1) On the day of the surgery, the rat will be anaesthetized with a mixture of 2 to 2.5%. isoflurane USP (Abbot Laboratories, Montreal Canada) in oxygen, and placed on a heating pad to maintain body temperature.
2) The animal will be intubated and immediately ventilated by means of a positive-pressure rodent respirator set at ~ 10 mL/kg bodyweight at a frequency of 65-70 strokes/min.
3) A thoracotomy will be performed through the left forth intercostal space to exposed the heart.
4) A 5-0 sofsilk suture will be placed around the left anterior descending (LAD) artery, 2-3 mm below the left atrium.
5) The suture will be briefly snared to verify the size and location of myocardial ischemia based on color change and will then be tied to produce a large anterolateral myocardial infarction (around 45%).
6) 30 minutes following LAD occlusion, the suture will be removed to allow a reperfusion of the muscle.
7) The thoracotomy will be closed with a 4-0 suture and a meloxicam (1 mg/kg) subcutaneous injection will be done for postoperative pain management.
8) 24 hours post-reperfusion, the animal will be re-anesthetized (isoflurane 2%).
9) The heart will be excised and mounted into a Langendorff apparatus. Oxygenated Tyrode's solution heated at 35±2° C. will perfuse the heart in a retrograde manner at a pressure of approximately 70 mmHg and a flow rate on the order of 10 mL/min.
10) The heart will then be perfused with Evans blue dye to evaluate the size of the myocardial infarction. Following Evans blue staining, the heart will be removed from the Langendorff apparatus and immersed in cold ethanol (−50° C.). The heart will be cut in transversal slices sections of approximately 2 mm. The slices will be scanned to evaluate the area at risk (AAR) before to be incubated in phosphate buffer containing 1% TTC for 30 minutes at 35±2° C. and then transfer in formalin 4% for 24 hours at 4±2° C. The slices will be re-scanned to measure the infracted area. Animals with an area at risk >60% will be excluded from the study.

Calculations

Infarct Size(%)=(Infarcted Area/Area at Risk)*100

Computer Systems

A networked personal computer running either Microsoft Windows8, XP Professional or Microsoft Windows Vista Business will be used for data acquisition. The analysis software will be Microsoft Office Excel 2007 installed on networked personal computers running Microsoft Windows8, XP Professional or vista.

Reporting

Progress/Status Reports

Regular progress reports will be submitted to the Sponsor's contact person throughout the study. The frequency of these reports will be determined after consultation with the Sponsor's contact person.

Study Report

Within one week after completion of the experimental phase of the study, non-audited raw data in Excel spreadsheets and a draft non-audited report containing the study design, the study's quantitative/qualitative results, and individual data graphs will be submitted to the Sponsor. The final report will be provided within 1 week of receiving Sponsors comments.

Figure 4:
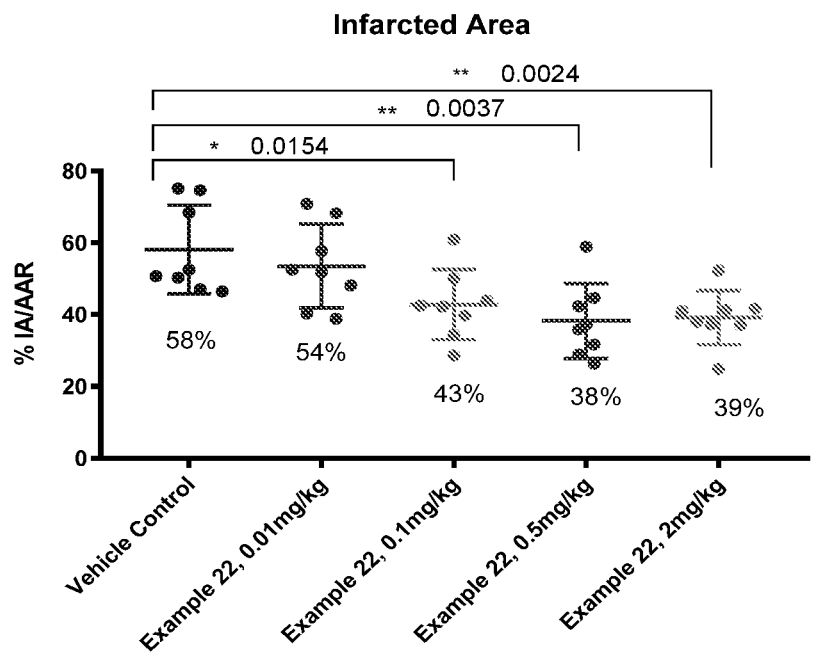
FIG. 4 depicts dose response in rat Myocardial Infarction (MI) model, mean±SD. See Example 32.

See FIG. 4.

Example 33: Renal Ischemic Study

The Rat Acute Kidney Injury (AKI) Model was performed by IPST Therapeutique Inc, Sherbrooke, Quebec, Canada. The animals were randomized in terms of even distribution between treatment groups based on their body weight by the Study Director with the aim of scheduling animal from each group at each day of surgery. The rats will be given free access to food and water.

1) Sham group: size of the group: n=2. Route of administration: n/a;
2) Vehicle group: size of the group: n=8. Route of administration: s.c.;
3) Test article group: size of the group: n=8. Route of administration: s.c.; Treatment dose: 2×2 mg/kg, 30 min before ischemia and 5 min before reperfusion.

EXPERIMENTAL PROCEDURES

Induction of Ischemia-Reperfusion

1. Rats will be anaesthetized with isoflurane USP (Abbot Laboratories, Montreal Canada) 2% in oxygen and placed on a heated pad to maintain body temperature. The ECG and oxygen saturation will be monitored for the entire surgical process. The body temperature will be monitored with a probe thermometer introduced into the abdomen, very close to the kidneys.

2. A 1 mL blood draw will be taken from the jugular vein. The blood will be collected into lithium heparin tubes and centrifuged at 3000 rpm for 10 min. to obtain the plasma. The plasma will be separated into 200 µL aliquot and stored at −20° C. until dosage of biomarkers.

3. The abdomen will be disinfected with providone iodine and alaparotomy will be performed.

4. The kidneys will be exposed and a temporary suture will be placed around renal artery of the two kidneys. Renal ischemia will be visually confirmed by a gradual changed of the kidneys colour going from red to dark purple within a couple of minutes following the start of the ischemia. During the ischemia, the kidneys will be kept moist and warm using a heat lamp and sterile gauze soaked in warm (37° C.) saline. The temperature will be monitored with a probe thermometer introduced into the abdomen, very close to the kidneys.

5. After 30 minutes of occlusion, the suture will be removed.

6. The abdominal wounds will be closed with 4-0 silk suture, and the animal will be return to its cage.

7. Twenty four (24) hours after the reperfusion the rats will be re-anesthetized. A second blood draw will be taken as was done before the ischemia.

8. Sham will be treated under same conditions as vehicle, except, kidneys will not be subjected to ischemic conditions.

Detection of Biomarkers

A 200 µL aliquot of plasma sample will be taken before the ischemia and 24 hours following the ischemia will be sent to the clinical laboratory of the CHUS (Centre Hospitalier Universitaire de Sherbrooke, Quebec, Canada) for detection of plasma level of creatinine (p.Cr) and Blood Urea Nitrogen (BUN).

Computer Systems

The following are the validated computer systems to be used during the conduct of this study. The analysis software will be Microsoft Office Excel 2007 installed on networked personal computers running Microsoft Windows 8, XP Professional or Vista.

Data Analysis

Values are presented as means±SEM (standard error of the means). Repeat un-paired Student's t-tests were performed in Microsoft Excel 2007 on all experimental data.

Differences were considered significant when p 0.05.

The vehicle group was compared to the sham group while the test article was compared to the vehicle group.

The plasma creatinine post-I/R (% mean of vehicle) was calculated using the following formula:

$$\frac{((\text{Plasma creatinine 24h post-}isch.) - (\text{Plasma creatinine pre-}isch.)) - \text{Mean } \Delta \text{ Plasma creatinine in sham group}}{(\text{Mean } \Delta \text{ Plasma creatinine in vehicle group})} \times 100$$

Where:

Mean Δ plasma creatinine in sham group=Mean (plasma creatinine 24 h post-isch.—plasma creatinine pre-isch.) in sham group Mean Δ plasma creatinine in vehicle group=Mean ((plasma creatinine 24 h post-isch.-plasma creatinine pre-isch.)—Mean Δ plasma creatinine in sham group) in vehicle group The BUN post-I/R (% mean of vehicle) was calculated using the following formula:

$$\frac{((\text{BUN 24h post-}isch.) - (\text{BUN pre-}isch.)) - \text{Mean } \Delta \text{ BUN in sham group}}{\text{Mean } \Delta \text{ BUN in vehicle group}} \times 100$$

Where.

Mean Δ BUN in sham group=Mean (BUN 24 h post-isch.—BUN pre-isch.) in sham group

Mean Δ BUN in vehicle group=Mean ((BUN 24 h post-isch.—BUN pre-isch.)—Mean Δ BUN in sham group) in vehicle group % Protection was calculated using the following formulas:

$$\% \text{ Protection(plasma creatinine)}=100\%-\Delta \text{ Plasma Creatinine post-I/R(\% mean of vehicle)}$$

$$\% \text{ Protection(BUN)}=100\%-\Delta \text{ BUN post-PR(\% mean of veh.)}$$

Figure 5:
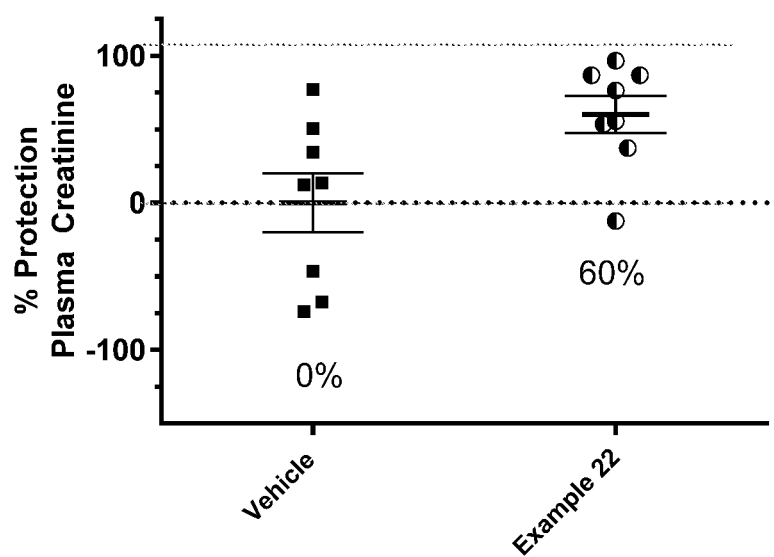
FIG. 5 depicts Plasma Creatinine, % Protection, mean±SEM. See Example 33.
Figure 6:
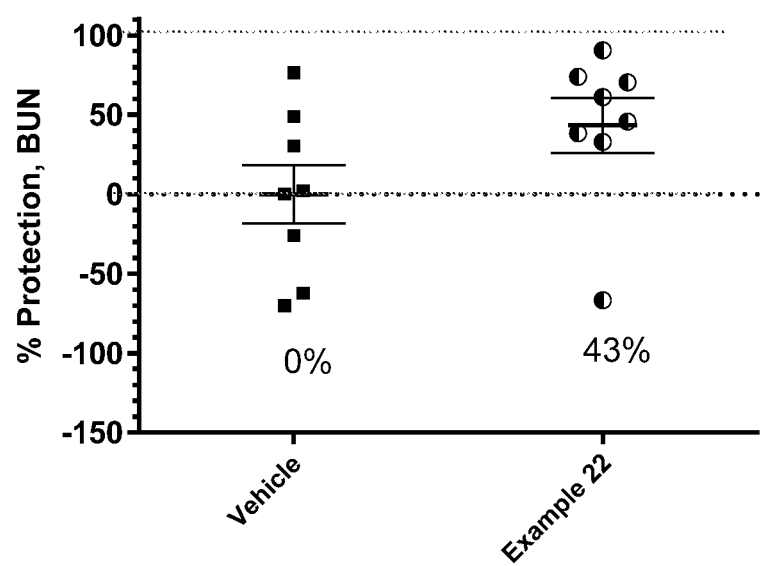
FIG. 6 depicts BUN, % Protection, mean±SEM. See Example 33.

See FIGS. 5 and 6.

EQUIVALENTS

Having described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

INCORPORATION BY REFERENCE

All U.S. patents and U.S. and PCT published patent applications mentioned in the description above are incorporated by reference herein in their entirety.

We claim:

1. A compound of formula (I), or a pharmaceutically acceptable salt thereof:

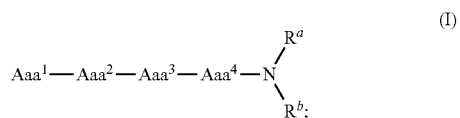

wherein:
Aaa[1] is an amino acid residue selected from the group consisting of:
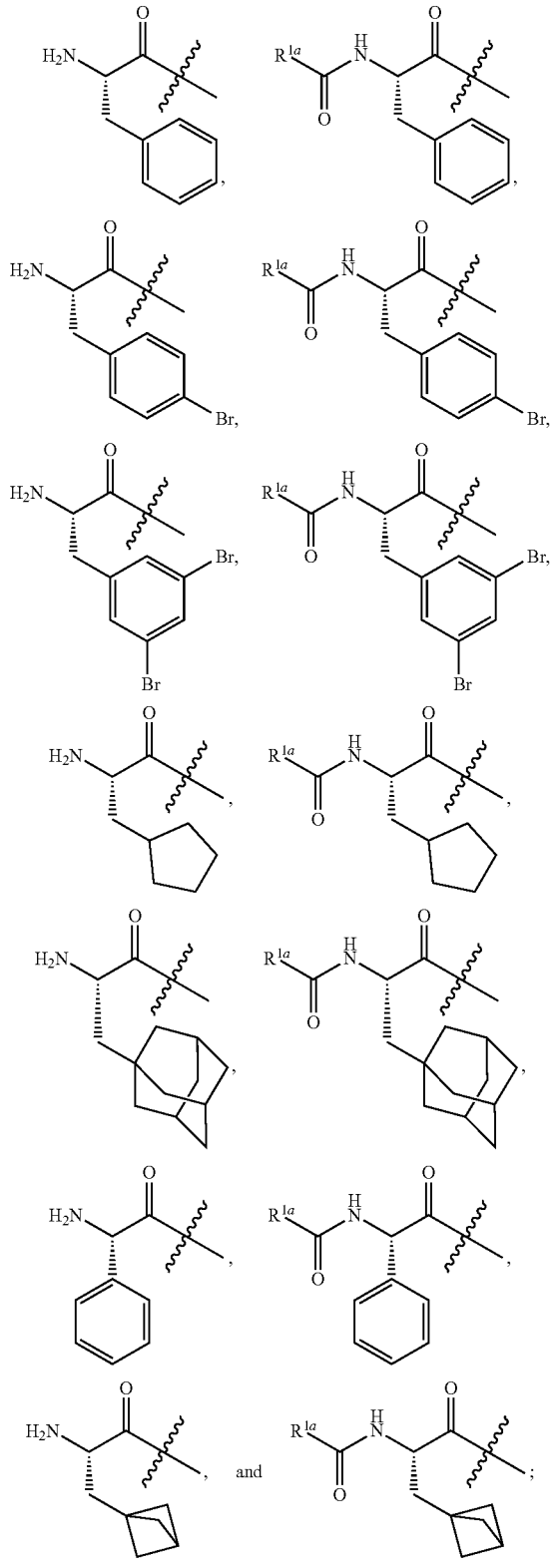
Aaa[2] is an amino acid residue selected from the group consisting of:
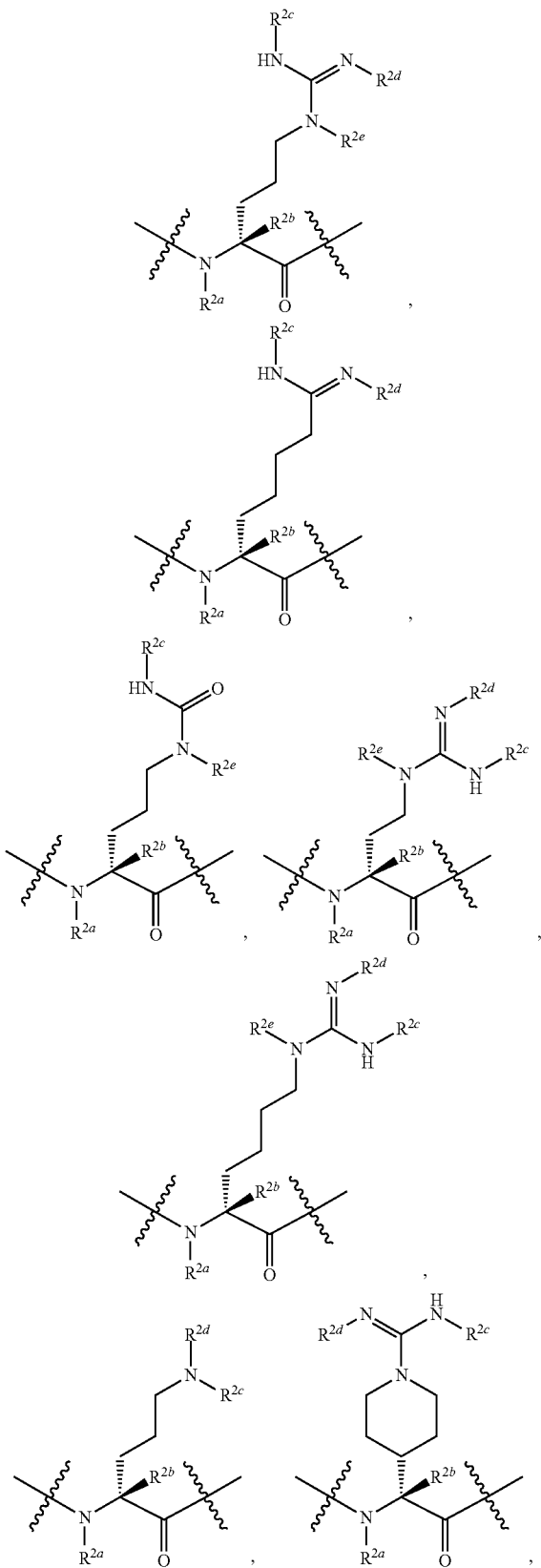

141
-continued
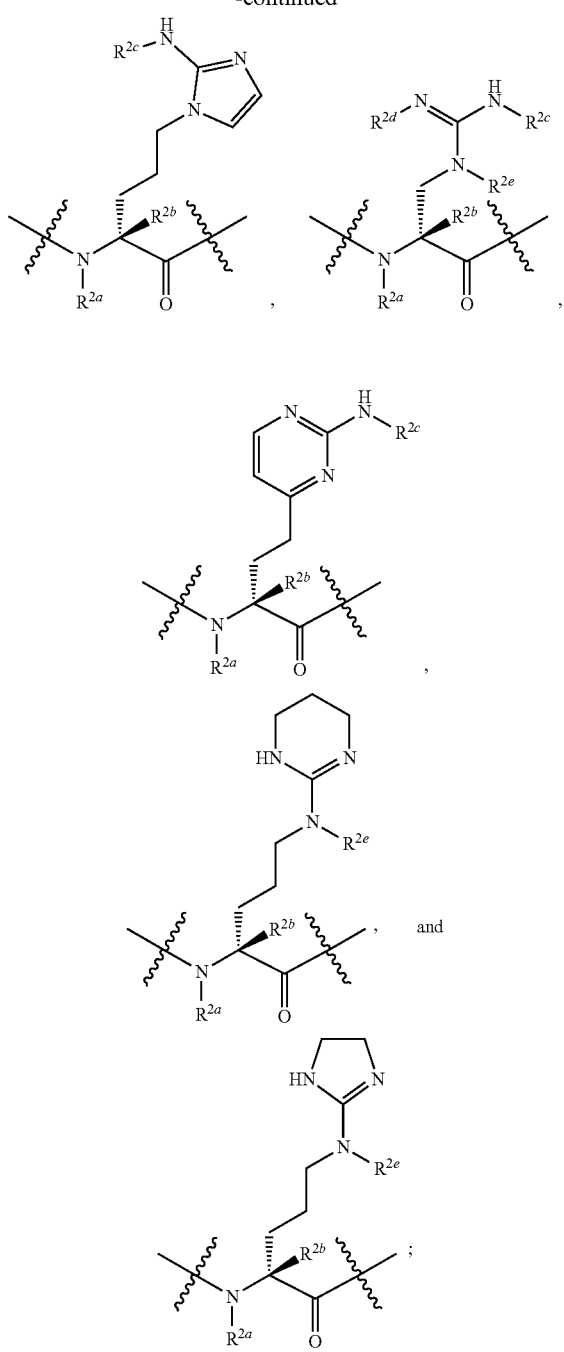
Aaa³ is an amino acid residue selected from the group consisting of:
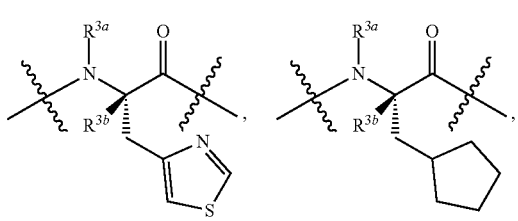
142
-continued
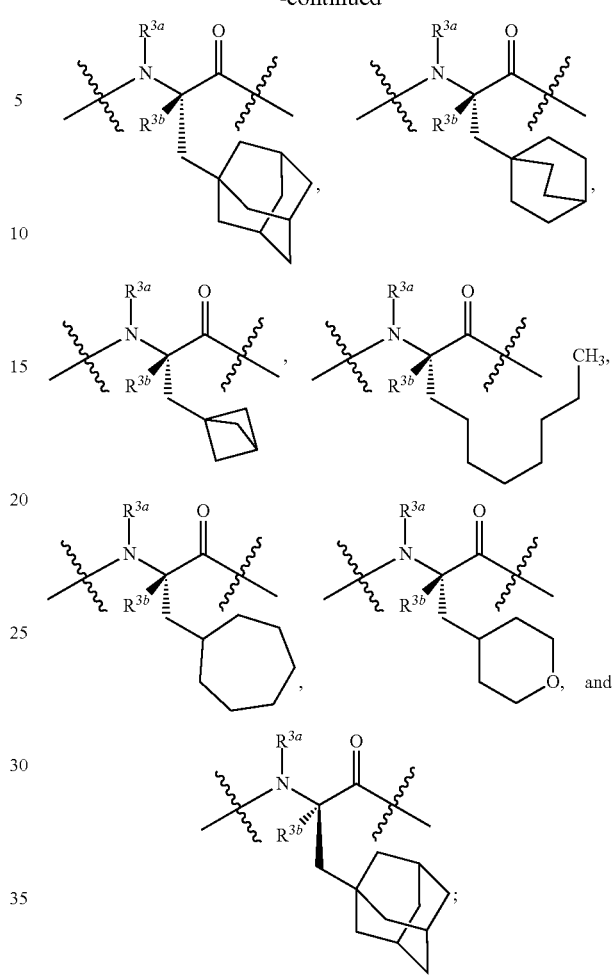
Aaa⁴ is an amino acid residue selected from the group consisting of:
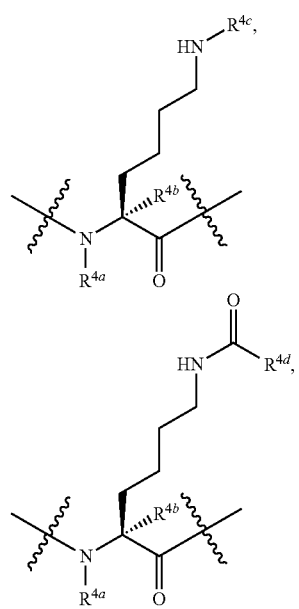

-continued
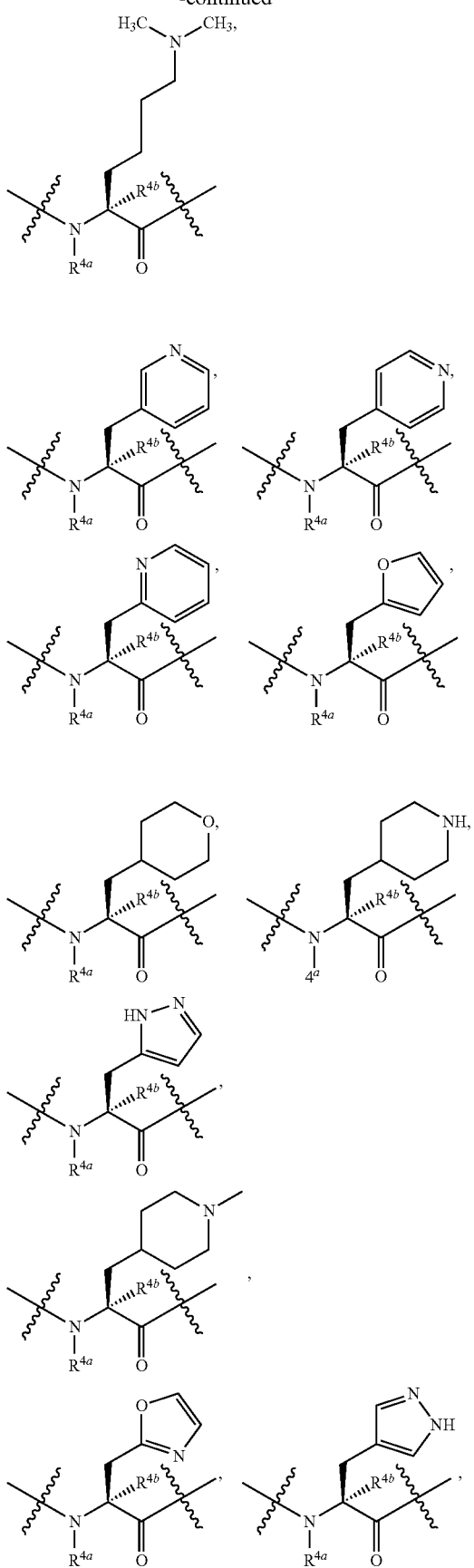
-continued
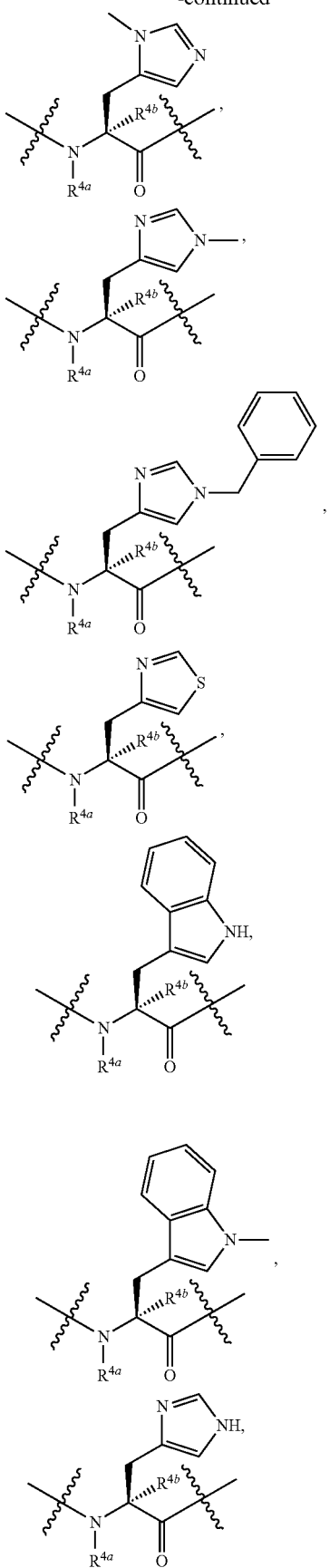

-continued

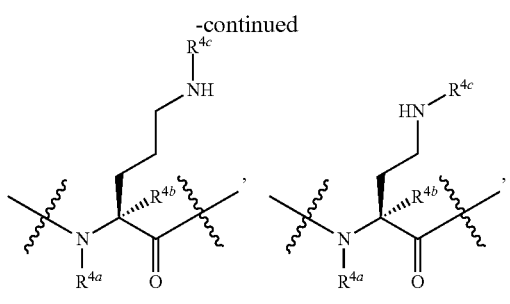

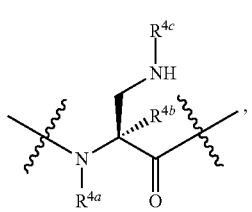

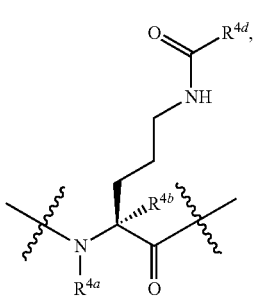

$R^{1a}$ and $R^{4d}$ are each independently $(C_1-C_6)$alkyl;

$R^{2a}$, $R^{2b}$, $R^{2e}$, $R^{3a}$, $R^{3b}$, $R^{4a}$, $R^{4b}$, $R^{4c}$ are each independently selected from the group consisting of H and $(C_1-C_6)$alkyl; and $R^a$, $R^b$, $R^{2c}$, and $R^{2d}$ are each independently selected from the group consisting of H, $(C_1-C_6)$alkyl, $C(O)((C_1-C_6)$alkyl), $C(O)((C_1-C_6)$ haloalkyl), $C(O)O((C_1-C_6)$alkyl), and $C(O)O(aryl\ (C_1-C_6)$alkyl).

2. The compound of claim 1, wherein $Aaa^1$ is selected from the group consisting of:

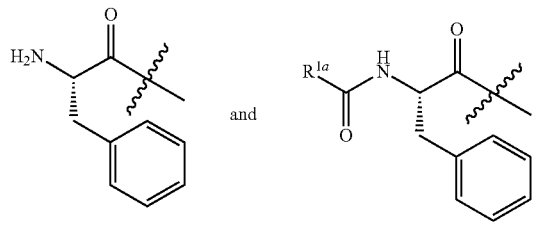

3. The compound of claim 2, wherein $Aaa^1$ is

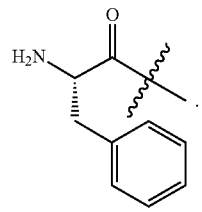 [SMILES: *C(=O)[C@@H](N)Cc1ccccc1]

4. The compound of claim 1, wherein $Aaa^1$ is an amino acid residue selected from the group consisting of:

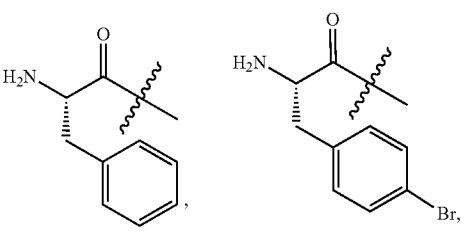

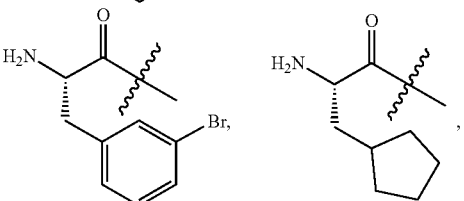

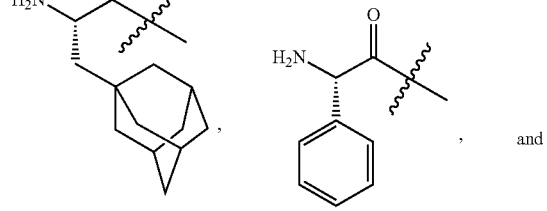

5. The compound of claim 1, wherein Aaa² is selected from the group consisting of:
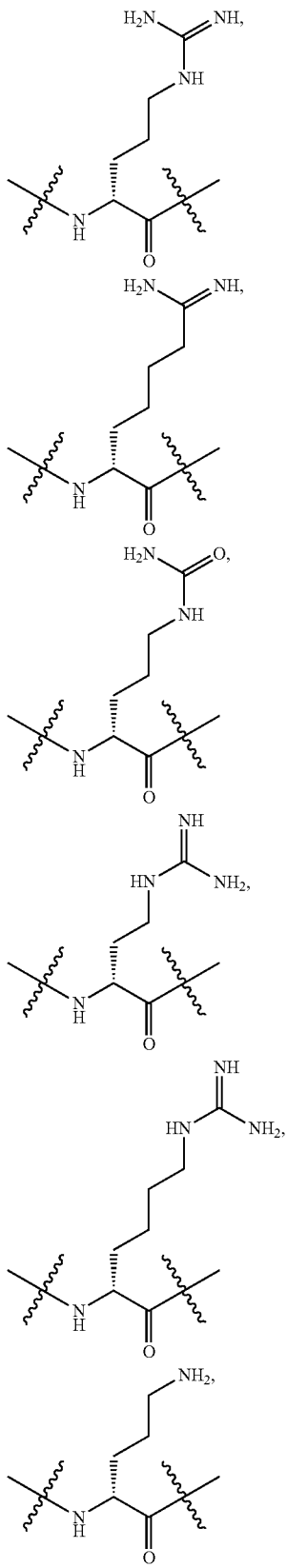
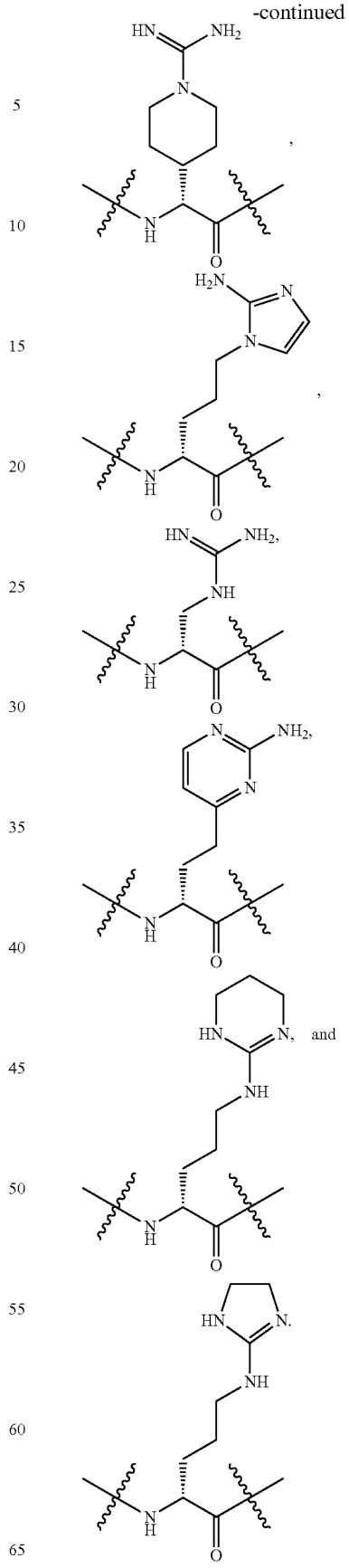

6. The compound of claim 1, wherein Aaa² is
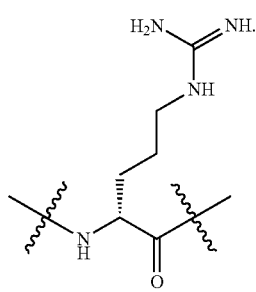 [SMILES: *N[C@H](CCCNC(=N)N)C(*)=O]
7. The compound of claim 1, wherein Aaa³ is selected from the group consisting of:
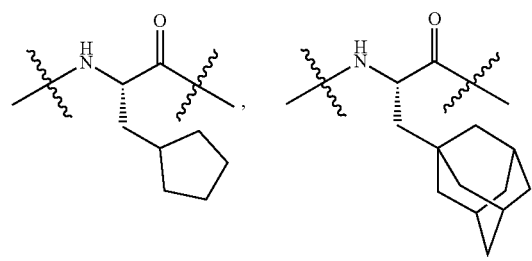
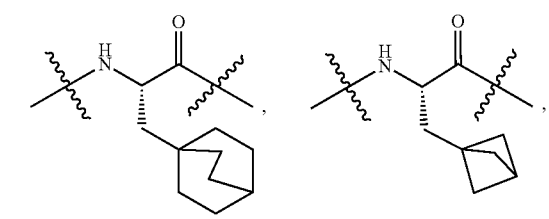
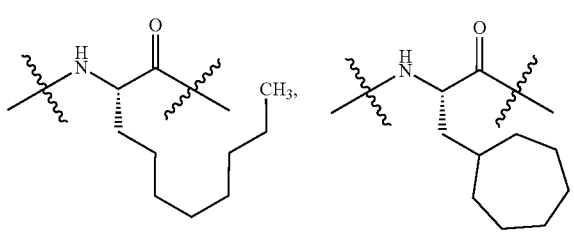
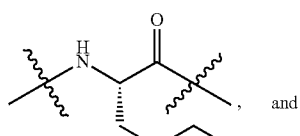, and
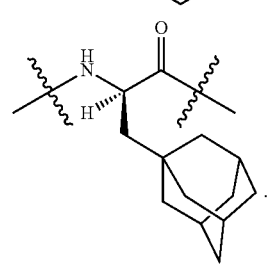
8. The compound of claim 1, wherein Aaa³ is selected from the group consisting of:
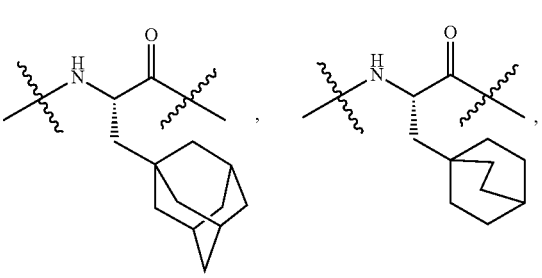
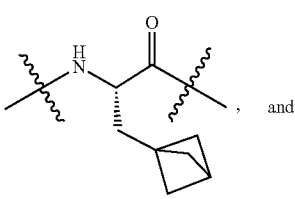, and
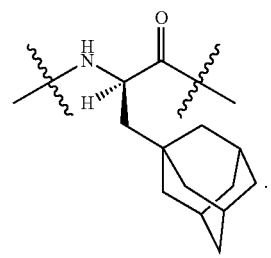
9. The compound of claim 1, wherein Aaa³ is selected from the group consisting of:
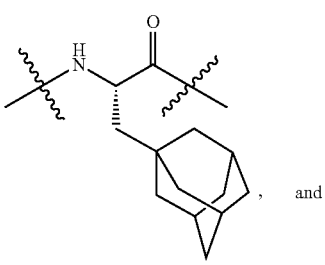, and
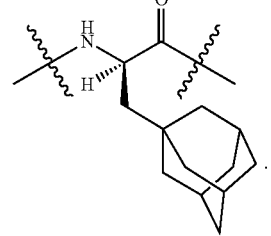

10. The compound of claim 1, wherein Aaa⁴ is selected from the group consisting of:
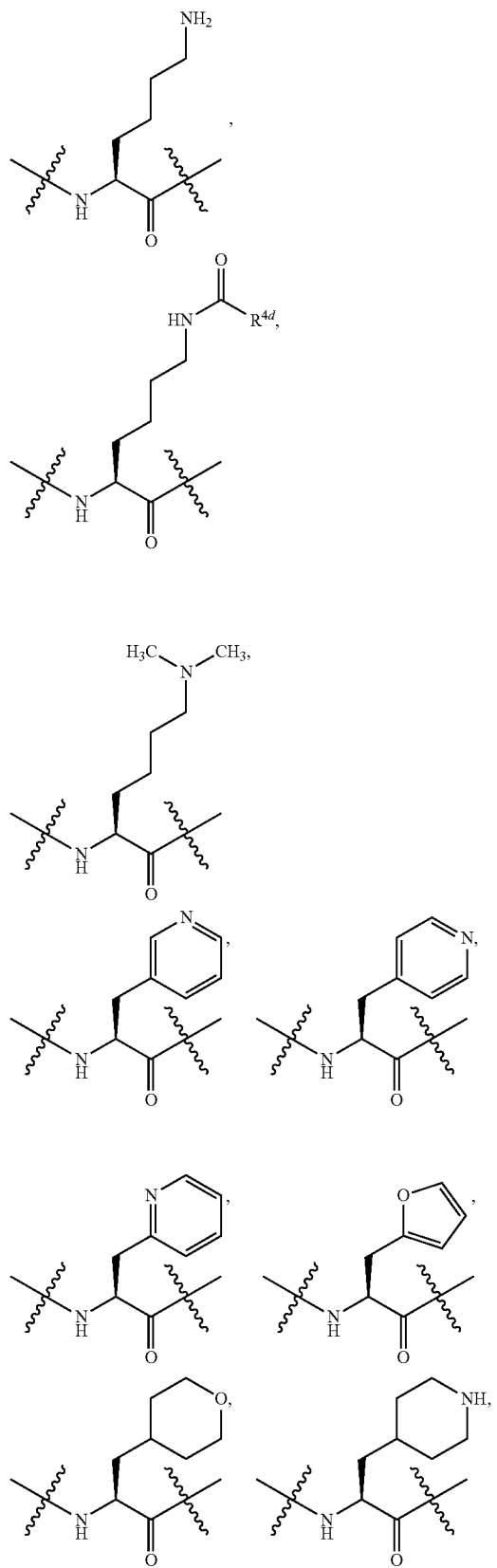
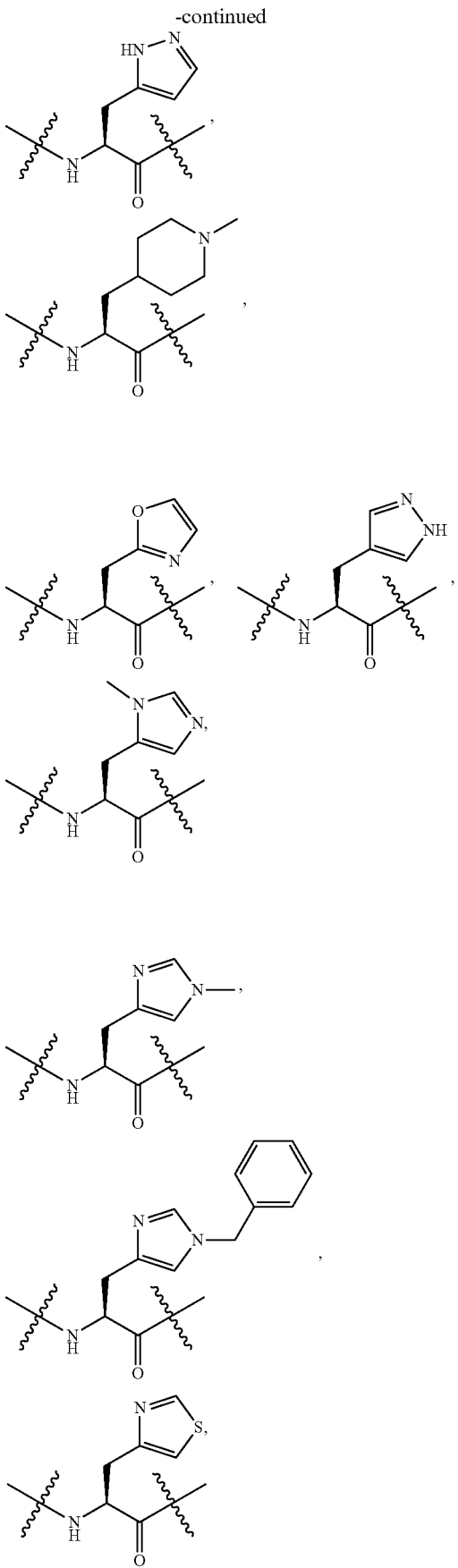

-continued
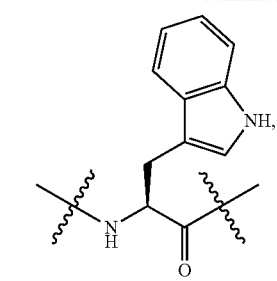
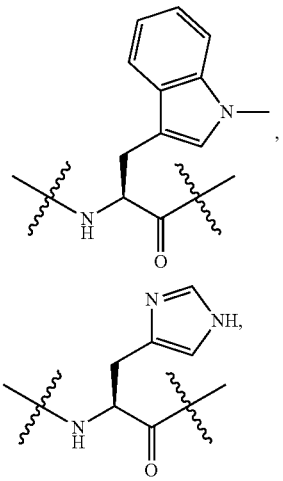
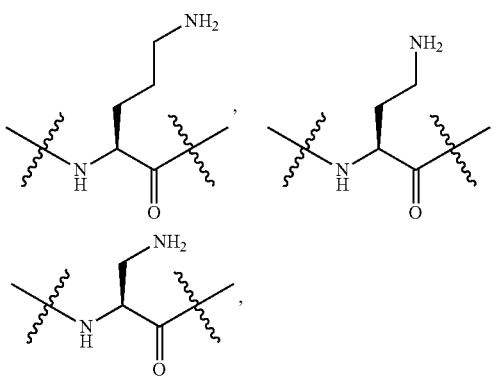
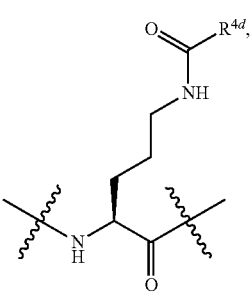
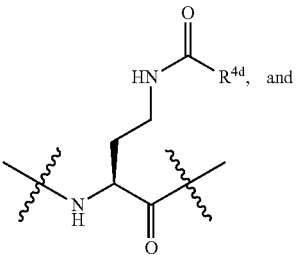
-continued
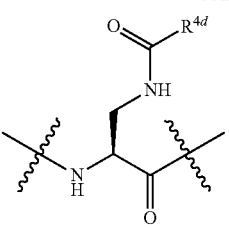
11. The compound of claim 1, wherein Aaa⁴ is selected from the group consisting of:
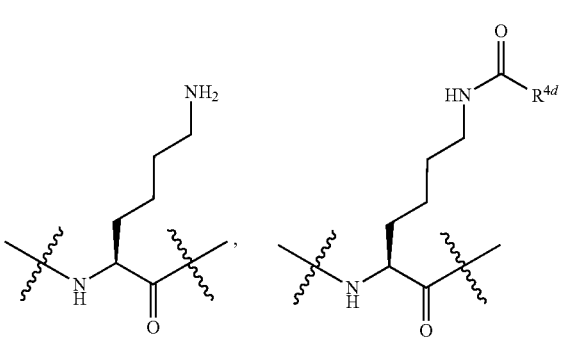
, 
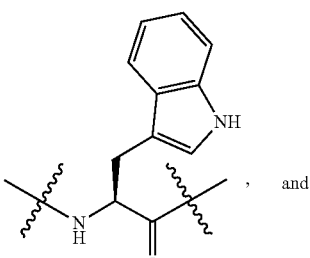
, and
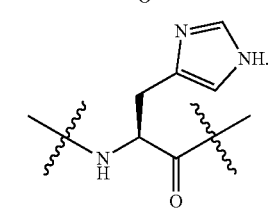
.
12. The compound of claim 1, wherein Aaa⁴ is selected from the group consisting of:
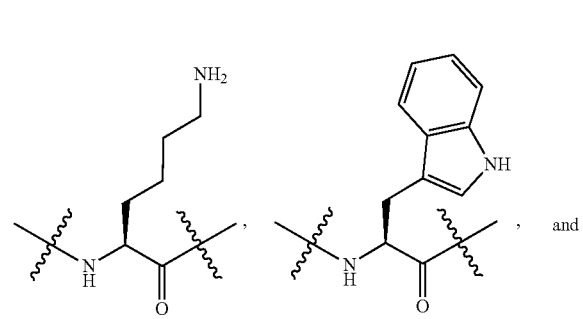
, and

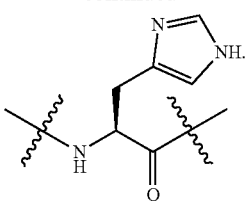
13. The compound of claim 1, wherein $R^a$ and $R^b$ are each independently H or methyl.
14. The compound of claim 1, wherein $R^a$ and $R^b$ are each H.
15. The compound of claim 1, or a pharmaceutically acceptable salt thereof, selected from the following table:
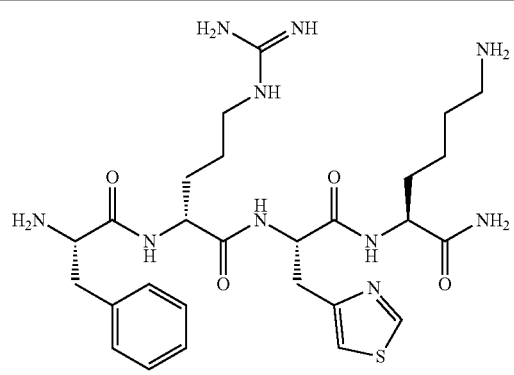 [SMILES: N=C(N)NCCC[C@@H](NC(=O)[C@@H](N)Cc1ccccc1)C(=O)N[C@@H](Cc1cscn1)C(=O)N[C@@H](CCCCN)C(N)=O]
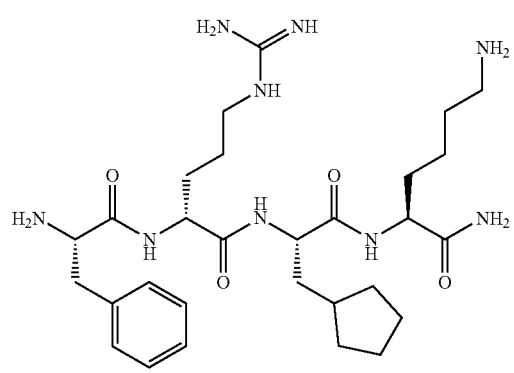
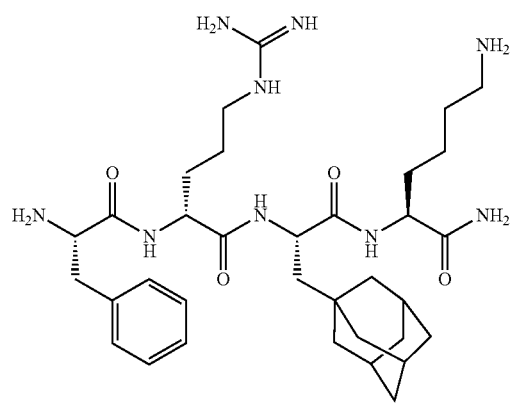 [SMILES: N=C(N)NCCC[C@@H](NC(=O)[C@@H](N)Cc1ccccc1)C(=O)N[C@@H](CC12CC3CC(CC(C3)C1)C2)C(=O)N[C@@H](CCCCN)C(N)=O]
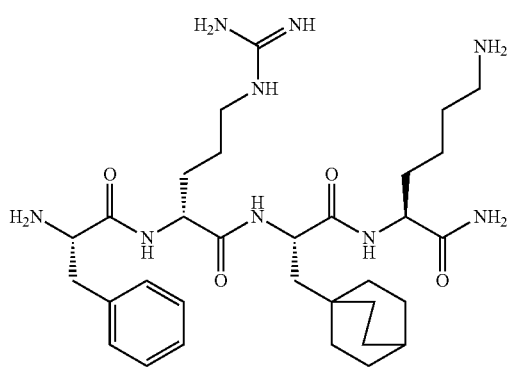 [SMILES: N=C(N)NCCC[C@@H](NC(=O)[C@@H](N)Cc1ccccc1)C(=O)N[C@@H](CC12CCC(CC1)CC2)C(=O)N[C@@H](CCCCN)C(N)=O]
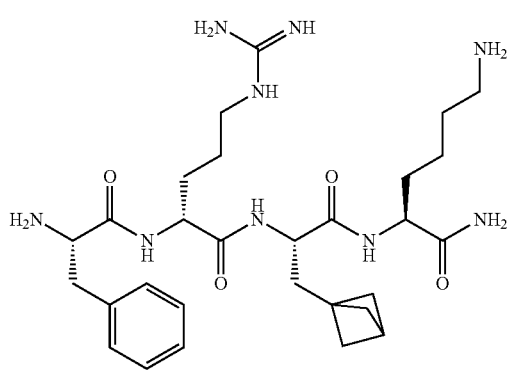 [SMILES: N=C(N)NCCC[C@@H](NC(=O)[C@@H](N)Cc1ccccc1)C(=O)N[C@@H](CC12CC(C1)C2)C(=O)N[C@@H](CCCCN)C(N)=O]
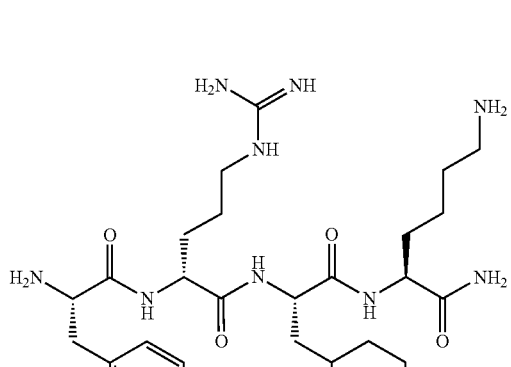
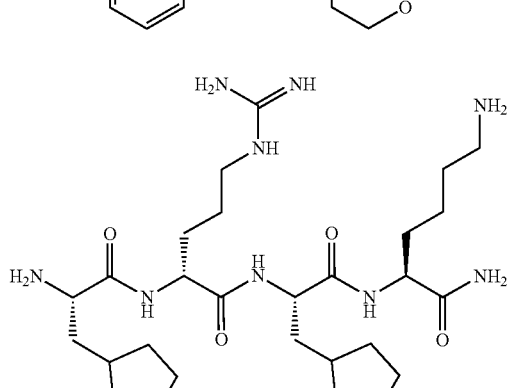

-continued

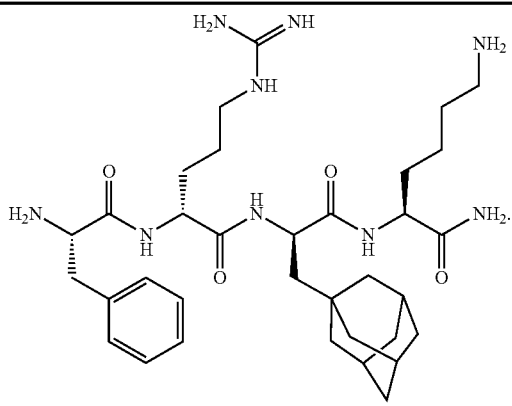

16. A pharmaceutical composition, comprising a compound of claim 1, or a pharmaceutically acceptable salt thereof; and a pharmaceutically acceptable carrier.

17. The compound of claim 15, or a pharmaceutically acceptable salt thereof, wherein the compound is:

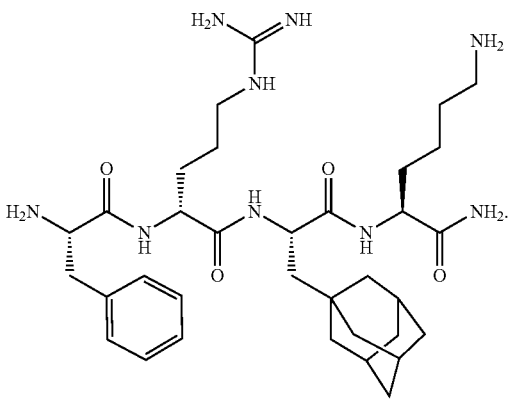 [SMILES: N=C(N)NCCC[C@@H](NC(=O)[C@@H](N)Cc1ccccc1)C(=O)N[C@@H](CC12CC3CC(CC(C3)C1)C2)C(=O)N[C@@H](CCCCN)C(N)=O]

18. The compound of claim 15, or a pharmaceutically acceptable salt thereof, wherein the compound is:

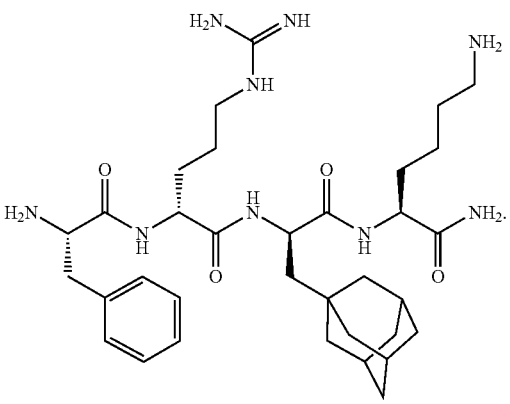 [SMILES: N=C(N)NCCC[C@@H](NC(=O)[C@@H](N)Cc1ccccc1)C(=O)N[C@H](CC12CC3CC(CC(C3)C1)C2)C(=O)N[C@@H](CCCCN)C(N)=O]

19. A method for treating or preventing ischemia-reperfusion injury in a subject in need thereof comprising administering to the subject a therapeutically effective amount of a compound of claim 1, or a pharmaceutically acceptable salt thereof.

20. The method of claim 19, wherein the ischemia-reperfusion injury is cardiac ischemia-reperfusion injury.

21. A method for treating or preventing a myocardial infarction in a subject in need thereof comprising administering to the subject a therapeutically effective amount of a compound of claim 1, or a pharmaceutically acceptable salt thereof.

22. The method of claim 19, wherein the compound is administered orally, topically, systemically, intravenously, subcutaneously, intraperitoneally, or intramuscularly.

* * * * *